United States Patent [19]

Toru et al.

[11] Patent Number: 4,472,428
[45] Date of Patent: Sep. 18, 1984

[54] HALOGENATED PROSTACYCLINS PHARMACEUTICAL USE THEREOF AND HYDROXY INTERMEDIATES THEREFORE

[75] Inventors: Takeshi Toru, Hachioji; Kiyoshi Bannai, Hino; Takeo Oba, Hino; Toshio Tanaka, Hino; Noriaki Okamura, Chofu; Kenzo Wantanabe, Hino; Seizi Kurozumi, Kokubunji; Akira Ohtsu, Ohme; Tatsuyuki Naruchi, Hino, all of Japan

[73] Assignee: Teijin Limited, Osaka, Japan

[21] Appl. No.: 327,741

[22] Filed: Dec. 4, 1981

[30] Foreign Application Priority Data

Dec. 9, 1980 [JP] Japan .................. 55-172543
Apr. 6, 1981 [JP] Japan .................. 56-50492
Jun. 2, 1981 [JP] Japan .................. 56-83779
Jun. 3, 1981 [JP] Japan .................. 56-84463

[51] Int. Cl.$^3$ ................ A61K 31/557; C07D 307/935
[52] U.S. Cl. .................... 424/285; 549/214; 549/305; 549/414; 549/465
[58] Field of Search ............. 549/465, 305, 414, 214; 542/426, 429, 430; 424/285

[56] References Cited

FOREIGN PATENT DOCUMENTS 99580 6/1982 Japan.
171988 10/1982 Japan.
176978 10/1982 Japan.

OTHER PUBLICATIONS

Stringfellow et al., Nature, vol. 282, (1979), pp. 76–78.
Science, vol. 212, (1981), pp. 1270–1272.
Japanese Publication No. 136161/1977 (& Derwent Abstract).
Japanese Publication 95644/1977 (& Derwent Abstract).
Japanese Publication 501,319/1981 (Corresponding to WO81/01002) [& Derwent Abstract].

Primary Examiner—Henry R. Jiles
Assistant Examiner—Bernard Dentz
Attorney, Agent, or Firm—Wenderoct, Lind & Ponack

[57] ABSTRACT

Novel 5- or 7-monohalogenated or 5,7-dihalogenated $^6$-PGI$_1$ and 5- or 7-monohalogenated or dihalogenated PGI$_2$(except 5-monofluorinated PGI$_2$). The novel halogenated prostacyclins are useful for controlling vascular actions and also in organ transplantation, extra-corporeal circulation and the like. The present invention also provides processes for preparing the novel halogenated prostacyclins.

23 Claims, No Drawings

HALOGENATED PROSTACYCLINS PHARMACEUTICAL USE THEREOF AND HYDROXY INTERMEDIATES THEREFORE

This invention relates to novel halogenated prostacyclins, and processes for the production thereof, and pharmaceutical uses thereof.

Prostaglandin I2 (to be referred to as PGI2) is a known compound of the following formula:

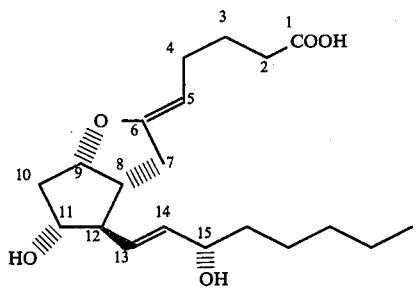

PGI2 is released mainly from the vascular endothelium and has an action of inhibiting platelet aggregation and an antihypertensive action based on its smooth muscle-relaxing action (see Japanese Laid-Open Patent Publication No. 136161/1977). Because of these actions, PGI2 is an important compound which is expected to be used as medicines (see, for example, J. R. Vane et al., Prostacyclin, Raven Press, N.Y., 1979; and J. Med. Chem., vol. 23, number 6, June 1980, pages 591-593).

However, the stability of PGI2 as a medicine is not satisfactory because the half period of its activity at physiological pH is only about several minutes. The instability of PGI2 is considered to be due to the fact that chemically the vinyl ether structure containing a double bond at $\Delta^5$ is readily hydrated to 6-oxoprostaglandin and in vivo, it is rapidly metabolized by a 15-position dehydrogenase. On the other hand, PGI2 is considered to be not entirely satisfactory in its pharmacological actions because the doses required for platelet aggregation inhibiting action and antihypertensive action are almost equal to each other and its selectivity of action as a medicine is inferior. Accordingly, a great deal of efforts have been made in the art to synthesize many kinds of PGI2 and remedy the aforesaid defects of PGI2 (see, for example, S. M. Roberts, Chemistry, Biochemistry & Pharmacological Activity of Prostanoids, Pergamon Press, Oxford, 1979). Examples of known PGI2 in which the enol ether is stabilized are shown below.

(1) 6,9-Imino derivatives [G. L. Bundy et al., Tetrahydron Letters, 1371 (1978)].
(2) 6,9-Thia derivatives [K. C. Nicolaou et al., J. Amer. Chem. Soc. 100, 2567 (1978); M. Shibasaki et al., Tetrahedron Letters, 559 (1978); and Y. Arai et al., Chem. Letters, 1375 (1978)].
(3) 6,9-Carba derivatives [K. C. Nicolaou, et al., Chem. Commun., 1067 (1978); K. Kojima et al., Tetrahedron Letters, 3743 (1978); M. Shibasaki et al., ibid, 433 (1979); Y. Konishi et al., Chem. Letters, 1437 (1979); and D. R. Morton et al., J. Org. Chem. 44, 2880 (1979)].
(4) 5-Oxo derivatives [H. Nishiyama et al., Tetrahedron Letters, 3481 (1979)].
(5) 7-Oxo derivatives (European Patent Publication No. 31,426).
(6) 5-Cyano derivatives (U.S. Pat. No. 4,219,479).
(7) 5-Phenylthio derivatives [T. Toru et al., Tetrahedron Letters, 2539 (1980)].
(8) 6,9-Aza-5-thia derivatives [W. Bartmann et al., Angew. Chem. Int. Ed. Engl. 19, 819 (1980)].

Recently, International Publication Number WO 81/01002 was published which claims prostacyclin compounds having the following structure

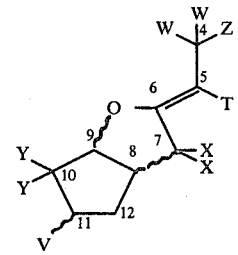

wherein
Y, X, W and T are H or F (provided that at least one of Y, X, W and T should be F), and V is H, OH, acyloxy or alkoxy,
at their $C_4$–$C_{12}$ positions (claim 4), i.e. fluorinated prostacyclins having either one of 4,4-, 5-, 7,7- and 10,10-positions substituted by fluorine (claim 2).

As can be seen from the above structural formula, however, this International Publication only discloses $\Delta^5$-prostacyclins, i.e. PGI2, and does not at all disclose $\Delta^6$-prostacyclins, i.e. $\Delta^6$-PGI1.

The structural characteristic of the $\Delta^5$-prostacylines described in the above International Publication is that when either one of the 4-, 7- or 10-position is fluorinated, that position is always difluorinated (gem-difluorinated).

The above Publication discloses that these fluorinated prostacyclins are produced by cyclizing the corresponding fluorinated $PGF_{2\alpha}$ as starting materials instead of using PGI2 as starting materials. Further, the above Publication does not give any data which specifically show the biological activities of these fluorinated prostacyclins. As far as the present inventors know, it is only with regard to 10,10-difluoro-13,14-de-hydroprostacyclin, i.e. a compound of the following formula

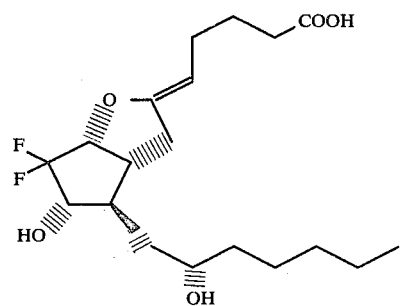

that biological activities are specifically elucidated. J. Fried who is one of the coinventors of the above International Patent Publication and his coworkers reported the vascular relaxing activity and platelet aggregation inhibiting activity in vitro and the chemical stability at a pH of 7.4 of 10,10-difluoro-13,14-dehydroprostacyclin (J. Med. Chem. 1980, 23, 237–239 and Proc. Natl. Acad. Sci., U.S.A. 77, No. 11, 6846–6850, 1980).

It is an object of this invention therefore to provide novel halogenated prostacyclins, i.e. halogenated PGI$_1$ and halogenated PGI$_2$.

Another object of this invention is to provide novel mono- or di-halogenated prostacyclins in which either the 5-position or the 7-position is mono-halogenated or the 5-position and the 7-position are dihalogenated.

Still another object of this invention is to provide novel mono- or di-chlorinated (or -brominated or -iodinated)prostacyclins.

Still another object of this invention is to provide halogenated prostacyclins which are more stabilized than natural PGI$_2$.

Still another object of this invention is to provide halogenated prostacyclins which have biological activities nearly comparable to natural PGI$_2$ and better selective activities than natural PGI$_2$.

Still another object of this invention is to provide halogenated prostacyclins which are useful in controlling the actions of the vascular system, or in organ transplanting, vascular surgery and extracorporeal circulation.

Still another object of this invention is to provide novel prostacyclin intermediates which are useful for the production of the halogenated prostacyclins of the invention having the above desirable properties.

Still another object of this invention is to provide novel processes for the production of the aforesaid novel halogenated prostacyclins.

Further objects and advantages of this invention will become apparent from the following description.

These objects and advantages are achieved by a halogenated prostacyclin selected from the group consisting of halogenated PGI$_1$ of the following formula

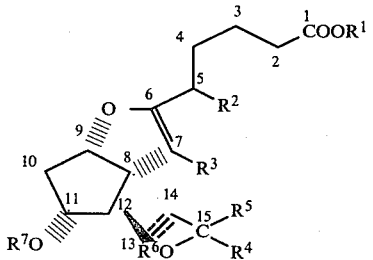

(A$_1$)

wherein
the symbol ≡≡≡ between the 13- and 14-positions indicates that a single, double or triple bond exists between the 13- and 14-positions; $R^1$ represents a hydrogen atom, a C$_1$–C$_{10}$ alkyl group, a substituted or unsubstituted phenyl group, a substituted or unsubstituted alicyclic group, a substituted or unsubstituted phenyl (C$_1$–C$_2$)alkyl group, or one equivalent of a cation whose salt is pharmaceutically acceptable; $R^2$ and $R^3$ represent a hydrogen or halogen atom provide that $R^2$ and $R^3$ are not hydrogen atoms at the same time; $R^4$ represents a hydrogen atom, a methyl group, an ethynyl group or a protected ethynyl group; $R^5$ represents an unsubstituted C$_5$–C$_8$ alkyl group, a C$_1$–C$_5$ alkyl group substituted by a substituent selected from phenyl, phenoxy, C$_1$–C$_6$ alkoxy and C$_5$–C$_6$ cycloalkyl, which substituent may be substituted, or a substituted or unsubstituted alicyclic group; and $R^6$ and $R^7$ are identical or different and each represents a hydrogen atom, a C$_2$–C$_7$ acyl group, a tri(C$_1$–C$_7$)hydrocarbonsilyl group or a group forming an acetal linkage together with the oxygen atom of the hydroxyl group, and halogenated PGI$_2$ of the following formula

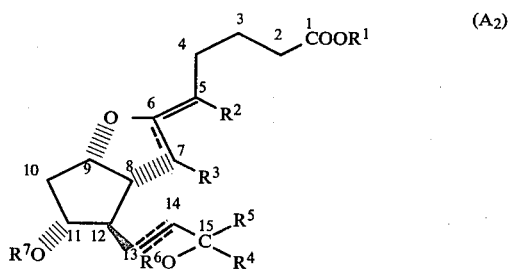

(A$_2$)

wherein
the symbol ≡≡≡ between the 13- and 14-positions, $R^1$, $R^2$, $R^3$, $R^4$, $R^5$, $R^6$ and $R^7$ are as defined above, provided that when $R^2$ is a hydrogen or fluorine atom, $R^3$ is not a hydrogen atom.

Stereoisomers of the halogenated PGI$_1$ of formula (A$_1$) and the halogenated PGI$_2$ of formula (A$_2$) should be understood as follows:

In formulae (A$_1$) and (A$_2$), there are four bonds from the cyclopentane ring, that is, three bonds (indicated by ||||||||||||||) which run downwardly (backwardly of the sheet surface) and one bond (indicated by ▬▬) running upwardly from the sheet surface. Accordingly, stereoisomers of the compounds for formulae (A$_1$) and (A$_2$) are specified by the above formulae with regard to the four bonds running from the cyclopentane ring.

The PGI$_1$ compounds of formula (A$_1$) contain two kinds of stereoisomers with regard to the carbon atom at the 5-position (the asymmetric carbon atom) when $R^2$ bonded to the carbon atom at the 5-position is a halogen atom, and also include two kinds of stereoisomers with regard to the asymmetric carbon atom at the 15-position. It should be understood therefore that the PGI$_1$ compounds of formula (A$_1$) include one of these stereoisomers or a mixture of at least two of these stereoisomers. It should further be understood that when the bond between the carbon atoms at the 13- and 14-positions is a double bond, the PGI$_1$ compounds of formula (A$_1$) include a cis-isomer or transisomer or a mixture thereof with respect to the aforesaid double bond.

The PGI$_2$ compounds of formula (A$_2$) include two stereoisomers with regard to the carbon atom at the 7-position (asymmetric carbon atom) when $R^3$ bonded to the carbon atom at the 7-position is a halogen atom, and further contain two stereoisomers with regard to the asymmetric carbon atoms at the 15-position. Furthermore, the PGI$_2$ compounds of formula (A$_2$) include a cis-isomer or a trans-isomer or a mixture thereof with regard to the double bond between the carbon atoms at the 5- and 6-positions and the double bond between the 13- and 14-positions. It should be understood that the PGI$_2$ compounds of formula (A$_2$) include at least one of these stereoisomers.

In the formulae (A$_1$) and (A$_2$), the symbol ≡≡≡ between the 13- and 14-positions represents a single, double or triple bond.

$R^1$ represents a hydrogen atom, a C$_1$–C$_{10}$ alkyl group, a substituted or unsubstituted phenyl group, a substituted or unsubstituted alicyclic group, a substituted or unsubstituted phenyl($C_1$-$C_2$)alkyl group, or one equivalent of a cation whose salt is pharmaceutically acceptable.

Examples of the $C_1$-$C_{10}$ alkyl group include linear or branched alkyl groups of 1 to 10 carbon atoms, such as methyl, ethyl, n-propyl, iso-propyl, n-butyl, sec-butyl, tert-butyl, n-pentyl, n-hexyl, n-heptyl, n-octyl, n-nonyl and n-decyl.

Examples of suitable substituents for the substituted phenyl group for $R^1$ are halogen atoms, a hydroxyl group, $C_2$-$C_7$ acyloxy groups, $C_1$-$C_4$ alkyl groups which may be halogenated, $C_1$-$C_4$ alkoxy groups which may be halogenated, a nitrile group, a carboxyl group and ($C_1$-$C_6$)alkoxycarbonyl groups. The halogen atoms are fluorine, chlorine and bromine atoms, and fluorine and chlorine atoms are preferred. Examples of the $C_2$-$C_7$ acyloxy groups are acetoxy, propionyloxy, n-butyryloxy, isobutyryloxy, n-valeryloxy, iso-valeryloxy, caproyloxy, enanthyloxy or benzoyloxy.

Examples of suitable $C_1$-$C_4$ alkyl groups which may be halogenated include methyl, ethyl, n-propyl, isopropyl, n-butyl, chloromethyl, dichloromethyl, and trifluoromethyl.

Examples of suitable $C_1$-$C_4$ alkoxy groups which may be halogenated include methoxy, ethoxy, n-propoxy, iso-propoxy, n-butoxy, chloromethoxy, dichloromethoxy, tri-fluoromethoxy.

Examples of the ($C_1$-$C_6$)alkoxycarbonyl group are methoxycarbonyl, ethoxycarbonyl, butoxycarbonyl and hexyloxycarbonyl.

The substituted phenyl group may contain 1 to 3, preferably 1, substituents exemplified above.

The substituted or unsubstituted alicyclic group may be a saturated or unsaturated $C_5$-$C_8$, preferably $C_5$-$C_6$, especially preferably $C_6$, group, such as cyclopentyl, cyclohexyl, cyclohexenyl, cycloheptyl, or cyclooctyl, which is unsubstituted or substituted by the same substituents as exemplified thereabove.

Examples of the substituted or unsubstituted phenyl(-$C_1$-$C_2$) alkyl group are benzyl, α-phenethyl, and β-phenethyl in which the phenyl group may be substituted by the same substituents as exemplified hereinabove.

Examples of one equivalent of a cation include ammonium cations such as $NH_4^+$, or a tetramethyl ammonium, monomethyl ammonium, dimethyl ammonium, trimethyl ammonium, benzyl ammonium, phenethyl ammonium, morpholinium, monoethanol ammonium, or piperidinium cation; alkali metal cations such as $Na^+$ or $K^+$; and divalent or trivalent metal cations such as $1/2Ca^{2+}$, $1/2Mg^{2+}$, $1/2Zn^{2+}$, and $1/3Al^{3+}$.

$R^1$ is preferably a hydrogen atom, a $C_1$-$C_{10}$ alkyl group, or one equivalent of a cation whose salt is pharmaceutically acceptable.

$R^2$ and $R^3$ are identical or different, and each represents a hydrogen atom or a halogen atom. The halogen atom may be a fluorine, chlorine, bromine or iodine atom.

$R^4$ represents a hydrogen atom, a methyl group, an ethynyl group (—C≡CH) or a protected ethynyl group. The protected ethynyl is preferably a trimethylsilylethynyl or t-butyldimethylsilylethynyl group. Preferably, $R^4$ is a hydrogen atom or a methyl group.

$R^5$ represents an unsubstituted $C_5$-$C_8$ alkyl group; a substituted $C_1$-$C_5$ alkyl group substituted by a substituent selected from a phenyl group, a phenoxy group, a $C_1$-$C_6$ alkoxy group and a $C_5$-$C_6$ cycloalkyl group, which substituent may be substituted; or a substituted or unsubstituted alicyclic group. The unsubstituted $C_5$-$C_8$ alkyl group may be linear or branched, and includes, for example, n-pentyl, n-hexyl, 2-methyl-1-hexyl, 2-methyl-2-hexyl, n-heptyl, and n-octyl. The n-pentyl, n-hexyl, 2-methyl-1-hexyl, and 2-methyl-2-hexyl are preferred. The substituted $C_1$-$C_5$ alkyl group may be linear or branched, and includes, for example, methyl, ethyl, n-propyl, iso-propyl, n-butyl, sec-butyl, t-butyl and n-pentyl. These alkyl groups are substituted by a phenyl group; a phenoxy group; a $C_1$-$C_6$ alkoxy group such as methoxy, ethoxy, n-propoxy, iso-propoxy, n-butoxy, isobutoxy, t-butoxy, n-pentoxy, or n-hexoxy; or a $C_5$-$C_6$ cycloalkyl group such as cyclopentyl or cyclohexyl. These substituents may be substituted by the same substituents as cited hereinabove as the substituents for the substituted phenyl group $R^1$.

Examples of preferred substituted $C_1$-$C_5$ alkyl groups are $C_1$-$C_2$ alkyl groups substituted by a phenoxy or phenyl group which may further be substituted by a chlorine or fluorine atom or a methyl, ethyl or trifluoromethyl group; and propoxymethyl, ethoxyethyl, propoxyethyl, butoxymethyl, methoxypropyl, 2-ethoxy-1,1-dimethylethyl, propoxydimethylmethyl, cyclohexylmethyl, cyclohexylethyl, cyclohexyldimethylmethyl and 2-cyclohexyl-1,1-dimethylethyl. The substituted or unsubstituted alicyclic group may include the same species as cited with regard to $R^1$.

Preferably, $R^5$ is n-pentyl, n-hexyl, 2-methyl-1-hexyl, 2-methyl-2-hexyl, or cyclohexyl.

$R^6$ and $R^7$ are identical or different, and each represents a hydrogen atom, a $C_2$-$C_7$ acyle group, a tri-($C_1$-$C_7$) hydrocarbonsilyl group or a group forming an acetal linkage together with the oxygen atom of the hydroxyl group. Examples of the $C_2$-$C_7$ acyl group are acetyl, propionyl, n-butyryl, iso-butyryl, n-valeryl, iso-valeryl, caproyl, enanthyl and benzoyl. Of these, $C_2$-$C_6$ aliphatic acyl groups such as acetyl, n- or iso-butyryl, caproyl and benzoyl are preferred. Examples of suitable tri($C_1$-$C_7$)hydrocarbon-silyl groups include tri($C_1$-$C_4$) alkylsilyl groups such as trimethylsilyl, triethysilyl or t-butyldimethylsilyl, ($C_1$-$C_4$)alkyldiphenylsilyl groups such as t-butyldiphenylsilyl, and a tribenzylsilyl group. Examples of the group forming an acetal linkage with the oxygen atom of the hydroxyl group are methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo[3.1.0]hex-4-yl. Of these, 2-tetrahydropyranyl, 2-tetrahydrofuranyl, 1-ethoxyethyl, 2-methoxy-2-propyl, and (2-methoxyethoxy)methyl, and 6,6-dimethyl-3-oxa-2-oxo-bicyclo[3.1.0-]hex-4-yl are preferred.

It should be understood that the hydrocarbon-silyl group, the acyl group and the group forming an acetal linkage are protective groups for the hydroxyl group. The hydrocarbon-silyl group or the acetal-forming group can be easily removed under acidic to neutral conditions. The acyl group can be easily removed under basic conditions.

Preferred as $R^6$ or $R^7$ are a hydrogen atom, a tri($C_1$-$C_4$)alkylsilyl group, a ($C_1$-$C_4$)alkyldiphenyl silyl group, a 2-tetrahydropyranyl group, a 2-tetrahydrofuranyl group, a 1-ethoxyethyl group, a 2-ethoxy-3-propyl group, a (2-methoxyethoxy)methyl group, a 6,6-dimethyl-3-oxa-2-oxo-bycyclo[3.1.0]hex-4-yl group, an acetyl group, and a benzoyl group.

The halogenated prostacyclins of the invention can be divided, for the sake of convenience, into a group of compounds having a double bond between the 6- and 7-positions (PGI$_1$ of formula A$_1$) and a group of compounds having a double bond between the 5- and 6-positions (PGI$_2$ of formula A$_2$).

The halogenated prostacyclins of the invention exclude PGI$_1$ of formula (A$_1$) in which both R$^2$ and R$^3$ are hydrogen atoms, and PGI$_2$ of formula (A$_2$) in which R$^3$ is a hydrogen atom and R$^2$ is a hydrogen atom or a fluorine atom.

PGI$_1$ or PGI$_2$ compounds of formula (A$_1$) or (A$_2$) in which the bond between the 13- and 14-positions is a trans-double bond or a triple bond form a preferred group of halogenated prostacyclins of the invention.

Preferred PGI$_2$ compounds of formula (A$_2$) are those in which a double bond exists between the 5- and 6-positions and the bond between the carbon atom at the 5-position of the double bond and the carbon atom at the 4-position is cis to the bond between the carbon atom at the 6-position of the double bond and the oxygen atom.

Among the halogenated prostacyclins of the invention, halogenated PGI$_1$ of the formula

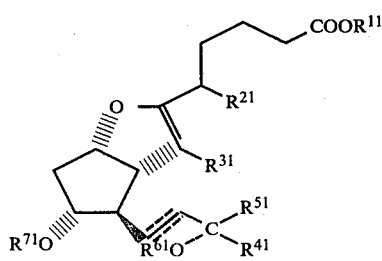

wherein
the symbol ======== between the 13- and 14-positions represents a single, double or triple bond; R$^{11}$ represents a hydrogen atom, a C$_1$–C$_{10}$ alkyl group or one equivalent of a cation whose salt is pharmaceutically acceptable; R$^{21}$ and R$^{31}$ represent a hydrogen, fluorine or chlorine atom, provided that R$^{21}$ and R$^{31}$ are not hydrogen atoms at the same time; R$^{41}$ represents a hydrogen atom or a methyl group; R$^{51}$ represents an n-pentyl, n-hexyl, 2-methyl-1-hexyl, 2-methyl-2-hexyl or cyclohexyl group; and R$^{61}$ and R$^{71}$ represent a hydrogen atom or an acetyl group;
and halogenated PGI$_2$ of the formula (A$_2$)-1 wherein
the symbol ======== between the 13- and 14-positions, R$^{11}$, R$^{21}$, R$^{31}$, R$^{41}$, R$^{51}$, R$^{61}$ and R$^{71}$ are as defined above, provided that R$^{31}$ is not a hydrogen atom when R$^{21}$ is a hydrogen or fluorine atom,
form a group of compounds which are desirable in dosage forms.

Compounds of formula (A$_1$)-1 or (A$_2$)-1 in which the bond between the 13- and 14-positions is a trans-double bond or a triple bond are preferred because they have especially superior pharmacological activities.

Compounds of formula (A$_2$)-1 in which the bond between the carbon atom at the 5-position of the double bond between the 5- and 6-positions and the carbon atom at the 4-position is cis to the bond between the carbon atom at the 6-position of the above double bond and the oxygen atom are especially preferred.

Specific examples of the compounds of formula (A$_1$) [including formula (A$_1$)-1] and the compounds of formula (A$_2$) [including formula (A$_2$)-1] are given below.

| | Compounds of formula (A$_1$) |
|---|---|
| (100) | 5-Fluoro-Δ$^6$-PGI$_1$, |
| (101) | 7-Fluoro-Δ$^6$-PGI$_1$, |
| (102) | 5-Chloro-Δ$^6$-PGI$_1$, |
| (103) | 7-Chloro-Δ$^6$-PGI$_1$, |
| (104) | 5-Bromo-Δ$^6$-PGI$_1$, |
| (105) | 7-Bromo-Δ$^6$-PGI$_1$, |
| (106) | 5-Iodo-Δ$^6$-PGI$_1$, |
| (107) | 7-Iodo-Δ$^6$-PGI$_1$, |
| (108) | 5,7-Difluoro-Δ$^6$-PGI$_1$, |
| (110) | 5,7-Dichloro-Δ$^6$-PGI$_1$, |
| (112) | 5,7-Dibromo-Δ$^6$-PGI$_1$, |
| (114) | 5,7-Diiodo-Δ$^6$-PGI$_1$, |
| (116) | 5-Chloro-7-fluoro-Δ$^6$-PGI$_1$, |
| (118) | 5-Bromo-7-fluoro-Δ$^6$-PGI$_1$, |
| (120) | 7-Fluoro-5-iodo-Δ$^6$-PGI$_1$, |
| (122) | 7-Chloro-5-fluoro-Δ$^6$-PGI$_1$, |
| (124) | 7-Bromo-5-chloro-Δ$^6$-PGI$_1$, |
| (126) | 5-Fluoro-13,14-dehydro-Δ$^6$-PGI$_1$, |
| (128) | 5-Chloro-13,14-dehydro-Δ$^6$-PGI$_1$, |
| (130) | 5-Bromo-13,14-dehydro-Δ$^6$-PGI$_1$, |
| (132) | 5,7-Difluoro-13,14-dehydro-Δ$^6$-PGI$_1$, |
| (134) | 5,7-Dichloro-13,14-dehydro-Δ$^6$-PGI$_1$, |
| (136) | 7-Bromo-5-chloro-13,14-dehydro-Δ$^6$-PGI$_1$, |
| (138) | 5-Fluoro-13,14-dihydro-Δ$^6$-PGI$_1$, |
| (140) | 5-Chloro-13,14-dihydro-Δ$^6$-PGI$_1$, |
| (142) | 5-Bromo-7-chloro-13,14-dihydro-Δ$^6$-PGI$_1$, |
| (144) | 5-Fluoro-17(R),20-dimethyl-Δ$^6$-PGI$_1$, |
| (145) | 7-Fluoro-17(R),20-dimethyl-Δ$^6$-PGI$_1$, |
| (146) | 5-Chloro-17(R),20-dimethyl-Δ$^6$-PGI$_1$, |
| (148) | 5-Bromo-17(R),20-dimethyl-Δ$^6$-PGI$_1$, |
| (150) | 5,7-Dichloro-17(R),20-dimethyl-Δ$^6$-PGI$_1$, |
| (152) | 5-Fluoro-17(S),20-dimethyl-Δ$^6$-PGI$_1$, |
| (153) | 5-Fluoro-17(R),20-dimethyl-Δ$^6$-PGI$_1$, |
| (154) | 5-Chloro-17(S),20-dimethyl-Δ$^6$-PGI$_1$, |
| (156) | 5-Bromo-17(S),20-dimethyl-Δ$^6$-PGI$_1$, |
| (158) | 5,7-Difluoro-17(S),20-dimethyl-Δ$^6$-PGI$_1$, |
| (160) | 15-Cyclohexyl-5-fluoro-16,17,18,19,20-pentanor-Δ$^6$-PGI$_1$, |
| (162) | 5-Chloro-15-cyclohexyl-16,17,18,19,20-pentanor-Δ$^6$-PGI$_1$, |
| (164) | 15-Cyclohexyl-5-iodo-16,17,18,19,20-pentanor Δ$^6$-PGI$_1$, |
| (166) | 5-Chloro-15-cyclohexyl-7-fluoro-16,17,18,19,20-pentanor-Δ$^6$-PGI$_1$, |
| (167) | 5,7-Difluoro-20-methyl-Δ$^6$-PGI$_1$, |
| (168) | 5-Fluoro-20-methyl-Δ$^6$-PGI$_1$, |
| (170) | 5-Chloro-20-methyl-Δ$^6$-PGI$_1$, |
| (172) | 7-Bromo-5-fluoro-20-methyl-Δ$^6$-PGI$_1$, |
| (174) | 5-Fluoro-15-methyl-Δ$^6$-PGI$_1$, |
| (176) | 5-Chloro-15-methyl-Δ$^6$-PGI$_1$, |
| (178) | 5-Fluoro-7-iodo-15-methyl-Δ$^6$-PGI$_1$, |
| (180) | 5-Fluoro-16,16-dimethyl-Δ$^6$-PGI$_1$, |
| (182) | 5-Chloro-16,16-dimethyl-Δ$^6$-PGI$_1$, |
| (183) | 5-Bromo-16,16-dimethyl-Δ$^6$-PGI$_1$, |
| (184) | 5-Chloro-7-iodo-16,16-dimethyl-Δ$^6$-PGI$_1$, |
| (186) | 16-Cyclohexyl-5,7-difluoro-17,18,19,20-tetranor-Δ$^6$-PGI$_1$, |
| (187) | 5-Fluoro-15-cyclohexyl-16,17,18,19,20-pentanor-Δ$^6$-PGI$_1$, |
| (188) | 15-Cyclopentyl-5,7-dichloro-16,17,18,19,20-pentanor-Δ$^6$-PGI$_1$, |
| (189) | 5-Bromo-15-cyclohexyl-16,17,18,19,20-pentanor-Δ$^6$-PGI$_1$, |
| (190) | 5-Fluoro-16-phenoxy-17,18,19,20-pentanor-Δ$^6$PGI$_1$, |

-continued

| | |
|---|---|
| (192) | 5-Chloro-16-(p-fluorophenoxy)-17,18,19,20-tetranor-$\Delta^6$-PGI$_1$, |
| (194) | 5,7-Difluoro-16-(m-trifluoromethylphenoxy)-17,18,19,20-tetranor-$\Delta^6$-PGI$_1$, |
| (196) | 16-(p-Chlorophenoxy)-5,7-dichloro-17,18,19,20-$\Delta^6$-PGI$_1$, |
| (198) | 5,7-Dibromo-16-(m-methylphenoxy)-17,18,19,20-tetranor-$\Delta^6$-PGI$_1$, |
| (200) | 5-Fluoro-16-phenyl-17,18,19,20-tetranor-$\Delta^6$PGI$_1$, |
| (202) | 5-Chloro-16-(m-fluorophenoxy)-17,18,19,20-tetranor-$\Delta^6$-PGI$_1$, |
| (204) | 5,7-Dichloro-16-(m-trifluoromethylphenyl)-17,18,19,20-tetranor-$\Delta^6$-PGI$_1$, |
| (206) | 5-Bromo-16-(p-chlorophenyl)-7-iodo-17,18,19,20-tetranor-$\Delta^6$-PGI$_1$, |
| (208) | 5-Bromo-16-(o-methylphenyl)-17,18,19,20-tetranor-$\Delta^6$-PGI$_1$, |
| (210) | 5-Fluoro-$\Delta^6$-18-oxa-PGI$_1$, |
| (212) | 5-Chloro-$\Delta^6$-18-oxa-PGI$_1$, |
| (214) | 5,7-Difluoro-$\Delta^6$-17-oxa-PGI$_1$, |
| (216) | 5,7-Dichloro-20-methyl-$\Delta^6$-18-oxa-PGI$_1$, |
| (128) | 7-Chloro-5-iodo-16,16-dimethyl-$\Delta^6$-17-oxa-PGI$_1$, |
| (219) | 5-Fluoro-16,16-dimethyl-$\Delta^6$-PGI$_1$, |
| (220) | Methyl ester of (100), |
| (221) | Methyl ester of (101), |
| (222) | Methyl ester of (102), |
| (223) | Methyl ester of (103), |
| (224) | Methyl ester of (104), |
| (226) | Methyl ester of (106), |
| (228) | Methyl ester of (108), |
| (230) | Methyl ester of (120), |
| (231) | Methyl ester of (145), |
| (232) | Methyl ester of (112), |
| (233) | Methyl ester of (152), |
| (234) | Methyl ester of (114), |
| (235) | Methyl ester of (140), |
| (236) | Methyl ester of (116), |
| (237) | Methyl ester of (156), |
| (238) | Methyl ester of (118), |
| (239) | Methyl ester of (162), |
| (240) | Ethyl ester of (120), |
| (241) | n-Butyl ester of (148), |
| (242) | Ethyl ester of (122), |
| (243) | n-Butyl ester of (182), |
| (244) | Ethyl ester of (124), |
| (245) | Butyl ester of (146), |
| (246) | n-Propyl ester of (126), |
| (247) | n-Butyl ester of (126), |
| (248) | n-Butyl ester of (128), |
| (250) | n-Pentyl ester of (132), |
| (252) | n-Hexyl ester of (134), |
| (254) | Methyl ester of (138), |
| (256) | Methyl ester of (140), |
| (258) | Methyl ester of (144), |
| (259) | Butyl ester of (144), |
| (260) | Ethyl ester of (146), |
| (262) | n-Octyl ester of (150) |
| (264) | Ethyl ester of (152), |
| (266) | Methyl ester of (154), |
| (267) | n-Butyl ester of (130), |
| (268) | n-Decyl ester of (158), |
| (269) | n-Decy ester of (128), |
| (270) | Methyl ester of (160), |
| (271) | n-Decyl ester of (189), |
| (272) | Methyl ester of (162), |
| (273) | Methyl ester of (219), |
| (274) | Phenyl ester of (166), |
| (275) | n-Decyl ester of (187), |
| (276) | Methyl ester of (168), |
| (278) | p-Methylphenyl ester of (170), |
| (280) | p-Fluorophenyl ester of (174), |
| (281) | Methyl ester of (183), |
| (282) | Benzyl ester of (176), |
| (284) | Phenethyl ester of (180), |
| (286) | Methyl ester of (182), |
| (287) | Methyl ester of (210), |
| (288) | 11,15-diacetate of (220), |
| (290) | 11,15-diacetate of (223), |
| (291) | 11,15-diacetate of (226), |
| (292) | 11,15-diacetate of (281), |
| (294) | 11,15-diacetate of (224), |
| (296) | 11,15-diacetate of (243), |
| (298) | 11,15-diacetate of (224), |
| (300) | 11,15-diacetate of (281), |
| (302) | 11,15-diacetate of (271), |
| (303) | 11,15-diacetate of (273), |
| (304) | 11,15-diacetate of (275), |
| (306) | 11,15-diacetate of (267), |
| (308) | 11,15-diacetate of (220), |
| (308) | 11,15-bis(t-butyldimethylsilyl)ether of (222), |
| (310) | 11,15-bis(t-butyldimethylsilyl)ether of (239), |
| (312) | 11,15-bis(t-butyldiphenylsilyl)ether of (237), |
| (314) | 11,15-bis(t-butyldimethylsilyl)ether of (269), |
| (315) | 11,15-bis(t-butyldimethylsilyl)ether of (266), |
| (316) | 11,15-bis(t-butyldimethylsilyl)ether of (235), |
| (317) | 11,15-bis(t-butyldimethylsilyl)ether of (241), |
| (318) | 11,15-bis(t-butyldimethylsilyl)ether of (220), |
| (320) | 11,15-bis(t-butyldimethylsilyl)ether of (224), |
| (321) | 11,15-bis(t-butyldimethylsilyl)ether of (259), |
| (322) | Sodium salt of (102), |
| (324) | Sodium salt of (153), |
| (326) | Sodium salt of (152), |
| (328) | Sodium salt of (126), |
| (340) | Sodium salt of (187), |
| (342) | Sodium salt of (101), |
| (344) | Sodium salt of (145), |
| (346) | Sodium salt of (219), |
| (348) | Sodium salt of (100), |
| (350) | Potassium salt of (103), |
| (352) | Sodium salt of (108), |
| (354) | Sodium salt of (110), |
| (356) | Calcium salt of (116), |
| (358) | Magnesium salt of (122), |

Compounds of formula (A$_2$):

(500) 5-Chloro-PGI$_2$,
(501) 7-Fluoro-PGI$_2$,
(502) 5-Bromo-PGI$_2$,
(503) 7-Chloro-PGI$_2$,
(504) 5-Iodo-PGI$_2$,
(505) 7-Bromo-PGI$_2$,
(506) 5,7-Difluoro-PGI$_2$,
(508) 5,7-Dichloro-PGI$_2$,
(510) 5,7-Dibromo-PGI$_2$,
(511) 7-Bromo-5-fluoro-PGI$_2$,
(512) 5,7-Diiodo-PGI$_2$,
(513) 5-Chloro-7-iodo-PGI$_2$,
(514) 5-Chloro-7-fluoro-PGI$_2$,
(515) 5-Bromo-7-chloro-PGI$_2$,
(516) 7-Chloro-5-fluoro-PGI$_2$,
(517) 7-Chloro-5-iodo-PGI$_2$,
(518) 5-Bromo-7-fluoro-PGI$_2$,
(519) 7-Bromo-5-chloro-PGI$_2$,
(520) 5-Chloro-13,14-dehydro-PGI$_2$,
(521) 5-Chloro-13,14-dehydro-PGI$_2$,
(522) 5,7-Dichloro-13,14-dehydro-PGI$_2$,
(523) 7-Fluoro-13,14-dehydro-PGI$_2$,
(524) 5,7-Difluoro-13,14-dehydro-PGI$_2$,
(525) 5-Bromo-7-fluoro-13,14-dehydro-PGI$_2$,
(526) 5-Chloro-13,14-dihydro-PGI$_2$,
(527) 7-Fluoro-5-iodo-13,14-dihydro-PGI$_2$,
(528) 5,7-Difluoro-13,14-dihydro-PGI$_2$,
(529) 7-Fluoro-13,14-dihydro-PGI$_2$,
(530) 5-Chloro-15-methyl-PGI$_2$,
(531) 7-Fluoro-15-methyl-PGI$_2$,
(532) 5,7-Difluoro-15-methyl-PGI$_2$,
(533) 5-Chloro-7-fluoro-13,14-dehydro-PGI$_2$,
(534) 5-Chloro-7-fluoro-15-methyl-PGI$_2$,
(535) 5-Chloro-17(S),20-dimethyl-PGI$_2$,
(536) 5-Chloro-15-methyl-13,14-dihydro-PGI$_2$,
(537) 7-Fluoro-17(S),20-dimethyl-PGI$_2$,
(538) 7-Chloro-5-fluoro-17(R),20-dimethyl-PGI$_2$,
(539) 7-Fluoro-17(R),20-dimethyl-PGI$_2$,
(540) 5-Bromo-7-fluoro-17(S),20-dimethyl-PGI$_2$,
(541) 7-Chloro-5-fluoro-17(S),20-dimethyl-PGI$_2$,
(542) 5-Chloro-16,16-dimethyl-PGI$_2$,
(543) 5-Chloro-17(R),20-dimethyl-PGI$_2$,
(544) 5,7-Difluoro-16,16-dimethyl-PGI$_2$,
(545) 5-Chloro-16,16-dimethyl-PGI$_2$,
(546) 5-Chloro-7-fluoro-16,16-dimethyl-PGI$_2$,
(547) 7-Fluoro-16,16-dimethyl-PGI$_2$,
(548) 15-Cyclohexyl-5-chloro-16,17,18,19,20-pentanor-PGI$_2$, (549) 7-Fluoro-15-cyclohexyl-16,17,18,19,20-pentanor-PGI₂,
(550) 5,7-Difluoro-15-cyclohexyl-16,17,18,19,20-pentanor-PGI₂,
(552) 5-Fluoro-7-bromo-15-cyclohexyl-16,17,18,19,20-pentanor-PGI₂,
(554) 5-Chloro-16-cyclohexyl-17,18,19,20-tetranor-PGI₂,
(555) 5-Chloro-16-cyclohexyl-7-fluoro-17,18,19,20-tetranor-PGI₂,
(556) 5,7-Difluoro-16-cyclohexyl-17,18,19,20-tetranor-PGI₂,
(558) 5,7-Difluoro-16-phenoxy-17,18,19,20-PGI₂,
(560) 5-Bromo-16-phenyl-17,18,19,20-tetranor-PGI₂,
(562) 5,7-Dichloro-16-phenyl-17,18,19,20-tetranor-PGI₂,
(564) 7-Fluoro-16-phenoxy-17,18,19,20-tetranor-PGI₂,
(566) 7-Fluoro-16-(p-fluorophenoxy)-17,18,19,20-tetranor-PGI₂,
(568) 5,7-Difluoro-16-(m-trifluoromethylphenoxy)-17,18,19,20-tetranor-PGI₂,
(570) 7-Fluoro-16-(m-trifluoromethylphenoxy)-17,18,19,20-tetranor-PGI₂,
(572) 7-Fluoro-16-(p-chlorophenoxy)-17,18,19,20-tetranor-PGI₂,
(574) 5,7-Difluoro-16-(p-chlorophenoxy)-17,18,19,20-tetranor-PGI₂,
(576) 5-Bromo-16-(m-trifluoromethylphenyl)-17,18,19,20-tetranor-PGI₂,
(578) 5,7-Dichloro-16-(p-chlorophenyl)-17,18,19,20-tetranor-PGI₂,
(580) 5-Chloro-16-(o-methylphenyl)-17,18,19,20-tetranor-PGI₂,
(582) 5-Chloro-20-methyl-PGI₂,
(584) 5-Bromo-20-methyl-PGI₂,
(586) 5-Iodo-20-methyl-PGI₂,
(588) 5,7-Difluoro-20-methyl-PGI₂,
(590) 7-Fluoro-17-oxa-PGI₂,
(592) 5,7-Difluoro-17-oxa-PGI₂,
(594) 5-Chloro-17-Oxa-PGI₂,
(596) 5-Bromo-7-fluoro-17-oxa-PGI₂,
(598) 7-Fluoro-5-iodo-18-oxa-PGI₂,
(600) 5,7-Difluoro-18-oxa-PGI₂,
(602) 7-Bromo-5-chloro-18-oxa-PGI₂,
(604) 5,7-Dichloro-18-oxa-PGI₂,
(606) 5,7-Dichloro-20-methyl-18-oxa-PGI₂,
(608) 5,7-Difluoro-20-methyl-18-oxa-PGI₂,
(610) 5-Bromo-20-methyl-18-oxa-PGI₂,
(612) 5-Chloro-20-methyl-18-oxa-PGI 2,
(614) 7-Fluoro-16,16-dimethyl-17-oxa-PGI₂,
(616) 5,7-Difluoro-16,16-dimethyl-17-oxa-PGI₂,
(618) 5-Bromo-7-fluoro-16,16-dimethyl-17-oxa-PGI₂,
(620) 7-Fluoro-20-methyl-PGI₂,
(622) 5-Bromo-7-fluoro-20-methyl-PGI₂,
(624) 5-Chloro-7-fluoro-20-methyl-PGI₂,
(626) 7-Fluoro-16,16-dimethyl-PGI₂,
(628) 5-Bromo-7-fluoro-16,16-dimethyl-PGI₂,
(630) 5-Chloro-7-bromo-16,16-dimethyl-PGI₂,
(632) 5,7-Difluoro-16,16-dimethyl-PGI₂,
(634) 5,7-Dibromo-16,16-dimethyl-PGI₂,
(635) Methyl ester of (547),
(636) Methyl ester of (500),
(637) Methyl ester of (501),
(638) Methyl ester of (502),
(639) Methyl ester of (503),
(640) Methyl ester of (506),
(641) Methyl ester of (548),
(642) Methyl ester of (508),
(643) Methyl ester of (526),
(644) Methyl ester of (518),
(645) Metlyl ester of (530),
(646) Ethyl ester of (522),
(647) Methyl ester of (505)
(648) Ethyl ester of (526),
(649) Methyl ester of (508),
(650) Ethyl ester of (530),
(651) Methyl ester of (547),
(652) Propyl ester of (500),
(654) Propyl ester of (502),
(655) Methyl ester of (537),
(656) Propyl ester of (506),
(657) Methyl ester of (535),
(658) Propyl ester of (510),
(660) Butyl ester of (500),
(661) n-Butyl ester of (545),
(662) Butyl ester of (501),
(664) Butyl ester of (510),
(665) n-Butyl ester of (523),
(666) Butyl ester of (516),
(667) Butyl ester of (543),
(668) Pentyl ester of (514),
(670) Pentyl ester of (520),
(671) Methyl ester of (516),
(672) Pentyl ester of (522),
(673) Methyl ester of (511),
(674) Octyl ester of (526),
(675) Methyl ester of (519),
(676) n-Decyl ester of (530),
(677) n-Decyl ester of (520),
(628) Phenyl ester of (538),
(679) n-Decyl ester of (549),
(680) p-Methylphenyl ester of (540),
(681) n-Butyl ester of (539),
(682) p-Methylphenyl ester of (552),
(683) Methyl ester of (515),
(684) p-Fluorophenylester of (554),
(686) Sodium salt of (500),
(687) Sodium salt of (516),
(688) Sodium salt of (501),
(689) Sodium salt of (502),
(690) Sodium salt of (504),
(691) Sodium salt of (537),
(692) Sodium salt of (508),
(693) Sodium salt of (523),
(694) Sodium salt of (521),
(695) Sodium salt of (549),
(696) Sodium salt of (529),
(697) Sodium salt of (547),
(698) Sodium salt of (539),
(699) Sodium salt of (548),
(700) Potassium salt of (500),
(701) Sodium salt of (535),
(702) Potassium salt of (501),
(703) Sodium salt of (530),
(704) Potassium salt of (502),
(705) Sodium salt of (506),
(706) Potassium salt of (501),
(708) Ammonium salt of (500),
(710) Ammonium salt of (501),
(712) Ammonium salt of (554),
(714) Ammonium salt of (556),
(716) Ammonium salt of (566),
(718) Ethanol ammonium salt of (500),
(720) Ethanol ammonium salt of (501),
(722) 11,15-bis(t-butyldimethylsilyl)ether of (500),
(724) 11,15-bis(t-butyldimethylsilyl)ether of (501),
(726) 11,15-bis(t-butyldimethylsilyl)ether of (506),
(728) 11,15-bis(t-butyldimethylsilyl)ether of (582),
(730) 11,15-bis(t-butyldimethylsilyl)ether of (590),
(732) 11,15-bis(2-tetrahydropyranyl)ether of (500),
(734) 11,15-bis(2-tetrahydropyranyl)ether of (582),
(736) 11,15-bis(2-tetrahydropyranyl)ether of (598),
(738) 11,15-bis(2-tetrahydropyranyl)ether of (616),
(740) 11,15-diacetate of (636),
(742) 11,15-diacetate of (639),
(743) 11,15-diacetate of (640),
(744) 11,15-diacetate of (645),
(745) 11,15-diacetate of (683),
(746) 11,15-bis(t-butyldiphenylsilyl)ether of (667),
(748) 11,15-bis(t-butylmethylsilyl)ether of (677),
(750) 11,15-bis(t-butyldimethylsilyl)ether of (647),
(752) 11,15-bis(t-butyldimethylsilyl)ether of (636),
(754) 11,15-diacetate of (679),
(756) 11,15-diacetate of (637),
(757) 11,15-diacetate of (673)
(758) 11,15-bis(t-butyldimethylsilyl)ether of (637),
(760) 11,15-bis(t-butyldimethylsilyl)ether of (638),
(762) 11,15-bis(t-butyldimethylsilyl)ether of (642),
(763) 11,15-bis(t-butyldimethylsilyl)ether of (657),
(764) 11,15-diacetate of (651),
(766) 11,15-bis(t-butyldimethylsilyl)ether of (681),
(768) 11,15-diacetate of (671),
(770) 11,15-diacetate of (675).

The processes for producing the halogenated prostacyclins of the invention are described below in detail.

A group of compounds of general formula (A₁) or (A₂) in which $R^2$ and $R^3$ represent a hydrogen atom or a halogen atom other than a fluorine atom and at least either one of them is a halogen atom other than fluorine can be produced in accordance with Reaction Schemes 1 and 2 below.

Reaction Scheme 1

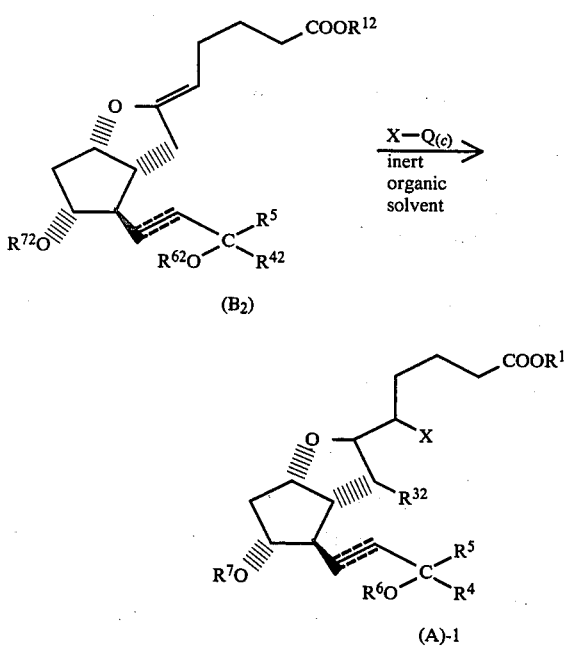

(B₂)

(A)-1

Reaction Scheme 2

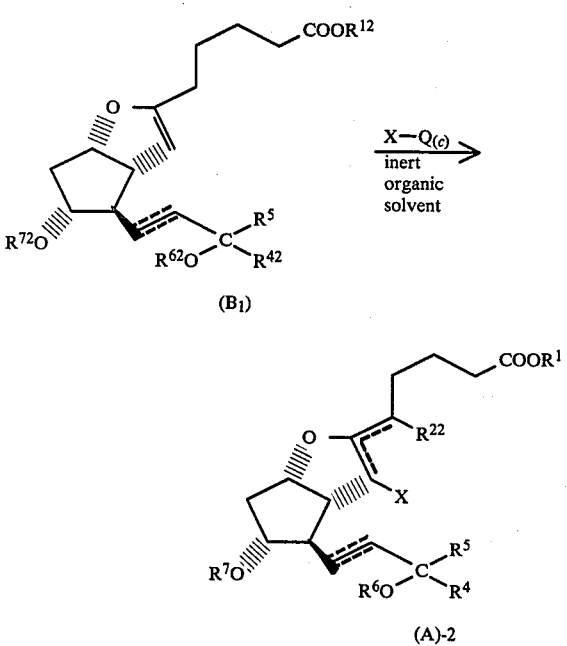

(B₁)

(A)-2

In the reaction Scheme 1, the PGI₂ of general formula (B₂) is halogenated with an electrophilic halogenating agent of general formula (C) in an inert organic solvent, if required in the presence of a basic compound. The reaction product, if required, is then subjected to a reaction of removing the protective group and/or a salt-forming reaction to give the halogenated prostacyclins of general formula (A)-1.

In formula (B₂) representing the PGI₂ (starting material), the symbol ≡≡≡≡≡ between the 13- and 14-positions and $R^5$ are as defined in formula (A₁). The definitions of $R^{12}$, $R^{42}$, $R^{62}$ and $R^{72}$ are encompassed within the definitions of $R^1$, $R^4$, $R^6$ and $R^7$ as follows:

$R^{12}$ represents a $C_1$-$C_{10}$ alkyl group, a substituted or unsubstituted phenyl group, a substituted or unsubstituted alicyclic group or a substituted or unsubstituted phenyl($C_1$-$C_2$)alkyl group;

$R^{42}$ represents a hydrogen atom, a methyl group, or a protected ethynyl group; and $R^{62}$ and $R^{72}$ are identical or different, and each represents a $C_2$-$C_7$ acyl group, a tri($C_1$-$C_7$)-hydrocarbonsilyl group or a group forming an acetal linkage together with the oxygen atom of the hydroxyl group.

The PGI₂ compounds of formula (B₂) can be produced from prostaglandins $F_{2\alpha}$ by known methods (see Japanese Laid-Open Patent Publication No. 95644/1977). Specific examples of such PGI₂ compounds are tabulated below.

| ≡bond | $R^{12}$ | $R^{42}$ | $R^5$ | $R^{62}$ | $R^{72}$ |
|---|---|---|---|---|---|
| double | CH₃ | H | C₅H₁₁ | TBDMSi | TBDMSi |
| " | CH₃ | H | C₅H₁₁ | THP | THP |
| " | CH₃ | H | C₅H₁₁ | CH₃CO | CH₃CO |
| " | C₂H₅ | H | C₅H₁₁ | TBDMSi | TBDMSi |
| " | C₁₀H₂₁ | H | C₅H₁₁ | TBDMSi | TBDMSi |
| " | C₅H₁₁ | CH₃ | C₅H₁₁ | TBDMSi | TBDMSi |
| " | C₂H₅ | H | 2-methyl-1-hexyl | TBDMSi | TBDMSi |
| " | CH₃ | H | cyclohexyl | TBDMSi | TBDMSi |
| triple | CH₃ | H | C₅H₁₁ | CH₃CO | CH₃CO |
| single | CH₃ | H | C₅H₁₁ | CH₃CO | CH₃CO |

In formula (C) representing the electrophilic halogenating agent, X represents a chlorine, bromine or iodine atom, and Q is a nucleophilic residue.

Examples of preferred electrophilic halogenating agents include chlorine, bromine, iodine, N-bromosuccinimide, N-chlorosuccinimide, N-iodosuccinimide, N-bromophthalimide, N-chlorophthalimide, dioxane dibromide, dichlorohydantoin, dibromodimethylhydrantoin, trichloroisocyanuric acid, t-butyl hypochlorite, t-butyl hypobromite, and pyridinium hydrobromide perbromide.

The reaction between the compounds (B₂) and (C) is carried out in an inert organic solvent, if required in the presence of a basic compound.

Examples of the inert organic solvent are halogenated hydrocarbons such as dichloromethane, chloroform, carbon tetrachloride and 1,2-dichloroethane; ethers such as diethyl ether, tetrahydrofuran and dioxane; aromatic hydrocarbons such as benzene, toluene, xylene and pyridine; aliphatic hydrocarbons such as hexane, pentane and cyclohexane; esters such as ethyl acetate; and aprotic polar solvents such ad dimethyl formamide, dimethyl sulfoxide and hexamethylphosphoramide.

The PGI₂ of formula (B₂) is unstable in that its vinyl ether linkage is susceptible to hydrolysis under neutral to acidic conditions. Hence, it is preferable to carry out the above reaction in the presence of a basic compound such as triethylamine, pyridine, sodium or potassium hydrogen carbonate or sodium or potassium carbonate.

The reaction temperature is from −100° C. to +100° C., preferably from −80° C. to +80° C. The reaction time varies depending upon the reaction temperature, the amounts of the reagent and the solvent used, etc. Usually, it is about 0.1 to about 48 hours, preferably 0.1 to 20 hours.

When 0.9 to 1.5 moles of the electrophilic halogenating agent (C) is used per mole of the PGI$_2$ of formula (B$_2$) in the above halogenating reaction, a compound of formula (A)-1 in which R$^{32}$ is a hydrogen atom (a double bond exists between the 6- and 7-positions) is formed as a main product. When the electrophilic halogenating agent (C) is used in an amount of 1.8 to 5 moles, preferably 2 to 3 moles, per mole of the PGI$_2$ of formula (B$_2$), a compound of formula (A)-1 in which R$^{32}$ is X (X and R$_{32}$ are the same halogen atoms, and a double bond exists between the 5- and 6-positions) is formed as a main product.

The desired reaction product can be separated from the resulting reaction mixture by washing the reaction mixture with an aqueous solution of sodium carbonate or the like to separate the organic layer when the reaction solvent is water-insoluble, or by concentrating the reaction mixture, adding an aqueous solution of sodium hydrogen carbonate and a water-insoluble solvent, to perform washing and extraction and separating the organic layer. The resulting organic layer is dried and concentrated to obtain the desired product.

The desired product can be purified by various purifying means such as silica gel column chromatography, silica gel thin-layer chromatography, Florisil column chromatography, and high-performance liquid chromatography. Such purifying means can also be applied directly to the reaction mixture as obtained.

Sometimes, about 0.01 to about 1% of a base such as triethylamine may be added to the developing solvent used in the purifying step.

The product obtained by the halogenation may then be subjected, if required, to a reaction of removing the protective group and/or a salt-forming reaction.

The deprotecting reaction may be carried out on the reaction mixture as obtained by the halogenation, or on the separated and purified desired product obtained as above.

When the protective group (R$^{62}$ and/or R$^{72}$) for the hydroxyl group is a group forming an acetal linkage together with the oxygen atom of the hydroxyl group, the protecting reaction is conveniently carried out in water, tetrahydrofuran, diethyl ether, dioxane, acetone, acetonitrile, etc. as a reaction solvent using acetic acid, a pyridinium salt of p-toluenesulfonic acid, a cation-exchange resin, etc. as a catalyst. The reaction is carried out at a temperature in the range of from −78° C. to +30° C. for about 10 minutes to about 3 days. When the protective group is a tri(C$_1$-C$_7$)hydrocarbon-silyl group, the deprotecting reaction is carried out at the same temperature for the same period of time as described above in the same reaction solvent as described above (preferably other than water) in the presence of acetic acid, tetrabutyl ammonium fluoride, cesium fluoride, etc., preferably the last two, more preferably in the presence of a basic compound such as trimethylamine. When the protective group is an acyl group, the deprotecting reaction can be carried out by performing hydrolysis in an aqueous solution of sodium hydroxide, potassium hydroxide, calcium hydroxide, etc., a water-alcohol mixed solution, or a methanol or ethanol solution containing sodium methoxide, potassium methoxide, sodium ethoxide, etc.

The protective group (R$^{12}$) for the carboxyl group may be removed by using an enzyme such as lipase in water or a water-containing solvent at a temperature of from −10° C. to +60° C. for a period of from about 10 minutes to about 24 hours.

According to this invention, the compound having a carboxyl group resulting from the above deprotecting reaction may, if required, be subjected to a salt-forming reaction to form the corresponding carboxylate salt. The salt-forming reaction is known per se, and can be carried out by neutralizing the carboxylic acid with a nearly equivalent amount of a basic compound such as sodium hydroxide, potassium hydroxide, sodium carbonate, ammonia, trimethylamine, monoethanolamine, or morpholine in a usual manner.

Thus, three are obtained halogenated prostacyclins of the following formula

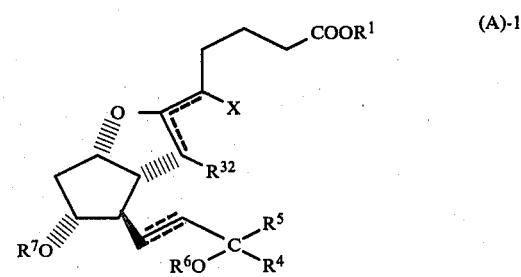

(A)-1 wherein
the symbol ========= between the 5-, 6- and 7-positions indicates that a double bond exists either between the 5- and 6-positions or between the 6- and 7-positions; the symbyl ========= between the 13- and 14-positions, R$^1$, R$^4$, R$^5$, R$^6$ and R$^7$ are as defined with regard to formula (A$_1$); R$^{32}$ represents a hydrogen, chlorine, bromine or iodine atom; X is as defined with regard to formula (C); and when R$^{32}$ is a hydrogen atom, a double bond exists between the 6- and 7-positions and when R$^{32}$ is other than hydrogen, a double bond exists between the 5- and 6-positions, as shown by Reaction Scheme 1.

According to the reaction of Reaction Scheme 1, both mono- and di-halogenated prostacyclins (monohalogenated PGI$_1$ and dihalogenated PGI$_2$) can be produced by controlling the amount of the electrophilic halogenating agent (C). The two halogen atoms in the dihalogenated PGI$_2$ are the same.

In Reaction Scheme 2, the PGI$_1$ of general formula (B$_1$) is reacted with the electrophilic halogenating agent of general formula (C) in quite the same way as in Reaction Scheme 1 to give the halogenated prostacyclins of general formula (A)-2.

The starting PGI$_1$ of formula (B$_1$) can be produced from PGI$_2$ or 6-keto PGF$_{1\alpha}$ by known methods [R. A. Jhonson et al., J. Amer. Chem. Soc. 100, 7690 (1978)].

Specific examples of PGI$_1$ will become apparent from the specific examples given above of PGI$_2$.

Thus, according to Reaction Scheme 2, there are formed halogenated prostacyclins of the following formula

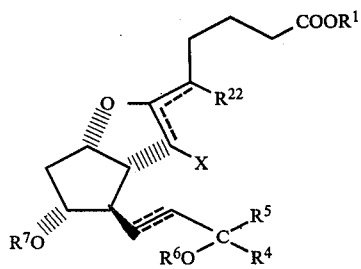

(A)-2 wherein
the symbol ======= between the 5-, 6- and 7-positions, the symbol ======= between the 13- and 14-positions, $R^1$, $R^4$, $R^5$, $R^6$, $R^7$ and X are as defined with regard to formula ($A_1$); and $R^{22}$ represents a hydrogen, chlorine, bromine or iodine atom, provided that when $R^{22}$ is a hydrogen atom, a double bond exists between the 5- and 6-positions, and when $R^{22}$ is other than hydrogen, a double bond exists between the 6- and 7-positions.

The reaction in accordance with the Reaction Scheme 2 can also afford both mono- and dihalogenated prostacyclins (monohalogenated $PGI_2$ and dihalogenated $PGI_1$). The two halogen atoms in the dihalogenated $PGI_1$ are the same.

A group of halogenated prostacyclins of the invention in which $R^2$ and $R^3$ represent a hydrogen atom or a halogen atom other than fluorine and at least one of them is a halogen atom other than fluorine can be produced as dihalogenated $PGI_2$ of formula $(A_2)$-$a_1$ and monohalogenated $PGI_2$ of formula $(A_2)$-$a_2$ in accordance with Reaction Schemes 3 and 4 below from the monohalogenated $PGI_1$ of formula $(A_1)$-a obtained in accordance with the Reaction Scheme 1. Or they may be produced as dihalogenated $PGI_1$ of formula $(A_1)$-$a_1$ and monohalogenated $PGI_1$ of formula $(A_1)$-$a_2$ in accordance with Reaction Schemes 5 and 6 below from the monohalogenated $PGI_2$ of formula $(A_2)$-a obtained in accordance with the Reaction Scheme 2.

Reaction Scheme 3

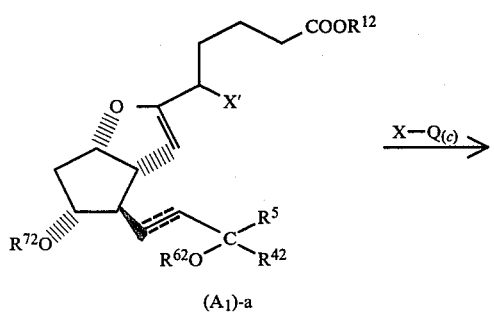

($A_1$)-a

-continued
Reaction Scheme 3

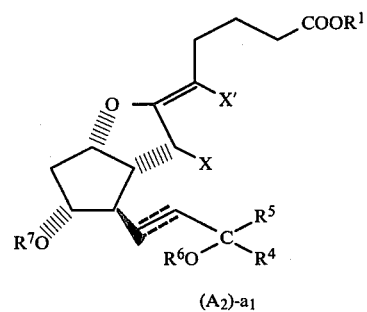

($A_2$)-$a_1$

In the above scheme, X′ represents a chlorine, bromine or iodine atom (the same definition applies hereinafter).

Reaction Scheme 4

($A_1$)-a $\xrightarrow{H^+}$ 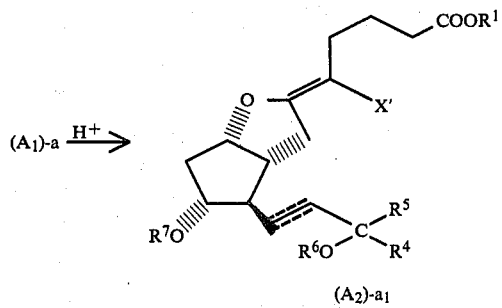

($A_2$)-$a_1$

Reaction Scheme 5

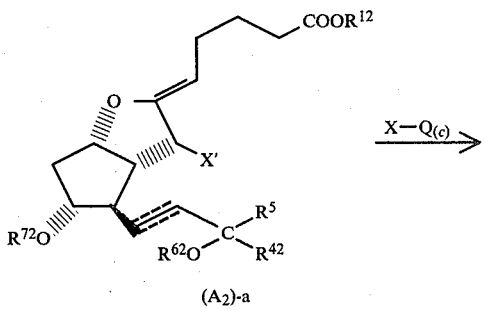

($A_2$)-a $\xrightarrow{X-Q_{(c)}}$

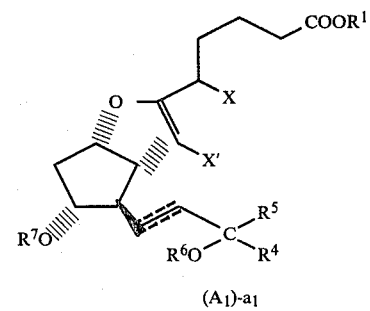

($A_1$)-$a_1$

Reaction Scheme 6

-continued

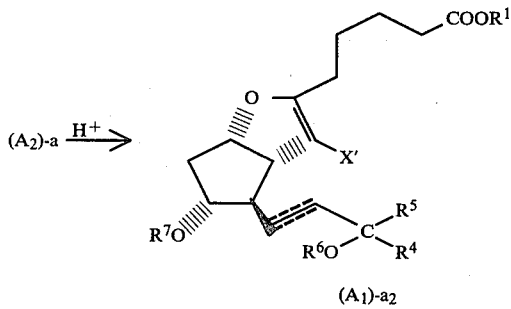

(A₁)-a₂

The reactions in the Reaction Schemes 3 and 5 can be carried out in the same way as in Reaction Scheme 1.

The reaction in Reaction Scheme 4 is carried out by treating the monohalogenated PGI₁ of formula (A₁)-a in a solvent in which a proton exists to isomerize the double bond at the 6-position to a double bond at the 5-position, and then if required, subjecting the product to a reaction of removing the protective group and/or a salt-forming reaction. The product is the monohalogenated PGI₂ of formula (A₂)-a₂.

The above isomerization reaction is carried out by
(a) treating the monohalogenated PGI₁ of formula (A₁)-a with a catalytic amount of a protic acid or a pyridinium salt of an organic sulfonic acid in an inert aprotic solvent, if required while causing a dehydrating agent to be present subsequently or simultaneously, or (b) treating the aforesaid compound with a catalytic amount of a protic acid in a protic solvent, and then heating the product in an aprotic solvent.

Examples of the inert aprotic solvent used in the procedure (a) are benzene, toluene, xylene, chlorobenzene, hexane, pentane, cyclohexane, methylene chloride, chloroform, carbon tetrachloride, 1,2-dichloroethane, diethyl ether, tetrahydrofuran, dioxane, dimethoxyethane, dimethyl sulfoxide, dimethyl formamide, and mixtures of these.

Examples of the catalyst are mineral acids such as sulfuric acid, hydrochloric acid, hydrobromic acid, and perchloric acid, organic sulfonic acids such as p-toluenesulfonic acid, trifluoroacetic acid, methanesulfonic acid and trifluoromethanesulfonic acid, and salts of organic sulfonic acids such as pyridinium p-toluenesulfonate. Sulfuric acid is especially suitable.

The treating temperature is from −120° C. to +100° C., preferably from −20° C. to +90° C. The treating time varies depending upon the treating temperature, the catalyst used, etc. Usually, it is several seconds to about 24 hours, preferably from 30 seconds to about 1 hour.

The treatment may, if desired be carried out while causing a dehydrating agent to be present subsequently or simultaneously. Specifically, the product treated with a protic acid or a pyridinium salt of an organic sulfonic acid is then treated with a dehydrating agent such as magnesium sulfate, dihydrofuran or dihydropyran; or the treatment with the protic acid or the pyridinium salt of organic sulfonic acid is carried out in the presence of the dehydrating agent.

In the procedure (b), the protic solvent may preferably be ethanol, methanol, isopropanol, etc. The treatment with the protic acid is carried out at −70° C. to +100° C., preferably −20° C. to +50° C. The treating time is usually 1 minute to 24 hours, preferably 10 minutes to 2 hours. After this treatment, the reaction product is heated in an aprotic solvent. Preferably, this heating is carried out on the separated reaction product.

Suitable aprotic solvents are those exemplified above in regard to the procedure (a), and aprotic polar solvents such as hexamethylphosphoramide are preferred. The heating is carried out usually at 60° to 200° C., preferably 120° to 180° C., and the reaction time is usually 5 minutes to 24 hours.

The separation of the desired product from the resulting reaction mixture and its purification can be carried out in the same way as described above with regard to Reaction Scheme 1.

Thus, the Reaction Scheme 4 gives monohalogenated PGI₂ of formula (A₂)-a₂. The resulting monohalogenated PGI₂ compounds differ from the starting monohalogenated PGI₁ compounds in the position of the double bond.

The reaction in accordance with Reaction Scheme 6 is carried out by treating the monohalogenated PGI₂ of formula (A₂)-a in a solvent in which a proton exists to isomerize the double bond at the 5-position to a double bond at the 6-position and then if required, subjecting the product to a reaction of removing the protective group and/or a salt-forming reaction. The isomerization reaction can be carried out in the same way as in the procedure (a) or (b) in the reaction of Reaction Scheme 4.

The resulting compound is a monohalogenated PGI₁ of formula (A₁)-a₂ which differs from the starting monohalogenated PGI₂ in the position of the double bond.

It will thus be seen that according to Reaction Schemes 1 to 6, mono- or di-halogenated PGI₁ compounds and mono- or di-halogenated PGI₂ compounds of formula (A₁) and (A₂) respectively in which R² and R³ are identical or different and each represents a hydrogen atom or a halogen atom other than fluorine (provided that R² and R³ are not hydrogen atoms at the same time) can be produced. A group of halogenated prostacyclins of the invention represented by general formula (A₁) or (A₂) in which at least one of R² and R³ is a fluorine atom can be produced in accordance with Reaction Schemes 7 to 12 given below.

Reaction Scheme 7

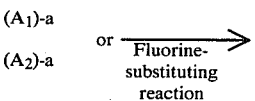

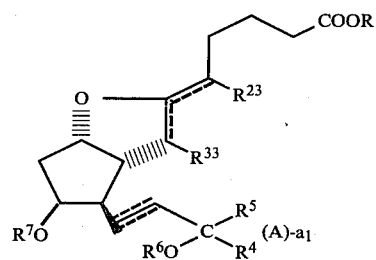

According to Reaction Scheme 7, monofluorinated prostacyclins of formula (A)-a₁ are produced. Specifically, 5-fluoro PGI₁ compounds and 7-fluoro PGI₂ compounds [compounds of formula (A)-a₁] are produced whether the starting material is a monohalogenated (i.e., monochlorinated, monobrominated or monoiodinated) PGI$_1$ of formula (A$_1$)-a or a monohalogenated (i.e., monochlorinated, monobrominated or monoiodinated) PGI$_2$ of formula (A$_2$)-a.

The reaction of Reaction Scheme 7 is carried out by fluorinating the monohalogenated PGI$_1$ of formula (A$_1$)-a or mono-halogenated PGI$_2$ of formula (A$_2$)-a with a fluorinating agent in an aprotic inert organic solvent and then if required, subjecting the reaction product to a reaction of removing the protective group and/or a salt-forming reaction.

Various fluorinating agents which are used to substitute a fluorine atom for a chlorine, bromine or iodine atom can be used in this reaction. Such fluorinating agents are known per se, and include, for example, silver fluoride, cesium fluoride, potassium fluoride, sodium fluoride, mercury fluoride, mercury borofluoride and tetrabutyl ammonium fluoride. Silver fluoride is preferred.

Examples of the aprotic inert organic solvent are polar solvents such as acetonitrile, dimethyl formamide, dimethyl sulfoxide and hexamethylphosphoric triamide; hydrocarbon solvents such as benzene, toluene and xylene; chlorinated hydrocarbon solvents such as dichloromethane, chloroform and carbon tetrachloride; and ether solvents such as diethyl ether, tetrahydrofuran, and diethylene glycol dimethyl ether. The polar solvents, above all acetonitrile, are preferred. A crown ether such as 18-crown-6 may be used as a dissolving aid for the fluorinating agent.

The fluorinating agent may be used in an amount of 1 to 10 moles per mole of the starting material.

The fluorinating reaction is carried out at a temperature of usually 0° to 200° C., preferably 20° to 160° C. The reaction time is from several minutes to 76 hours, but usually a period of 48 hours is sufficient.

Preferably, the reaction is carried out in the presence of triethylamine, sodium or potassium hydrogen carbonate, or potassium or sodium carbonate in the reaction system.

Preferably, the fluorinating reaction is carried out at 0° to 80° C. for several minutes to 4 hours using silver fluoride as the fluorinating agent.

The separation of the desired product from the reaction mixture and its purification can be carried out in the same way as described hereinabove with regard to Reaction Scheme 1. The resulting desired product may be subjected to a reaction of removing the protective group or a salt-forming reaction in the same way as described hereinabove with regard to Reaction Scheme 1.

Reaction Scheme 8

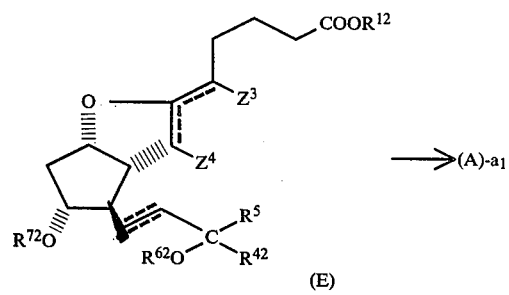

(E)

$\longrightarrow$ (A)-a$_1$

The hydroxyprostacyclins of formula (E) represent either 5-hydroxyl PGI$_1$ or 7-hydroxy PGI$_2$.

According to Reaction Scheme 8, 5-fluoro PGI$_1$ and 7-fluoro PGI$_2$ [compounds of formula (A)-a$_1$] can be produced by using any of these hydroxyprostacyclins.

Reaction Scheme 8 involves reacting the hydroxyprostacyclin with a di(C$_1$–C$_5$)alkylamino-SF$_3$, bis[di(C$_1$–C$_5$)alkylamino]-SF$_2$, morpholino-SF$_3$ or CF$_3$CHF$_2$N(C$_2$H$_5$)$_2$ in an aprotic inert organic solvent in an aprotic inert organic solvent.

Examples of the di(C$_1$–C$_5$)alkylamino-SF$_3$ are dimethylamino-SF$_3$, diethylamino-SF$_3$, dipropylamino-SF$_3$ and dipentylamino-SF$_3$.

Examples of the bis[di(C$_1$–C$_5$)alkylamino]-SF$_2$ are bis(dimethylamino)-SF$_2$, bis(diethylamino)-SF$_2$, bis(dipropylamino)-SF$_2$, bis(dibutylamino)-SF$_2$ and bis(dipentylamino)-SF$_2$.

Examples of the aprotic inert organic solvents include chlorine-containing solvents such as dichloromethane, chloroform, carbon tetrachloride and 1,2-dichloroethane, ethers such as diethyl ether, tetrahydrofuran and dimethoxyethane, and hydrocarbons such as benzene, toluene and xylene. Dichloromethane, and chloroform are preferred.

The fluorinating agent may be used in an amount of 1 to 10 moles per mole of the starting material.

The reaction temperature is −100° C. to +80° C., preferably −70° C. to +30° C. The reaction time varies depending upon the reaction temperature, the amounts of the reagent and solvent used, etc. It is preferably 0.1 to 48 hours, especially preferably 0.5 to 16 hours.

The separation of the desired product from the resulting reaction mixture and its purification can be carried out in the same way as described hereinabove with regard to Reaction Scheme 1. The deprotecting reaction or the salt forming reaction which is optionally carried out on the reaction product can be carried out in the same way as described hereinabove with regard to Reaction Scheme 1.

The hydroxyprostacyclins as starting materials of formula (E) are novel compounds.

Investigations of the present inventors have shown that the hydroxyprostacyclins can be produced from PGI$_2$ or PGI$_1$ compounds in accordance with Reaction Scheme A or B, respectively.

Reaction Scheme A

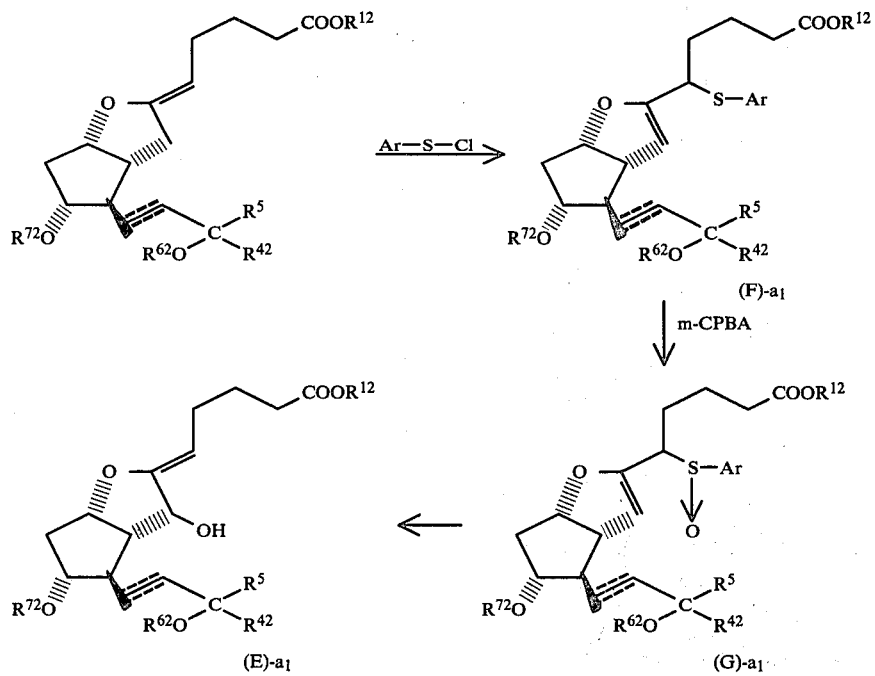

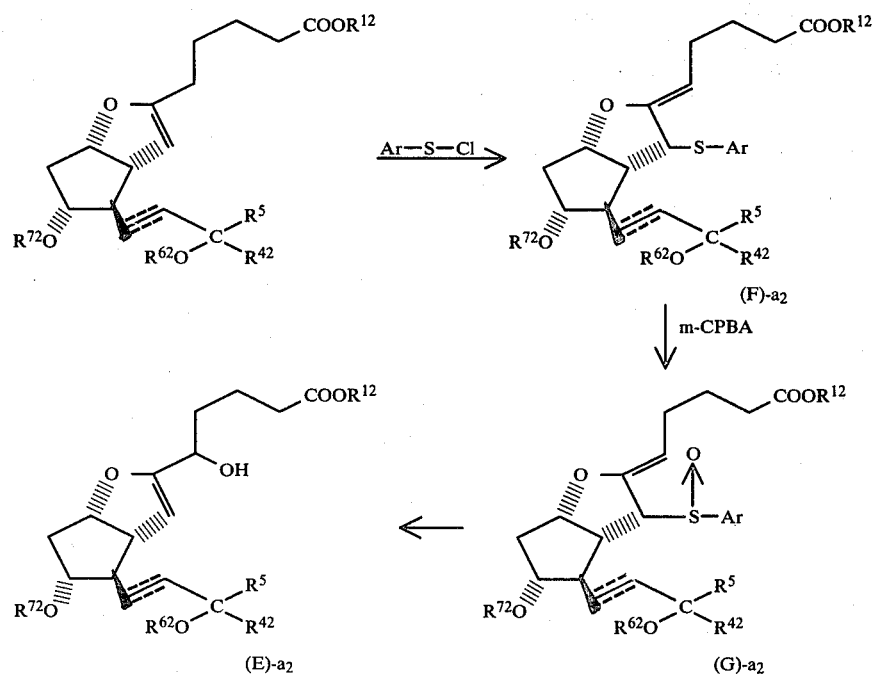

Reaction Scheme B

The starting material PGI$_2$ in Reaction Scheme A is first reacted with an arylsulfonyl chloride (Ar-S-Cl in which Ar is an aryl group such as phenyl or tolyl) in the presence of a basic compound such as triethylamine, pyridine, 4-N,N-dimethylaminopyridine or 2,2,6,6-tetramethylpiperazine in an aprotic inert organic solvent. The reaction is carried out advantageously at −80° C. to +50° C.

The 5-arylsulfenyl-PGI$_1$ of formula (F)-a$_1$ can be isolated from the reaction mixture by the method already described hereinabove.

Then, the 5-arylsulfenyl-PGI$_1$ is reacted with m-chloroperbenzoic acid (m-CPBA) in a two-phase solvent system composed of a water-immiscible organic solvent and an aqueous solution of sodium or potassium hydrogen carbonate.

Examples of suitable water-immiscible organic solvents include dichloromethane, chloroform, carbon tetrachloride, dichloroethane, benzene, toluene, xylene, and ethyl diethyl ether. The reaction can be conveniently carried out at 0° to 50° C.

As a result, the 5-arylsulfinyl-PGI$_1$ of formula (G)-a$_1$ is formed. This product can likewise be isolated from the reaction mixture.

Then, the 5-arylsulfinyl-PGI$_1$ is treated with a thienophilic agent such as diethylamine, hexamethylphosphoric triamide or trimethyl phosphite in the presence of an organic solvent.

The organic solvent is preferably a lower alcohol such as methanol, ethanol or isopropanol, or an ether such as diethyl ether, tetrahydrofuran, dioxane or dimethoxyethane.

The reaction is carried out at $-40°$ C. to $+160°$ C., preferably $0°$ C. to $60°$ C.

The resulting 7-hydroxy PGI$_2$ of formula (E)-a$_1$ formed as above forms part of the hydroxyprostacyclins of formula (E).

According to Reaction Scheme B, 5-hydroxy PGI$_1$ compounds of formula (F)-a$_2$ are produced from the starting PGI$_1$ compounds in the same way as in Reaction Scheme A through 7-oxysulfenyl PGI$_2$ compounds of formula (F)-a$_2$ and 7-arylsulfinyl PGI$_2$ compounds of formula (G)-a$_2$. The 5-hydroxy PGI$_1$ compounds together with the 7-hydroxy PGI$_2$ compounds of formula (E)-a$_1$ form the hydroxyprostacyclins of formula (E).

Examples of the hydroxyprostacyclins of formula (E) are given below.

(800) 7-Hydroxy-PGI$_2$ methyl ester-11,15-bis(t-butyldimethylsilyl)ether, (802) 7-hydroxy-PGI$_2$ ethyl ester-11,15-bis(t-butyldimethylsilyl)ether, dimethylsilyl)ether, (804) 7-hydroxy-PGI$_2$ isopropyl ester-11,15-bis(t-butyldimethylsilyl)ether, (806) 7-hydroxy-PGI$_2$ butyl ester-11,15-bis(2-tetrahydropyranyl)ether, (808) 7-hydroxy-PGI$_2$ hexyl ester-11,15-bis(2-tetrahydropyranyl)ether, (810) 7-hydroxy-PGI$_2$ decyl ester-11,15-bis(t-butyldimethylsilyl)ether, (812) 7-hydroxy-PGI$_2$ methyl ester-11,15-diacetate, (814) 7-hydroxy-13,14-dehydro-PGI$_2$ methyl ester-11,15-bis(t-butylsilyl)ether, (816) 7-hydroxy-13,14-dihydro-PGI$_2$ methyl ester-11,15-bis(t-butyldimethylsilyl)ether, (818) 7-hydroxy-15-methyl-PGI$_2$ ethyl ester-11,15-bis(2-tetrahydropyranyl)ether, (820) 7-hydroxy-17(R),20-dimethyl-PGI$_2$ methyl ester-11,15-bis(t-butyldimethylsilyl)ether, (822) 7-hydroxy-16,16-dimethyl-PGI$_2$ butyl ester-11,15-bis(t-butyldimethylsilyl)ether, (824) 7-hydroxy-16,17,18,19,20-pentanor-15-cyclohexyl-PGI$_2$ methyl ester-11,15-bis(t-butyldimethylsilyl)ether, (826) 7-hydroxy-17,18,19,20-tetranor-16-phenyl-PGI$_2$ methyl ester-11,15-bis(t-butyldimethylsilyl)ether, (828) 5-hydroxy-$\Delta^6$-PGI$_1$ methyl ester-11,15-bis(t-butyldimethylsilyl)ether, (830) 5-hydroxy-$\Delta^6$-PGI$_1$ ethyl ester-11,15-bis(t-butyldimethylsilyl)ether, (832) 5-hydroxy-$\Delta^6$-PGI$_1$ decyl ester-11,15-bis(2-tetrahydropyranyl)ether, (834) 5-hydroxy-13,14-dehydro-$\Delta^6$-PGI$_1$ methyl ester-11,15-bis(t-butyldimethylsilyl)ether, (836) 5-hydroxy-15-methyl-$\Delta^6$-PGI$_1$ ethyl ester-11,15-bis(t-butyldimethylsilyl)ether, (838) 5-hydroxy-17(R),20-dimethyl-$\Delta^6$-PGI$_1$ methyl ester-11,15-diacetate, (840) 5-hydroxy-16,16-dimethyl-$\Delta^6$-PGI$_1$ methyl ester-11,15-bis(t-butyldimethylsilyl)ether, (842) 5-hydroxy-16,17,18,19,20-pentanor-15-cyclohexyl-$\Delta^6$-PGI$_1$ methyl ester-11,15-bis(t-butyldimethylsilyl)ether, (844) 5-hydroxy-17,18,19,20-tetranor-16-(p-fluorophenoxy)-$\Delta^6$-PGI$_1$ methyl ester-11,15-bis(t-butyldimethylsilyl)ether, and (846) 5-hydroxy-17,18,19,20-tetranor-16-(p-trifluoromethylphenoxy)-$\Delta^6$-PGI$_1$ methyl ester-11,15-bis(t-butyldimethylsilyl)ether.

Reaction Scheme 9

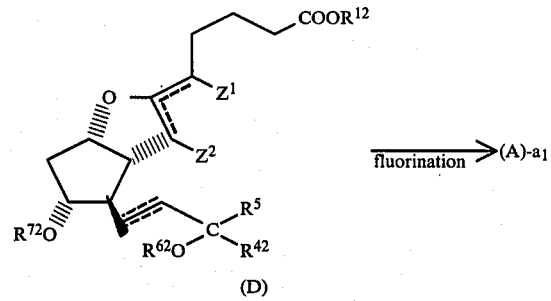

The oxyprostacyclins of formula (D) represent either 5-mesyl(or trifluoromesyl or tosyl)oxy PGI$_1$ or 7-mesyl(or trifluoromesyl or tosyl)oxy PGI$_2$.

According to Reaction Scheme 9, 5-fluoro PGI$_1$ compounds and 7-fluoro PGI$_2$ compounds [compounds of formula (A)-a$_1$] can be produced by using any one of these oxyprostacyclins.

Reaction Scheme 9 involves reacting the oxyprostacyclin with a fluorinating agent in an aprotic inert organic solvent, and then if required, subjecting the resulting product to a reaction of removing the protective group and/or a salt-forming reaction.

The fluorinating agent and the aprotic inert organic solvent may be the same as those described hereinabove with regard to Reaction Scheme 7. The reaction conditions are also the same as in Reaction Scheme 7. The reaction time is Reaction Scheme 9 is 1 to 76 hours, preferably 4 to 48 hours. The separation of the desired product from the reaction mixture and its purification and the deprotecting reaction and/or the salt-forming reaction of the resulting product can be performed by the same methods as described above in regard to Reaction Scheme 1.

The oxyprostacyclins of formula (D) are novel compounds. The 5-oxy PGI$_1$ and 7-oxy PGI$_2$ can be produced by reacting the hydroxy PGI$_1$ of formula (E)-a$_2$ or the hydroxy PGI$_2$ of formula (E)-a$_1$ respectively with phenylsulfonyl chloride, tolylsulfonyl chloride or trifluoromethylsulfonyl chloride. This reaction is carried out in an aprotic inert organic solvent in the presence of a basic compound.

The basis compound is preferably an organic base such as pyridine or triethylamine.

Examples of the aprotic inert organic solvent are chlorine-containing solvents such as dichloromethane, chloroform or carbon tetrachloride; ether solvents such as diethyl ether and tetrahydrofuran, dimethyl formamide, dimethyl sulfoxide and hexamethylphosphoric triamide. Dichloromethane and chloroform are preferred. In one embodiment, an organic base such as pyridine or triethylamine may be used concurrently as a solvent.

The sulfonyl chloride can be used in an amount of 1 to 10 moles per mole of the hydroxyprostacyclin as a starting material.

The reaction temperature is $-100°$ C. to $+100°$ C., preferably $-20°$ C. to $+30°$ C. The reaction time varies depending upon the reaction conditions, but is usually 1 to 48 hours, preferably 2 to 16 hours.

The resulting oxyprostacyclin of formula (D) so obtained can be used as a starting material of the reaction of Reaction Scheme 9 without being isolated from the reaction mixture.

It will be seen that according to Reaction Schemes 7 to 9, 5-fluoro $PGI_1$ compounds [$(A_1)$-$a_3$] and 7-fluoro $PGI_2$ [$(A_2)$-$a_3$] can be produced.

Reaction Scheme 10

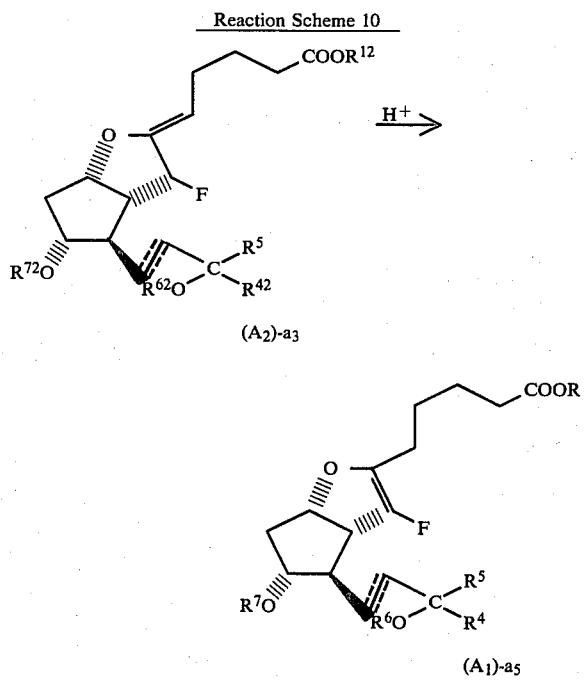

The reaction of Reaction Scheme 10 is carried out in the same way as in Reaction Schemes 4 and 6.

The reaction in accordance with Reaction Scheme 10 gives 7-fluoro $PGI_1$ [$(A_1)$-$a_5$] having a different position of the double bond from the starting 7-fluoro $PGI_2$ of formula $(A_2)$-$a_3$.

Reaction Scheme 11

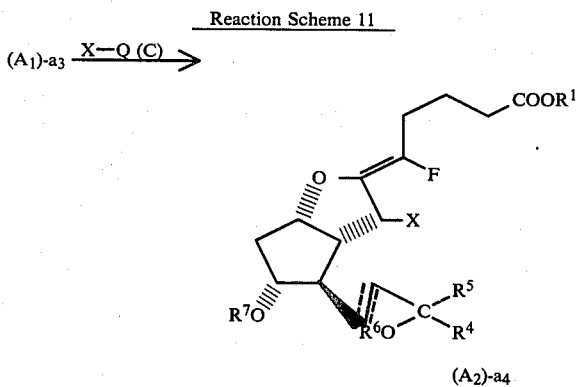

Reaction Scheme 12

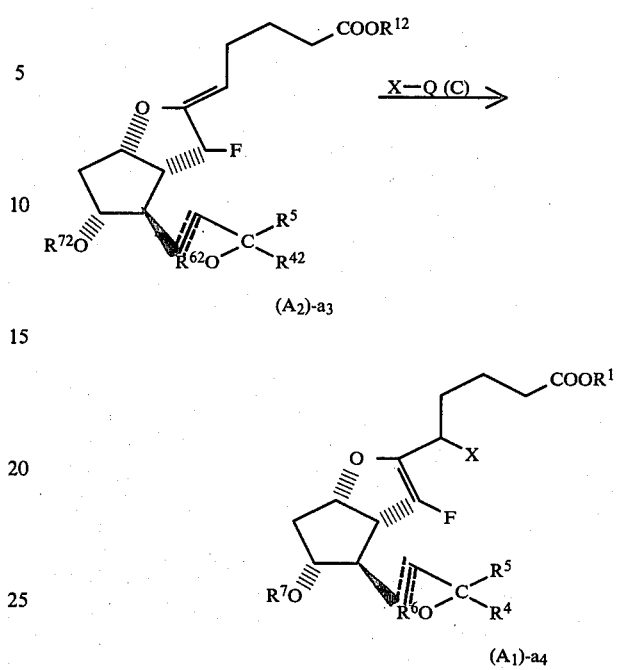

The 5-fluoro $PGI_1$ of formula $(A_1)$-$a_3$ and the 7-fluoro $PGI_2$ of formula $(A_2)$-$a_3$ can be isolated from the reaction mixture obtained by any one of the reactions of Reaction Schemes 7 to 9 and purified by the various chromatographic methods exemplified hereinabove.

The reactions of Reaction Schemes 11 and 12 are carried out by halogenating the starting materials with the electrophilic halogenating agent of formula (C) in an inert organic solvent if required in the presence of a basic compound, and then if required, subjecting the products to a reaction of removing the protective group and/or a salt-forming reaction.

As the electrophilic halogenating agent, the same compounds as exemplified hereinabove with regard to Reaction Scheme 1 can be used. The amount of the halogenating agent is 0.9 to 1.5 moles per mole of the starting material. Preferably, the electrophilic halogenating agent is t-butyl hypochlorite, t-butyl hypobromite or N-iodosuccinimide.

The inert organic solvent and the basic compound may be the same as those described hereinabove with regard to Reaction Scheme 1.

The deprotecting reaction and/or the salt-forming reaction as well as the halogenation reaction can be carried out by the same methods as described hereinabove with regard to Reaction Scheme 1.

According to Reaction Schemes 11 and 12, halogenated prostacyclins of the invention in which one of $R^2$ and $R^3$ is a fluorine atom and the other is a halogen atom other than fluorine can be produced.

Reaction Scheme 13

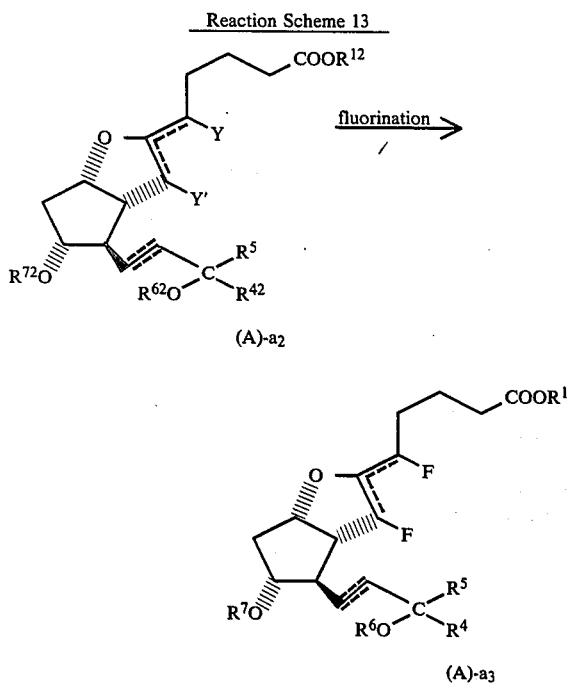

In the formula (A)-a₂, Y and Y' are identical or different and each represents a fluorine, chlorine, bromine or iodine atom, provided that Y and Y' are not fluorine atoms at the same time, and when Y is a fluorine atom a double bond exists between the 5- and 6-positions and when Y' is a fluorine atom, a double bond exists between the 6- and 7-positions.

Accordingly, the halogenated prostacyclins of formula (A)-a₂ are comprised of some of the compounds of formula (A)-1, some of the compounds of formula (A)-2, the compounds of formula (A₂)-a₁, the compounds of formula (A₂)-a₂, the compounds of formula (A₁)-a₁, the compounds of formula (A₁)-a₂, the compounds of formula (A₂)-a₄, and the compounds of formula (A₁)-a₄.

The reaction of Reaction Scheme 13 can be performed in the same way as in the reaction of Reaction Scheme 7.

The reaction of Reaction Scheme 13 gives difluorinated prostacyclins of formula (A)-a₃ having a double bond at the same position as the starting halogenated prostacyclins of formula (A)-a₂. In other words, when the starting material is a halogenated PGI₂, the product is a difluorinated PGI₂, and when the starting material is a halogenated PGI₁, the product is a difluorinated PGI₁.

Thus, according to Reaction Schemes 1 to 13, all of the halogenated prostacyclins of formulae (A₁) and (A₂) provided by this invention can be produced.

It has been found in accordance with this invention that compounds of formula (A₁)-1 and (A₂)-1 have pharmacologically excellent activities, for example an excellent activity of controlling vascular actions.

Thus, the present invention also provides a pharmaceutical composition for controlling vascular actions, comprising (1) as an active ingredient, a halogenated prostacyclin selected from the group consisting of halogenated PGI₁ of the formula

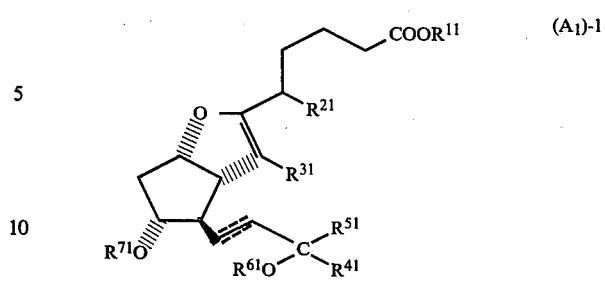

wherein
the symbol ======= between the 13- and 14-positions indicates that a single, double or triple bond exists between the 13- and 14-positions; $R^{11}$ represents a hydrogen atom, a $C_1$–$C_{10}$ alkyl group, or one equivalent of a cation whose salt is pharmaceutically acceptable; $R^{21}$ and $R^{31}$ represent a hydrogen, fluorine or chlorine atom, provided that $R^{21}$ and $R^{31}$ are not hydrogen atoms at the same time; $R^{41}$ represents a hydrogen atom or a methyl group; $R^{51}$ represents an n-pentyl, n-hexyl, 2-methyl-1-hexyl, 2-methyl-2-hexyl or cyclohexyl group; and $R^{61}$ and $R^{71}$ represent a hydrogen atom or an acetyl group, and halogenated PGI₂ of the formula

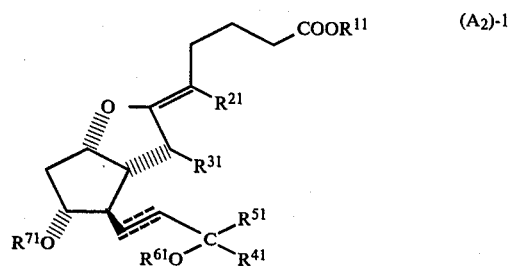

wherein
the symbol ======= between the 13- and 14-positions, $R^{11}$, $R^{21}$, $R^{31}$, $R^{41}$, $R^{51}$, $R^{61}$ and $R^{71}$ are as defined above, provided that when $R^{21}$ is a hydrogen or fluorine atom, $R^{31}$ is not a hydrogen atom, and (2) a pharmaceutically acceptable carrier.

The halogenated prostacyclins of formulae (A₁)-1 and (A₂)-1 are characteristic in that they are more stabilized than natural PGI₂ and have biological activities nearly comparable to natural PGI₂ and better selective activity than natural PGI₂.

The active compound of the invention can be administered orally or parenterally (e.g., intrarectally, subcutaneously, intramuscularly or intravenously).

The active compound of the invention exhibits higher stability in vivo than PGI₂ when administered parenterally. But it can be advantageously administered orally as an enteric-coated preparation.

The active compound of this invention is administered, either singly or as the aforesaid pharmaceutical composition, or as a medicament in unit dosage form.

The dose of the active compound varies depending upon the type of the active compound, the subject to which it is administered, the condition, age, sex, and body weight of the subject, or the route of administration. Usually, it can be administered in a dose of about 0.02 μg to about 2 mg/kg of body weight/day. The dose may be administered once a day or in several portions, for example 2 to 6 times a day.

The active compound of this invention can be administered to a warm-blooded animal such as humans or other animals whose vascular actions require control. The active compound of this invention can be administered for preventive or therapeutic purposes to warm-blooded animals whose vascular actions require control. The active compound of this invention can be administered to subjects for vasodilation, blood pressure lowering or antithrombosis and also for controlling various conditions such as angina pectoris, arteriosclerosis, myocardial infarction, endotoxin shock, pulmonary hypertension, cerebral apoplexy, transient ischemic attack, thrombocytopenic purpura, deep vein thrombosis and peripheral vascular diseases.

The compound of this invention can also be used in organ transplantation, vascular surgery or extracorporeal circulation. For example, it may be used as an additive to a fluid which is used for artificial extracorporeal circulation of perfusion of blood, blood products, blood substitutes and isolated parts of the body (such as limbs or organs whether they adhere to the original body, or are separated and preserved or prepared for transplantation, or adhere to a new body). Platelets which are coagulated during such circulation or perfusion tend to clog the blood vessels and circulatory organs. The presence of the active compound of this invention can remove this tendency. For this purpose, the active compound of this invention is continuously infused in an amount of 0.1 ng to 1 μg/kg of body weight/min. at a time or in several portions to the circulating blood, the blood of a donor animal or a part of the body under perfusion (adhering or separated to or from the recipient), or to two or all of these.

Certain kinds of the compounds of the invention, for example 5-chloro $PGI_2$ or 7-fluoro $PGI_2$, have high platelet aggregation inhibiting activity but low blood pressure lowering activity. The active compounds of this invention which have such selective pharmacological activities can be advantageously used especially in the aforesaid extracorporeal circulation.

For oral administration, the pharmaceutical composition of this invention may be formulated into a solid preparation or a liquid preparation. Examples of the solid preparation include tablets, pills, powders and granules. In such solid preparations, at least one active compound is mixed with at least one pharmaceutically acceptable carrier such as sodium hydrogen carbonate, calcium carbonate, potato starch, sucrose, mannitol and carboxymethyl cellulose. These preparations can be made in a customary manner. There may also be used additives other additives for drug formulation, such as lubricants (e.g., calcium stearate, magnesium stearate and glycerol).

Examples of the liquid preparation for oral administration include emulsions, solutions, suspensions, syrups and elixirs. These preparations contain a usual pharmaceutically acceptable carrier such as water or liquid paraffin.

Enteric-coated preparations for oral administration can be produced by spraying a solution in an organic solvent or water of an intraintestinally soluble substance such as cellulose acetate phthalate, hydroxy propyl methyl cellulose phthalate, polyvinyl alcohol phthalate, a styrene/maleic anhydride copolymer or a methacrylic acid/methyl methacrylate copolymer onto the solid preparations exemplified above. The enteric-coated solid preparations such as powders or granules may be enclosed with capsules.

The pharmaceutically acceptable carrier in this invention includes usual auxiliary agents, such as wetting agents, suspension aids, sweetenings, flavors, aromas, stabilizers and antiseptics.

The liquid preparations may be administered in a form filled in capsules made of an absorbent material such as gelatin.

An example of the solid preparation for intrarectal administration is a suppository comprising at least one active compound and produced by a method known per se.

The prostacyclins of the invention can also be administered to the nasal cavity. A suitable nasal drop for administration to the nasal cavity is, for example, a mixture of the prostacyclin and a base such as hydroxypropyl cellulose or lactose, or a solution or suspension of the prostacyclin in physiological saline or an isotonic glucose solution.

Preparations for parenteral administration are given as aseptic aqueous or nonaqueous solutions, suspensions or emulsions. The nonaqueous solutions or suspensions contain propylene glycol, polyethylene glycol, a vegetable oil such as olive oil, an injectable organic ester such as ethyl oleate as the pharmaceutically acceptable carrier. Such preparations may also contain adjuvants such as antiseptics, wetting agents, emulsifiers, dispersing agents and stabilizers. These solutions, suspensions and emulsions can be sterilized by various treatments such as filtration through a bacteria-holding filler, incorporation of germicides, or irradiation. Alternatively, it is possible to produce an aseptic solid preparation and dissolve it in aseptic water or an aseptic injectable solvent just before use.

The pharmaceutical composition and medicament of this invention may be in such a form that the active compound is contained as an inclusion compound with cyclodextrin as is well known in the art.

The following examples illustrate the present invention more specifically.

EXAMPLE 1

Synthesis of 5-bromo-$\Delta^6$-$PGI_1$ methyl ester-11,15-bis-t-butyldimethylsilyl ether (No. 320):

30 mg of $PGI_2$ methyl ester 11,15-bis-t-butyldimethylsilyl ether was dissolved in 0.4 ml of methylene chloride, and 6 mg of N-bromosuccinimide was added at 0° C. The reaction was carried out for 1 hour. The reaction mixture was purified by silica gel column chromatography [cyclohexane/ethyl acetate=99:1 (triethylamine, 0.5%)] to give 7 mg of the captioned compound No. 320 which had the following properties.

NMR $(CDCl_3)\delta$:
3.69 (3H, s), 3.78–4.15 (2H, m), 4.3–4.9 (2H, m), 5.02 (1H, d, J=2 Hz), 5.5 (2H, m).

Mass (20 eV):
674, 672 (M+), 617, 615, 592, 577, 561, 535, 377.

EXAMPLE 2

Synthesis of 5-bromo-$\Delta^6$-$PGI_1$ methyl ester 11,15-bis-butyldimethylsilyl ether (No. 320):

15 mg (0.025 millimole) of $PGI_2$ methyl ester 11,15-bis-t-butyldimethylsilyl ether and 11 microliters of triethylamine were dissolved in 0.6 ml of methylene chloride, and the solution was cooled to −74° C. 0.025 millimole of a methylene chloride solution of bromine was added dropwise. Immediately after the addition, the reaction mixture was poured into 1 ml of a saturated aqueous solution of sodium bicarbonate, extracted with methylene chloride, dried, and then worked up in the same way as in Example 1 to give 5 mg of the captioned compound No. 320.

EXAMPLE 3

Synthesis of 5-bromo-$\Delta^6$-PGI$_1$ methyl ester (No. 224):

7 mg of 5-bromo-$\Delta^6$-PGI$_1$ methyl ester 11,15-bis-t-butyldimethylsilyl ether was dissolved in 0.2 ml of tetrahydrofuran, and under ice cooling, 0.1 ml of a tetrahydrofuran solution of 10 mg of tetrabutyl ammonium fluoride was added. The mixture was stirred at room temperature for 1 hour. The reaction mixture was purified by Florisil column chromatography (cyclohexane/ethyl acetate=3:7, 0.5% triethylamine) to give 2.5 mg of the captioned compound No. 224 having the following properties.

NMR (CDCl$_3$) $\delta$:
3.68 (3H, s), 3.75–4.2 (2H, m), 4.3–4.9 (2H, m), 5.04 (1H, d, J=2 Hz), 5.5 (2H, m).

EXAMPLE 4

Synthesis of 5-bromo-17(S),20-dimethyl-$\Delta^6$-PGI$_1$ methyl ester 11,15-bis-t-butyldiphenylsilyl ether (No. 312):

18 mg of 17(S), 20-dimethyl PGI$_2$ methyl ester 11,15-bis-t-butyldiphenylsilyl ether was dissolved in 0.2 ml of carbon tetrachloride, and 6 mg of N,N-dibromo-5,5-dimethylhydantoin was added at room temperature. The mixture was stirred for 30 minutes, and then worked up in the same way as in Example 1 to give the captioned compound No. 312.

NMR (100 MHz, CDCl$_3$)$\delta$:
0.9 (3H), 1.03 (18H), 1.0–2.7 (21H),
2.9–3.3 (1H), 3.65 (3H), 3.70–5.00 (4H),
4.98 (1H), 5.50 (2H), 7.3–7.7 (10H).

EXAMPLE 5

Synthesis of 5-bromo-$\Delta^6$-PGI$_1$ methyl ester 11,15-diacetate (No. 298):

200 mg of PGI$_2$ methyl ester diacetate was dissolved in 9 ml of carbon tetrachloride, and 94 mg of potassium carbonate and then 83 mg of N-bromosuccinimide were added. The mixture was stirred at room temperature for 1 hour. A saturated aqueous solution of sodium bicarbonate was added, and the mixture was extracted with diethyl ether twice. The ethereal layers were combined, washed twice with water, and then dried over anhydrous sodium sulfate. The solvent was distilled off. The residue was chromatographed on a column of Florisil. An eluate with 10–15% ethyl acetate/n-hexane (containing 0.1% triethylamine) contained 137 mg of the desired compound No. 298.

NMR (CDCl$_3$) $\delta$:
1.99 (3H, s), 2.02 (3H, s), 2.9–3.3 (1H, br), 3.66 (3H, s), 4.42 (1H, t, J=7 Hz), 4.6–5.3 (4H, m), 5.4–5.6 (2H, m)

EXAMPLE 6

Synthesis of 5-bromo-$\Delta^6$-PGI$_1$ methyl ester 11,15-diacetate (No. 298):

32 microliters of triethylamine and then 1 ml of diethyl ether were added to 20 mg of PGI$_2$ methyl ester diacetate, and the mixture was cooled to $-70°$ C. in an argon atmosphere. 12 mg of dioxane dibromide was added, and the mixture was stirred at $-70°$ C. to room temperature for 2 hours. Then, a saturated aqueous solution of sodium bicarbonate was added, and the mixture was extracted with diethyl ether twice. The extracts were combined, washed with a saturated aqueous solution of sodium chloride, dried with anhydrous magnesium sulfate, and concentrated. The residue was purified by thin-layer chromatography using 15% ethyl acetate/benzene to give 5.2 mg (yield 22%) of 5-bromo-$\Delta^6$-PGI$_1$ methyl ester 11,15-diacetate which showed the same NMR data as shown in Example 5.

EXAMPLE 7

Synthesis of 5-bromo-$\Delta^6$-PGI$_1$ methyl ester 11,15-diacetate (No. 294):

20 mg of PGI$_2$ methyl ester 11,15-diacetate was dissolved in 0.3 ml of methylene chloride, and 9 mg of t-butyl hypobromite was added at $-78°$ C. The mixture was reacted for 30 minutes, and then poured into 5 ml of methylene chloride and 5 ml of a saturated aqueous solution of sodium bicarbonate. The separated organic layer was washed with a saturated aqueous solution of sodium chloride, dried over potassium carbonate-magnesium sulfate, and distilled under reduced pressure. The resulting crude product was purified in the same way as in Example 5 to give 12 mg of the captioned compound No. 294.

EXAMPLE 8

Synthesis of 5-bromo-$\Delta^6$-PGI$_1$ methyl ester 11,15-diacetate (No. 298):

56 microliters of triethylamine and then 1 ml of diethyl ether were added to 30 mg of PGI$_2$ methyl ester 11,15-diacetate, and the mixture was cooled to $-70°$ C. under an argon atmosphere. Then, 23 mg of pyridinium hydrobromide perbromide was added, and the mixture was stirred at $-70°$ C. to $-20°$ C. for 2 hours. A saturated aqueous solution of sodium bicarbonate was added to the reaction mixture. The mixture was extracted with diethyl ether twice. The extracts were combined, washed with a saturated aqueous solution of sodium chloride twice, and dried over anhydrous magnesium sulfate. The solvent was evaporated off. The residue was purified by thin-layer chromatography using 15% ethyl acetate-benzene as a developing solvent to give 7.0 mg (yield 20%) of 5-bromo-$\Delta^6$-PSI$_1$ methyl ester which had the same NMR data as shown in Example 5.

EXAMPLE 9

Synthesis of 5-bromo-17(R),20-dimethyl-$\Delta^6$-PGI$_1$ n-butyl ester 11,15-bis-t-butyldimethylsilyl ether (No. 317):

40 mg of 17(R),20-dimethyl PGI$_2$ n-butyl ester 11,15-bis-t-butyldimethylsilyl ether was dissolved in 1.5 ml of diethyl ether, and 50 microliters of triethylamine was added. 12 mg of N-bromosuccinimide was added. The mixture was stirred at room temperature for 30 minutes. The reaction mixture was purified by Florisil column chromatography (0.5% ethyl acetate-hexane, containing 0.1% triethylamine) to give 23 mg (yield 51%) of 5-bromo-17(R),20-dimethyl-$\Delta^6$-PGI$_1$ butyl ester 11,15-bis-t-butyldimethylsilyl ether.

NMR (CDCl$_3$) $\delta$:
0.88 (18H, s), 3.7–4.2 (4H, m), 4.45 (1H, t, J=8 Hz), 4.7–5.1 (2H, m), 5.4–5.6 (2H, m).

EXAMPLE 10

Synthesis of 5-bromo-16,16-dimethyl-$\Delta^6$-PSI$_1$ methyl ester 11,15-diacetate (No. 300):

20 mg of 16,16-dimethyl PGI$_2$ methyl ester diacetate was dissolved in 1 ml of n-hexane, and one drop of triethylamine was added. The mixture was then cooled to $-40°$ C. 7 mg of t-butyl hypobromite was added, and the mixture was stirred at $-40°$ C. for 1 hour. A saturated aqueous solution of sodium bicarbonate was added to the reaction mixture, and the mixture was extracted with diethyl ether twice. The extracts were combined, washed with brine and dried over anhydrous magnesium sulfate. The solvent was distilled off under reduced pressure. The residue was purified by thin-layer chromatography using 15% ethyl acetate-benzene as a developing solvent to give 7 mg (yield 30%) of 5-bromo-16,16-dimethyl-$\Delta^6$-PGI$_1$ methyl ester 11,15-diacetate.

NMR (DCDl$_3$) δ:
2.00 (3H, s), 2.03 (3H, s), 3.67 (3H, s), 4.43 (1H, t, J=8 Hz), 4.7–5.3 (4H, m), 5.5–5.7 (2H, m).

EXAMPLE 11

Synthesis of 5-bromo-15-cyclohexyl-16,17,18,19,20-pentanor-$\Delta^6$-PSI$_1$ n-decyl ester 11,15-diacetate (No. 302):

42 mg of 15-cyclohexyl-16,17,18,19,20-pentanor-PGI$_2$ decyl ester 11,15-diacetate was dissolved in 2 ml of dichloromethane, and 13 mg of N-bromosuccinimide was added. The mixture was stirred at $-40°$ C. to room temperature for 2 hours. A saturated aqueous solution of sodium bicarbonate was added. The mixture was extracted with diethyl ether twice. The extracts were combined, washed with a saturated aqueous solution of sodium chloride, and dried over anhydrous magnesium sulfate. The solvent was evaporated off, and the residue was separated by Florisil column chromatography to give 25 mg (yield 52%) of 5-bromo-15-cyclohexyl-16,17,18,19,20-pentanor-$\Delta^6$-PGI$_1$ n-decyl ester 11,15-diacetate.

NMR (100 Hz, CDCl$_3$) δ:
2.01 (3H, s), 2.04 (3H, s), 4.05 (2H, t, J=6 Hz), 4.43 (1H, t, J=8 Hz), 4.6–5.2 (4H, m), 5.50 (2H, m).

EXAMPLE 12

Synthesis of 5-bromo-13,14-dehydro-$\Delta^6$-PGI$_1$ n-butyl ester 11,15-diacetate (No. 306):

To 30 mg of 13,14-dehydro PGI$_2$ n-butyl ester diacetate were added 20 mg of potassium carbonate and then 1 ml of dichloromethane. 18 mg of 1,3-dibromo-5,5-dimethylhydantoin was added. The mixture was stirred at room temperature for 1 hour, and a saturated aqueous solution of sodium bicarbonate was added. The mixture was extracted with diethyl ether twice. The extracts were combined, washed with a saturated aqueous solution of sodium chloride, and dried over anhydrous magnesium sulfate. The solvent was evaporated off, and the reside was purified by thin-layer chromatography using 10% ethyl acetatebenzene as a developing solvent to give 12 mg of 5-bromo-13,14-dehydro-$\Delta^6$-PGI$_1$ n-butyl ester 11,15-diacetate.

NMR (CDCl$_3$) δ:
2.00 (3H, s), 2.02 (3H, s), 4.07 (2H, t, J=6 Hz), 4.45 (1H, t, J=8 Hz), 4.6–5.2 (4H, m).

EXAMPLE 13

Synthesis of 5-bromo-17(S),20-dimethyl-$\Delta^6$-PGI$_1$ methyl ester 11,15-bis-t-butyldiphenylsilyl ether (No. 312):

30 mg of 17(S),20-dimethyl PGI$_2$ methyl ester 11,15-bis-t-butyldiphenylsilyl ether was dissolved in 1 ml of carbon tetrachloride, and 20 mg of potassium carbonate was added. 7 mg of N-bromosuccinimide was added, and the mixture was stirred at room temperature for 30 minutes. A saturated aqueous solution of sodium bicarbonate was added. The mixture was extracted with diethyl twice. The extracts were combined and washed with a saturated aqueous solution of sodium chloride, followed by drying and distilling off the solvent. The residue was purified by thin-layer chromatography using 8% ethyl acetate-hexane as a developing solvent to give 16 mg (yield 49%) of 5-bromo-$\Delta^6$-PGI$_1$ methyl ester 11,15-bis-t-butyldiphenylsilyl ether which showed the same NMR data as obtained in Example 4.

EXAMPLE 14

Synthesis of 7-bromo-PGI$_2$ methyl ester 11,15-bis-t-butyldimethylsilyl ether (No. 750):

18 mg of $\Delta^6$-PGI$_1$ methyl ester 11,15-bis-t-butyldimethylsilyl ether was dissolved in 1 ml of diethyl ether, and 6 mg of N-bromosuccinimide was added. The mixture was stirred at room temperature for 30 minutes. The reaction mixture was worked up in the same way as in Example 1 to give 5 mg of the desired compound No. 750.

NMR (100 MHz, CDCl$_3$) δ:
0.88 (21H), 1.0–2.8 (18H), 3.66 (3H), 3.80 (1H), 4.08 (1H), 4.55 (1H), 4.62 (1H), 4.85 (1H), 5.52 (2H).

EXAMPLE 15

Synthesis of 5-chloro-$\Delta^6$-PGI$_1$ methyl ester 11,15-bis-t-butyldimethylsilyl ether (No. 308):

22 mg of PGI$_2$ methyl ester 11,15-bis-t-butyldimethylsilyl ether was dissolved in 0.5 ml of diethyl ether, and with ice cooling, 4.5 mg of N-chlorosuccinimide was added. The mixture was stirred at the same temperature for 1 hour, and the solvent was distilled off.

Immediately then, the residue was purified by Florisil column chromatography (cyclohexane/ethyl acetate=99:1, containing 0.5% triethylamine) to give 12 mg of the captioned compound No. 308.

NMR (CDCl$_3$) δ:
0.88 (21H, s), 1.1–2.6 (17H), 2.85–3.2 (1H, m), 3.66 (3H, s), 3.7–4.2 (2H, m), 4.40 (1H, m), 4.7–5.0 (1H, m), 5.00 (1H, d, J=3 Hz), 5.50 (2H, m).

Mass (70 eV):
630, 628 (M+), 592, 573, 571, 535.

EXAMPLE 16

Synthesis of 5-chloro-$\Delta^6$-PGI$_1$ methyl ester (No. 222):

12 mg of 5-chloro-$\Delta^6$-PGI$_1$ methyl ester 11,15-bis-t-butyl-dimethylsilyl ether was dissolved in 0.2 ml of tetrahydrofuran, and with ice cooling 0.1 ml of a tetrahydrofuran solution of 12 mg of tetrabutyl ammonium fluoride was added. The mixture was stirred at room temperature for 4 hours.

The reaction mixture was purified by Florisil column chromatography (cyclohexane/ethyl acetate=3:7, containing 0.5% triethylamine) to give 4 mg of the captioned compound No. 222.

NMR (CDCl$_3$) δ:

0.89 (3H, m), 1.1–2.5 (17H, m), 3.0–3.1 (1H, m), 3.68 (3H, s), 3.7–4.15 (2H, m), 4.38 (1H, t, J=7 Hz), 5.04 (1H, d, J=3 Hz), 4.8–5.2 (1H, m), 5.53 (2H, m).

EXAMPLE 17

Synthesis of a sodium salt of 5-chloro-$\Delta^6$-PGI$_1$ (No. 322):

3 mg of 5-chloro-$\Delta^6$-PGI$_1$ methyl ester was stirred at room temperature for 2 hours in 0.1 ml of a 1N aqueous solution of sodium hydroxide and 0.1 ml of ethanol to prepare an aqueous alkali-ethanol solution of a sodium salt of 5-chloro-$\Delta^6$-PGI$_1$.

EXAMPLE 18

Synthesis of 5-chloro-15-cyclohexyl-16,17,18,19,20-pentanor-$\Delta^6$-PGI$_1$ methyl ester 11,15-bis-t-butyldimethylsilyl ether (No. 310):

35 mg of 15-cyclohexyl-16,17,18,19,20-pentanor-PGI$_2$ methyl ester 11,15-bis-t-butyldimethylsilyl ether and 10 microliters of triethylamine were dissolved in 0.5 ml of carbon tetrachloride, and 9 mg of N-chlorosuccinimide was added at room temperature. The mixture was stirred for 1 hour. The reaction mixture was worked up in the same way as in Example 15 to give 15 mg of the captioned compound No. 310.

NMR (100 MHz, CDCl$_3$) δ:
0.88 (18H), 1.0–2.6 (21H), 2.8–3.2 (1H), 3.65 (3H), 3.7–4.3 (2H), 4.38 (1H), 4.98 (1H), 4.7–5.1 (1H), 5.50 (2H).

EXAMPLE 19

Synthesis of 5-chloro-15-methyl-$\Delta^6$-PGI$_1$ methyl ester 11,15-diacetate (No. 292):

20 mg of 15-methyl PGI$_2$ methyl ester 11,15-diacetate was dissolved in 0.2 ml of methylene chloride, and at room temperature, 9 mg of N-chlorophthalimide was added. The reaction was performed for 2 hours. The reaction mixture was worked up in the same way as in Example 15 to give 11 mg of the captioned compound No. 292.

NMR (100 MHz, CDCl$_3$) δ:
0.8–3.3 (27H), 2.00 (6H), 3.65 (3H), 4.40 (1H), 4.7–5.3 (3H), 5.5 (2H).

EXAMPLE 20

Synthesis of 5-chloro-17(S),20-dimethyl-PGI$_1$ methyl ester (No. 266):

20 mg of 17(S),20-dimethyl-PGI$_2$ methyl ester 11,15-bis-t-butyldimethylsilyl ether was dissolved in 0.5 ml of methylene chloride, and treated with 4 mg of N-chlorosuccinimide in the same way as in Example 15 to give 8 mg of 5-chloro-17(S),20-dimethyl-PGI$_1$ methyl ester 11,15-bis-t-butyldimethylsilyl ether (No. 315). The product was then desilylated in the same may as in Example 5 to give 3.5 mg of the captioned compound No. 266.

NMR (100 MHz, CDCl$_3$) δ:
0.9 (3H), 1.0–2.6 (23H), 2.85–3.3 (1H), 3.67 (3H), 3.7–4.35 (2H), 4.45 (1H), 4.65–5.1 (2H), 5.50 (2H).

EXAMPLE 21

Synthesis of 5-chloro-17(R),20-dimethyl-$\Delta^6$-PGI$_1$ n-butyl ester 11,15-bis-t-butyldiphenylsilyl ether (No. 746):

56 mg of 17(R),20-dimethyl-PGI$_2$ n-butyl ester 11,15-bis-t-butyldiphenylsilyl ether was dissolved in 1 ml of methylene chloride, and 16 mg of trichloroisocyanuric acid was added at 0° C. The reaction was carried out at this temperature for 2 hours. 30 ml of diethyl ether was added, followed by washing with a saturated aqueous solution of sodium bicarbonate and water and drying over potassium carbonate-magnesium sulfate. The dried product was filtered and distilled under reduced pressure. The resulting oily product was purified by Florisil column chromatography (cyclohexane/ethyl acetate=99:1, containing 0.1% triethylamine) to give 26 mg of the captioned compound No. 746.

NMR (CDCl$_3$) δ:
0.9 (6H), 1.05 (18H), 1.0–2.6 (25H), 2.85–3.3 (1H), 3.67 (3H), 3.7–4.3 (4H), 4.4 (1H), 4.65–5.1 (2H), 5.48 (2H), 7.3–7.7 (20H).

EXAMPLE 22

Synthesis of 5-chloro-13,14-dehydro-$\Delta^6$-PGI$_1$ n-decyl ester 11,15-bis-t-butyldimethylsilyl ether (No. 314):

15 mg of 13,14-dehydro-PGI$_2$ decyl ester 11,15-bis-t-butyldimethylsilyl ether was dissolved in 0.2 ml of diethyl ether. 4 mg of t-butyl hypochlorite was added at −78° C., and the reaction was carried out for 30 minutes. The reaction mixture was worked up and purified in the same way as in Example 15 to give 9.5 mg of the captioned compound No. 314.

NMR (100 MHz, CDCl$_3$):
0.8–3.2, (58H), 3.8–4.5 (5H), 4.7–5.0 (2H).

EXAMPLE 23

Synthesis of 5-chloro-13,14-dihydro-$\Delta^6$-PGI$_1$ methyl ester 11,15-t-butyldimethylsilyl ether (No. 316):

10 mg of 13,14-dihydro-PGI$_2$ methyl ester 11,15-bis-t-butyldimethylsilyl ether was dissolved in 0.2 ml of methylene chloride, and 5 mg of N,N-dichlorohydantoin was added. The mixture was stirred at room temperature for 30 minutes, and the reaction mixture was worked up in the same way as in Example 15 to give 4 mg of the captioned compound No. 316.

NMR (100 MHz,CDCl$_3$) δ:
0.88 (21H), 1.0–2.6 (21H), 2.8–3.2 (1H), 3.65 (3H), 3.7–4.3 (2H), 4.38 (1H), 5.00 (1H), 4.7–5.1 (1H).

EXAMPLE 24

Synthesis of 5-chloro-16,16-dimethyl-$\Delta^6$-PGI$_1$ n-butyl ester 11,15-diacetate (No. 296):

8 mg of N-chlorosuccinimide was added to a solution of 25 mg of 5-chloro-16,16-dimethyl PGI$_2$ n-butyl ester 11,15-diacetate and 8 mg of potassium carbonate in 0.3 ml of diethyl ether, and the mixture was stirred at room temperature for 1 hour. The reaction mixture was worked up in the same way as in Example 5 to give 15 mg of the cationed compound No. 296.

NMR (100 MHz,CDCl$_3$) δ:
0.8–2.6 (33H), 2.7–3.2 (1H), 2.0 (6H), 4.25 (2H), 4.40 (1H), 4.6–5.3 (3H), 5.50 (2H).

EXAMPLE 25

Synthesis of 7-chloro-PGI$_2$ methyl ester 11,15-diacetate (No. 742):

15 mg of $\Delta^6$-PGI$_1$ methyl ester 11,15-diacetate was reacted with 4 mg of N-chlorosuccinimide in 0.5 ml of methylene chloride in the same way as in Example 15 to give 7 mg of the captioned compound No. 742.

NMR (100 MHz,CDCl$_3$) δ:
0.85 (3H), 1.0–2.8 (24H), 3.66 (3H), 4.3–5.2 (4H), 5.50 (2H).

EXAMPLE 26

Synthesis of 5-iodo-$\Delta^6$-PGI$_1$ methyl ester 11,15-diacetate (No. 291):

5 mg (0.036 millimole) of potassium carbonate was added to 11 mg (0.024 millimole) of PGI$_2$ methyl ester 11,15-diacetate, and the mixture was dissolved in 5 ml of tetrachloromethane. In an argon atmosphere, 5.8 mg (0.025 millimole) of N-iodosuccinimide was added, and the mixture was stirred at room temperature for 1 hour. After the reaction, the reaction mixture was directly chromatographed on a column of Florisil using 10% ethyl acetate/n-hexane/0.1% triethylamine to give 4 mg of the captioned compound No. 291.

NMR (CDCl$_3$) $\delta$:
3.67 (3H, s), 4.6–5.3 (4H, m), 5.5–5.7 (2H, m).

Mass (20 eV, m/e):
576 (M$^{30}$), 516, 450, 449, 390, 389, 330, 329, 259, 254, 195, 193.

EXAMPLE 27

Synthesis of (5E)-5-bromo-PGI$_2$ methyl ester 11,15-bis-t-butyldimethylsilyl ether (No. 760) and 5(Z)-5-bromo-PGI$_2$ methyl ester 11,15-bis-t-butyldimethylsilyl ether (No. 5Z-760):

10 mg of 5-bromo-$\Delta^6$-PGI$_1$ methyl ester bis-t-butyldimethylsilyl ether was dissolved in 0.5 ml of chloroform. With vigorous stirring, one drop of conc. sulfuric acid was added by means of a microsyringe. The mixture was stirred at room temperature for 2 minutes. 5 ml of a saturated aqueous solution of sodium bicarbonate was added at a time to the reaction mixture, and the mixture was extracted with 10 ml of methylene chloride twice. The organic layers were combined, washed with 8 ml of an aqueous solution of sodium bicarbonate, and dried over magnesium sulfate-potassium carbonate. The solvent was distilled off under reduced pressure. The resulting oil was purified by silica gel thin-layer chromatography using 10% ethyl acetate/hexane as a developing solvent to give two compounds as an oil.

Compound No. 760 (less polar)

Amount yielded:
1.0 mg
Mass (70 eV, m/e):
674, 672, 617, 615, 592, 535.
NMR (100 MHz, $\delta_{TMS}^{CDCl_3}$):
5.45–5.65 (2H, m), 4.55–4.85 (1H, m), 3.65–4.30 (2H, m), 3.66 (3H, s), 0.88 (21H, s), Compound No. 5Z-760 (more polar)

Amount yielded:
1.2 mg
Mass (70 eV, m/e):
674, 672, 617, 615, 592, 535.
NMR (100 MHz, $\delta_{TMS}^{CDCl_3}$):
5.45–5.65 (2H, m), 4.55–4.80 (1H, m), 3.65–4.25 (2H, m), 3.68 (3H, s), 0.88 (21H, s).

EXAMPLE 28

Synthesis of (5E)-5-bromo-PGI$_2$ methyl ester (No. 638):

1.0 mg of (5E)-5-bromo-PGI$_2$ methyl ester 11,15-bis-t-butyldimethylsilyl ether was treated in the same way as in Example 3 to give 0.5 mg of the captioned compound No. 638.

Mass (70 eV, m/e):
446, 444, 428, 420, 410, 408, 347.

EXAMPLE 29

Synthesis of (5Z)-5-bromo-PGI$_2$ methyl ester (No. 5Z-638):

1.2 mg (5Z)-5-bromo-PGI$_2$ methyl ester 11,15-bis-t-butyldimethylsilyl ether was treated in the same way as in Example 3 to give 0.5 mg of the captioned compound No. 5Z-638.

Mass (70 eV, m/e):
446, 444, 428, 420, 410, 408, 347.

EXAMPLE 30

Synthesis of a sodium salt of (5E)-5-bromo-PGI$_2$ (No. 689):

0.1 ml of a 0.1N aqueous solution of sodium hydroxide and 0.2 ml of ethanol were added to 0.5 mg of (5E)-5-bromo-PGI$_2$ methyl ester, and the mixture was stirred at room temperature for 10 hours to give a solution of the desired compound No. 689.

EXAMPLE 31

Synthesis of (5Z)-5-bromo-PGI$_2$, sodium salt (No. 5Z-689):

0.1 ml of a 0.1N aqueous solution of sodium hydroxide and 0.2 ml of ethanol were added to 0.5 mg of (5Z)-5-bromo-PGI$_2$ methyl ester, and the mixture was stirred at room temperature for 10 hours to give a solution of the captioned compound No. 5Z-689.

EXAMPLE 32

Synthesis of (5E)-5-chloro-PGI$_2$ methyl ester 11,15-bis-t-butyldimethylsilyl ether (No. 752) and (5Z)-5-chloro-PGI$_2$ methyl ester 11,15-bis-t-butyldimethylsilyl ether (No. 5Z-752):

33 mg of 5-chloro-$\Delta^6$-PGI$_1$ methyl ester 11,15-bis-t-butyl-dimethylsilyl ether was dissolved in 0.5 ml of chloroform, and with vigorous stirring, one drop of conc. sulfuric acid was added by means of a microsyringe. The mixture was stirred at room temperature for 3 minutes. 5 ml of a saturated aqueous solution of sodium bicarbonate was added at a time, and the mixture was extracted with 10 ml of methylene chloride twice. The organic layers were combined, washed with 8 ml of a saturated aqueous solution of sodium bicarbonate, and dried over magnesium sulfate-potassium carbonate. The solvent was distilled off under reduced pressure. The resulting oil was purified by silica gel thin-layer chromatography using 10% ethyl acetate/hexane as a developing solvent to give two oily compounds.

Compound No. 752 (less polar)

Amount yielded:
4.9 mg
Mass (70 eV, m/e):
630, 628, 573, 571, 535
NMR (100 MHz, $\delta_{TMS}^{CDCl_3}$):
5.48 (2H, m), 4.63 (1H, m), 4.06 (1H, m), 3.84 (1H, m), 3.66 (3H, s), 0.89 (9H, s), 0.86 (9H, s).

Compound No. 5Z-752 (more polar)

Amount yielded:
8.7 mg
Mass (70 eV, m/e):
630, 628, 573, 571, 535
NMR (100 MHz, $\delta_{TMS}^{CDCl_3}$):
5.47 (2H, m), 4.70 (1H, m), 4.07 (1H, m), 3.94 (1H, m), 3.67 (3H, s), 0.89 (9H, s), 0.86 (9H, s).

EXAMPLE 33

Synthesis of (5E)-5-chloro-PGI$_2$ methyl ester (No. 636):

4.9 mg of (5E)-chloro-PGI$_2$ methyl ester 11,15-bis-t-butyl-dimethylsilyl ether was dissolved in 1 ml of tetrahydrofuran, and 20 microliters of triethylamine was added. Then, 42 mg of tetra-n-butyl ammonium fluoride trihydrate [(C$_4$H$_9$)$_4$NF.3H$_2$O] was added. The mixture was stirred at room temperature for 4 hours. 15 ml of a saturated aqueous solution of sodium bicarbonate was added, and the mixture was extracted with 15 ml of ethyl acetate twice. The organic layers were combined, washed with 15 ml of a saturated aqueous solution of sodium chloride and then 10 ml of water, and dried over magnesium sulfate-potassium carbonate. The solvent was distilled off under reduced pressure. The residue was purified by silica gel thin-layer chromatography using ethyl acetate/benzene=1:9 as a developing solvent to give 2.0 mg of the captioned compound No. 636.

Mass (20 eV, m/e):
402, 400, 384, 382, 366, 364, 365, 347.
NMR (100 MHz, $\delta_{TMS}^{CDCl_3}$):
5.58 (2H, m), 4.55–4.75 (1H, m), 4.95–4.2 (1H, m), 3.7–4.0 (1H, m), 3.68 (3H, s).

EXAMPLE 34

Synthesis of (5Z)-5-chloro-PGI$_2$ methyl ester (No. 5Z-636):

8.7 mg of (5E)-5-chloro-PGI$_2$ methyl ester 11,15-bis-t-butyldimethyl-silyl ether was treated in the same way as in Example 3 to give 3.8 mg of the captioned compound No. 5Z-636.

Mass (20 eV, m/e):
402, 400, 384, 382, 366, 364, 365, 347.
NMR (100 MHz, $\delta_{TMS}^{CDCl_3}$):
5.59 (2H, m), 4.6–4.85 (1H, m), 4.0–4.2 (1H, m), 3.7–4.0 (1H, m), 3.67 (3H, s).

EXAMPLE 35

Synthesis of (5E)-5-chloro-PGI$_2$, sodium salt (No. 686):

0.2 ml of a 0.1N aqueous solution of sodium hydroxide and 0.5 ml of ethanol were added to 1.6 mg of (5E)-5-chloro-PGI$_2$ methyl ester, and the mixture was stirred at room temperature for 6 hours. The reaction was monitored by silica gel thin-layer chromatography (developing solvent: dichloromethane/acetone=7:3), and it was found that hydrolysis of the ester proceeded completely. There was obtained a solution of the captioned compound No. 686.

EXAMPLE 36

Synthesis of (5Z)-5-chloro-PGI$_2$, sodium salt (No. 5Z-686):

0.3 ml of a 0.1N aqueous solution of sodium hydroxide and 0.6 ml of ethanol were added to 2.0 mg of (5Z)-5-chloro-PGI$_2$ methyl ester, and the mixture was stirred at room temperature for 6 hours to give a solution of the captioned compound No. 5Z-686.

EXAMPLE 37

Synthesis of (5E)-5-chloro-PGI$_2$ methyl ester 11,15-bis-t-butyldimethylsilyl ether (No. 752) and (5Z)-5-chloro-PGI$_2$ methyl ester 11,15-bis-t-butyldimethylsilyl ether (No. 5Z-752):

27 mg of the same 5-chloro-$\Delta^6$-PGI$_1$ methyl ester bis-t-butyldimethylsilyl ether as obtained in Example 15 was dissolved in 1 ml of benzene, and 4 mg of pyridinium p-toluenesulfonate was added. The mixture was stirred overnight, and 600 mg of anhydrous magnesium sulfate was added. The mixture was heated under reflux for 3 hours. A saturated aqueous solution of sodium bicarbonate was added to the reaction mixture, and the mixture was extracted with ethyl acetate twice. The extracts were combined and washed with brine twice. The crude product was purified by thin-layer chromatography using 10% ethyl acetate/benzene as a developing solvent to give 6 mg of the captioned compound No. 752 and 8 mg of the captioned compound No. 5Z-752. The spectral data of these compounds were the same as those given in Example 32.

EXAMPLE 38

Synthesis of (5E)-5-chloro-15-cyclohexyl-16,17,18,19,20-pentanor-PGI$_2$ methyl ester (No. 641):

15 mg of 5-chloro-15-cyclohexyl-16,17,18,19,20-pentanor-$\Delta^6$-PGI$_1$ methyl ester 11,15-bis-t-butyldimethylsilyl ether was subjected to rearrangement reaction in the same way as in Example 37 and desilylated in the same way as in Example 33 to give 3 mg of the captioned compound No. 641.

NMR (100 MHz, CDCl$_3$) $\delta$:
1.0–2.5 (25H), 3.65 (3H), 3.9–4.2 (2H), 5.48 (2H).

EXAMPLE 39

Preparation of a solution of 5-chloro-15-cyclohexyl-16,17,18,19,20-pentanor-PGI$_2$, sodium salt (No. 699):

When 2 mg of 15-cyclohexyl-16,17,18,19,20-pentanor PGI$_2$ methyl ester was reacted with 20 microliters of a 1N aqueous solution of sodium hydroxide in 30 microliters of ethanol at room temperature for 3 hours, a spot to be attributed to the starting material in thin-layer chromatography completely disappeared. A solution of 5-chloro-15-cyclohexyl-16,17,18,19,20-pentanor-PGI$_2$ sodium salt (No. 699) was prepared in this manner.

EXAMPLE 40

Synthesis of (5E)-5-chloro-16,16-dimethyl PGI$_2$ n-butyl ester (No. 661):

(1) When 35 mg of 5-chloro-16,16-dimethyl-$\Delta^6$-PGI$_1$ n-butyl ester 11,15-diacetate was subjected to the same rearrangement reaction as in Example 37, 15 mg of (5E)-5-chloro-16,16-dimethyl-PGI$_2$ n-butyl ester 11,15-diacetate was obtained.

(2) 3 ml of dry methanol containing 0.16 millimole of sodium methoxide cooled to $-40°$ C. was added to 15 mg of the compound obtained in (1) above, and the mixture was left to stand at $-20°$ C. for 16 hours. 10 ml of a dilute aqueous solution of sodium bicarbonate was added. The mixture was extracted with 10 ml of ethyl acetate twice. The extracts were combined, washed with 8 ml of water, and dried over magnesium sulfate-potassium carbonate. The solvent was distilled off under reduced pressure to give 10 mg of the captioned compound No. 661.

NMR (100 MHz, CDCl$_3$) $\delta$:
0.8–2.6 (36H), 3.7–4.2 (4H), 4.4–4.8 (1H), 5.52 (2H).

EXAMPLE 41

Synthesis of (5E)-5-chloro-15-methyl-PGI$_2$ methyl ester (No. 645) and (5Z)-5-chloro-15-methyl PGI$_2$ methyl ester (No. 5Z-645):

(1) 10 mg of 5-chloro-15-methyl-$\Delta^6$-PGI$_1$ methyl ester 11,15-diacetate was dissolved in 0.5 ml of benzene, and 2 mg of pyridinium p-toluenesulfonate was added.

The mixture was stirred for a day, and 0.5 ml of benzene was added. Furthermore, 200 mg of anhydrous magnesium sulfate was added, and the mixture was heated under reflux for 3 hours. The reaction mixture was worked up in the same way as in Example 37 to give 2 mg of (5E)-5-chloro-15-methyl PGI$_2$ methyl ester 11,15-diacetate (No. 744) and 3.5 mg of (5Z)-5-chloro-15-methyl PGI$_2$ methyl ester 11,15-diacetate (No. 5Z-744).

(2) Each of the compounds obtained in (1) above was treated with sodium methoxide in methanol in the same way as in Example 40 to deacetylate it. Thus, 1.5 mg of the captioned compound No. 645 and 2.5 mg of the captioned compound No. 5Z-645 were obtained.

Compound No. 645

NMR (100 MHz, CDCl$_3$) $\delta$:
0.8–2.5 (28H), 3.66 (3H), 4.0–4.2 (1H), 4.55–4.8 (1H), 5.55 (2H).

Compound No. 5Z-645

NMR (100 MHz, CDCl$_3$) $\delta$:
0.8–2.5 (28H), 3.65 (3H), 4.0–4.25 (1H), 4.50–4.8 (1H), 5.55 (2H).

EXAMPLE 42

Synthesis of (5E)-5-chloro-15-methyl-PGI$_2$ sodium salt (No. 703):

One milligram of (5E)-5-chloro-15-methyl-PGI$_2$ methyl ester was treated in the same way as in Example 35 to give a solution of the captioned compound No. 703.

EXAMPLE 43

Synthesis of (5E)-5-chloro-17(S),20-dimethyl-PGI$_2$-methyl ester (No. 657):

12 mg of 5-chloro-17(S),20-dimethyl-$\Delta^6$-PGI$_1$ methyl ester 11,15-bis-t-butyldimethylsilyl ether was treated in benzene with pyridinium p-toluene sulfonate and then with magnesium sulfonate in the same way as in Example 37 to give 3 mg of the corresponding silyl ether (No. 763). This product was desilylated in the same way as in Example 33 to give 1.5 mg of the captioned compound No. 657.

NMR (CDCl$_3$)$\delta$:
0.85 (3H), 1.0–2.5 (26H), 3.67 (3H), 5.50 (2H).

EXAMPLE 44

Synthesis of (5E)-5-chloro-17(S),20-dimethyl-PGI$_2$ sodium salt (No. 701):

One milligram of (5E)-5-chloro-17(S),20-dimethyl-PGI$_2$ methyl ester was treated in the same way as in Example 35 to give a solution of the captioned compound No. 701.

EXAMPLE 45

Synthesis of (5E)-5-chloro-17(R),20-dimethyl-PGI$_2$ n-butyl ester (No. 667) and (5Z)-5-chloro-17(R),20-dimethyl PGI$_2$ n-butyl ester (No. 5Z-667):

(1) 25 mg of 5-chloro-17(R),20-dimethyl-$\Delta^6$-PGI$_1$ n-butyl ester 11,15-bis-t-butyldiphenylsilyl ether was treated in benzene with pyridinium p-toluenesulfonate and anhydrous magnesium sulfate in the same way as in Example 37 to give 6 mg of the corresponding (5E)-11,15-bis-t-butyldiphenylsilyl ether and 7 mg of the corresponding (5Z)-11,15-bis-t-butyldiphenylsilyl ether.

NMR (100 MHz, CDCl$_3$)$\delta$:

(5E)-5-chloro-17(R),20-dimethyl-PGI$_2$ n-butyl ester 11,15-bis-t-butyldiphenylsilyl ether (746), 0.8–1.1 (24H), 1.1–2.4 (28H), 3.70–4.3 (4H), 5.50 (2H), 7.3–7.7 (20H).

The NMR spectrum of the (5Z)-compound was almost the same as that of the (5E)-compound.

(2) Each of the compounds obtained in (1) above was treated with tetrabutyl ammonium fluoride in the same way as in Example 33 to desilylate it and to give 2 mg of the captioned compound No. 667 and 3 mg of the captioned compound No. 5Z-667. The NMR spectra of these products were much the same as those given in (1) above excepting the silyl group.

EXAMPLE 46

Synthesis of (5E)-5-chloro-13,14-dehydro-PGI$_2$ n-decyl ester (No. 677) and (5Z)-5-chloro-13,14-dehydro-PGI$_2$ n-decyl ester (No. 5Z-677):

(1) 35 mg of 5-chloro-13,14-dehydro-PGI$_2$ decyl ester 11,15-bis-t-butyldimethylsilyl ether was reacted in the same way as in Example 37 to give 7 mg of the corresponding (5E)-compound (No. 748) and 5 mg of the corresponding (5Z)-compound (No. 5Z-748).

(2) The products obtained in (1) above were each desilylated in the same way as in Example 33 to give 3 mg of the captioned compound No. 677 and 2 mg of the captioned compound No. 5Z-677.

NMR (100 MHz, CDCl$_3$)$\delta$ of No. 677:
0.8–2.2 (44H), 3.7–4.2 (4H), 4.5–4.7 (1H).

The NMR spectrum of the compound No. 5Z-677 was substantially the same as that of the compound No. 677.

EXAMPLE 47

Synthesis of (5E)-5-chloro-13,14-dihydro-PGI$_2$ methyl ester (No. 643):

4 mg of 5-chloro-13,14-dihydro-$\Delta^6$-PGI$_1$ methyl ester 11,15-bis-t-butyldimethylsilyl ether was treated in the same way as in Example 37 to give 2 mg of the corresponding 5E-silyl ether. The product was then treated in the same way as in Example 33 to remove the protective group and give 1 mg of the captioned compound No. 643.

NMR (100 MHz, CDCl$_3$) $\delta$:
0.85 (3H), 1.0–2.5 (26H), 3.65 (3H), 3.7–4.2 (2H), 4.4–4.7 (1H).

EXAMPLE 48

Synthesis of 7-chloro-$\Delta^6$-PGI$_1$ methyl ester 11,15-diacetate (No. 290):

7 mg of 7-chloro-PGI$_2$ methyl ester 11,15-diacetate was dissolved in 2 ml of chloroform, and one drop of conc. sulfuric acid was added through a capillary. The mixture was treated in the same way as in Example 32 to give 2 mg of the captioned compound No. 290.

NMR (100 MHz, CDCl$_3$) $\delta$:
0.88 (3H), 1.0–2.6 (25H), 3.67 (3H), 4.5–5.2 (3H), 5.55 (2H).

EXAMPLE 49

Synthesis of (5E)-5,7-dichloro-PGI$_2$ methyl ester 11,15-bis-t-butyldimethylsilyl ether (No. 762) and (5Z)-5,7-dichloro-PGI$_2$ methyl ester 11,15-bis-t-butyldimethylsilyl ether (No. 5Z-762):

11.1 mg of PGI$_2$ methyl ester 11,15-bis-t-butyldimethylsilyl ether was dissolved in 0.3 ml of dichloromethane, and then the solution was cooled to $-70°$ C. in an argon atmosphere. Then, 8 microliters of triethylamine was added. Furthermore, 38 microliters of t-butyl hypochlorite was added, and the mixture was stirred at −70° C. for 40 minutes. Then, a saturated aqueous solution of sodium bicarbonate was added, and the mixture was extracted with ethyl acetate twice. The extracts were combined, washed with a saturated aqueous solution of sodium chloride, and dried over magnesium sulfate. The solvent was distilled off, and the resulting crude product was purified by silica gel thin-layer chromatography using 8% ethyl acetate/hexane as a developing solvent to give 5,7-dichloro-PGI$_2$ methyl ester 11,15-bis-t-butyldimethylsilyl ether and (5Z)-5,7-dichloro-PGI$_2$ methyl ester 11,15-bis-t-butyldimethylsilyl ether, its isomer at the $\Delta^5$-double bond.

Compound A (less polar)

Amount yielded:
1.8 mg (yield 14%)
Silica gel TLC:
Rf=0.49 (10% ethyl acetate-hexane)
Mass (m/e):
607, 605, 571, 569.
NMR (CDCl$_3$) δ:
0.86 (9H, s), 0.91 (9H, s), 3.67 (3H, s), 3.6–4.2 (2H, m), 4.69 (1H, s), 4.8–5.1 (1H, br), 5.55 (2H, m).

Compound B (more polar)

Amount yielded:
3.0 mg (yield 23%)
Silica gel TLC:
Rf=0.42 (10% ethyl acetate-hexane)
Mass (m/e):
607, 605, 571, 569.
NMR (CDCl$_3$) δ:
0.86 (9H, s), 0.90 (9H, s), 3.67 (3H, s), 3.6–4.2 (2H, m), 4.79 (1H, s), 4.8–5.1 (1H, br), 5.55 (2H, m).

EXAMPLE 50

Synthesis of (5E)-5,7-dichloro-PGI$_2$ methyl ester (No. 642) and (5Z)-5,7-dichloro-PGI$_2$ methyl ester (No. 5Z-642):

(1) 1.8 mg of the compound A obtained in Example 49 was dissolved in 0.2 ml of tetrahydrofuran, and with ice cooling, 0.1 ml of a tetrahydrofuran solution of 5 mg of tetrabutyl ammonium fluoride was added. The mixture was stirred at room temperature for 1 hour. Immediately then, the reaction mixture was purified by Florisil column chromatography using ethyl acetate/hexane (=1:1) containing 0.1% of triethylamine to give 1.0 mg (yield 85%) of a compound C.
Mass (m/e):
379, 377, 361, 359, 343, 341, 325, 323.
NMR (CDCl$_3$) δ:
3.67 (3H, s), 3.6–4.2 (2H, m), 4.69 (1H, s), 4.8–5.1 (1H, br), 5.55 (2H, m).

(2) 1.8 mg of the compound B obtained in Example 49 was reacted in the same way as in (1) above, and purified by Florisil column chromatography using ethyl acetate/hexane (=1:1) containing 0.1% of triethylamine to give 1.0 mg (yield 85%) of a compound D.
Mass (m/e):
379, 377, 361, 359, 343, 341, 325, 323.
NMR (CDCl$_3$) δ:
3.67 (3H, s), 3.6–4.2 (2H, m), 4.79 (1H, s), 4.8–5.1 (1H, br), 5.55 (2H, m).

Either one of the compounds C and D is 5,7-dichloro-PGI$_2$ methyl ester, and the other is (5Z)-5,7-dichloro-PGI$_2$ methyl ester, i.e. an isomer at the $\Delta^5$-double bond.

EXAMPLE 51

Synthesis of a sodium salt of (5E)-5,7-dichloro-PGI$_2$ (No. 692), and a sodium salt of (5Z)-5,7-dichloro-PGI$_2$ (No. 5Z-692):

(1) 1.0 mg of the compound C obtained in Example 50 was stirred with 0.1 ml of a 1N aqueous solution of sodium hydroxide and 0.1 ml of ethanol at room temperature for 2 hours. Analysis of the reaction product by TLC led to the determination that the compound C changed to a more polar compound.

(2) 1.0 mg of the compound D obtained in Example 50 was reacted in the same way as in (1) above.

Either one of the solutions obtained in (1) and (2) above is a solution of a sodium salt of 5,7-dichloro-PGI$_2$, and the other is a solution of a sodium salt of (5Z)-5,7-dichloro-PGI$_2$, i.e. an isomer at the $\Delta^5$-double bond.

EXAMPLE 52

Synthesis of (5E)-5-bromo-7-chloro-PGI$_2$ methyl ester 11,15-diacetate (No. 745) and (5Z)-5-bromo-7-chloro-PGI$_2$ methyl ester 11,15-diacetate (No. 5Z-745):

6.7 microliters of triethylamine was added to 8.5 mg of 5-bromo-$\Delta^6$-PGI$_1$ methyl ester 11,15-diacetate, and 16 microliters of t-butyl hypochlorite was further added. The mixture was stirred at −40° C. for 1.5 hours and worked up in the same way as in Example 15. The resulting residue was purified by TLC to give 2 mg of the captioned compound No. 745 and 2.5 mg of the captioned compound No. 5Z-745.

Compound E (less polar)

Silica gel TLC:
Rf=0.51 (C$_6$H$_6$:EtOAc=17:3)
Mass (20 eV, m/e):
566, 564, 562, 528, 526, 504, 502, 483, 447, 444, 442, 408, 406, 363, 327.
NMR (CDCl$_3$) δ:
0.88 (3H), 1.2–1.7 (14H), 2.0–2.1 (6H), 2.3–3.0 (4H), 3.68 (3H), 4.77 (1H, s), 4.8–5.4 (3H), 5.55–5.7 (2H).

Compound F (more polar)

Silica gel TLC:
Rf=0.44 (C$_6$H$_6$:EtOAc=17:3)
Mass (20 eV, m/e):
566, 564, 528, 526, 504, 502, 483, 447, 408, 407, 406, 381, 363, 345, 344, 327, 227.
NMR (CDCl$_3$) δ:
0.88 (3H), 1.2–1.8 (14H), 1.95–2.1 (6H), 2.3–2.8 (4H), 3.67 (3H, s), 4.81 (1H, s), 4.7–5.4 (3H), 5.57–5.73 (2H, s).

EXAMPLE 53

Synthesis of (5E)-5-bromo-7-chloro-PGI$_2$ methyl ester (No. 683) and (5Z)-5-bromo-7-chloro-PGI$_2$ methyl ester (No. 5Z-683):

(5E)-5-bromo-7-chloro-PGI$_2$ methyl ester 11,15-diacetate and (5Z)-5-bromo-7-chloro-PGI$_2$ methyl ester 11,15-diacetate were each treated with sodium methoxide in methanol in the same way as in Example 40 to give the captioned compounds Nos. 683 and 5Z-683, respectively.

Compound G

NMR (CDCl$_3$) δ:

0.88 (3H), 1.0–2.8 (20H), 3.66 (3H), 3.7–4.3 (2H), 4.77 (1H), 4.6–4.9 (1H), 5.55–5.7 (2H).

Compound H

NMR (CDCl$_3$) δ:
0.88 (3H), 1.0–2.8 (20H), 3.68 (3H), 3.7–4.2 (2H), 4.81 (1H), 4.7–4.9 (1H), 5.55–4.75 (2H).

EXAMPLE 54

Synthesis of 7-bromo-5-chloro-PGI$_2$ methyl ester 11,15-diacetate (No. 770):

15 mg of 5-chloro-Δ$^6$-PGI$_1$ methyl ester 11,15-diacetate was dissolved in 3 ml of dichloromethane, and 100 mg of anhydrous potassium carbonate was added. With stirring, a solution of 9 mg of N-bromosuccinimide in 3 ml of dichloromethane was added. The mixture was stirred at room temperature for 20 hours. An aqueous solution of sodium bicarbonate was added, and the mixture was extracted with diethyl ether. The aqueous layer was extracted with diethyl ether. The ethereal layers were combined, washed with a saturated aqueous solution of sodium chloride, dried over anhydrous magnesium sulfate, filtered and concentrated. The residue was chromatographed on a column of Florisil (3 g) using hexane/ethyl acetate/triethylamine (=100:10:0.1) as an eluent to give 10 mg (more polar, yield 58%) and 6.4 mg (less polar, yield 38%) of 7-bromo-5-chloro-PGI$_2$ methyl ester 11,15-diacetate.

Less polar product:
Silicagel TLC:
  Rf=0.38 (C$_6$H$_6$:EtOAc=4:1)
NMR (CDCl$_3$) δ:
0.87 (t, 3H), 1.0–1.8 (m, 8H), 1.99 (s, 3H), 2.03 (s, 3H), 1.8–3.1 (m, 10H), 3.70 (s, 3H), 4.84 (s, 1H), 4.6–5.8 (m, 3H), 5.4–5.7 (m, 2H).
Mass (20 eV, m/e):
566, 564, 562, 506, 504, 502, 486, 484, 482, 364, 362.
More polar product:
Silicagel TLC:
  Rf=0.30 (C$_6$H$_6$:EtOAc=4:1)
NMR (CDCl$_3$) δ:
0.87 (t, 3H), 1.0–1.8 (m, 8H), 1.99 (s, 3H), 2.04 (s, 3H), 1.8–3.0 (m, 10H), 3.69 (s, 3H), 4.88 (s, 1H), 4.6–5.7 (m, 3H), 5.4–5.7 (m, 2H).
Mass (20 eV, m/e):
566, 564, 562, 506, 504, 502, 486, 484, 482, 364, 362.

EXAMPLE 55

Synthesis of 7-fluoro-PGI$_2$ methyl ester 11,15-bis-t-butyl-dimethylsilyl ether (No. 758) and 5-fluoro-Δ$^6$-PGI$_1$ methyl ester 15-bis-t-butyldimethylsilyl ether (No. 318):

15 mg of 5-bromo-Δ$^6$-PGI$_1$ methyl ester 11,15-bis-t-butyl-dimethylsilyl ether was dissolved in 1 ml of acetonitrile, 10 mg of potassium carbonate was added, and then 50 mg of silver fluoride was further added. The mixture was stirred at room temperature for 1 hour. Methylene chloride was added to the reaction mixture, and the mixture was filtered through a Celite-glass filter. The filtrate was washed with methylene chloride, and then the methylene chloride was distilled off to give 13 mg of a crude product. The crude product was purified by silica gel thin-layer chromatography using 10% ethyl acetate/hexane as a developing solvent to give the captioned compounds Nos. 758 and 318.

Compound No. 758

Amount yielded:
5.0 mg (yield 36%)
Mass spectrum:
(m/e) 612 (M+), 592, 555, 535.
NMR (100 MHz, CDCl$_3$) δppm:
0.86 (9H, s), 0.90 (9H, s), 3.66 (3H, s), 3.7–4.2 (2H, m), 4.6–4.9 (1H, m), 4.71 (1H, t, J=7 Hz), 4.91 (1H, d, J=56 Hz), 5.52 (2H, m).

Compound No. 318

Amount yielded:
2.0 g (yield 14%)
Mass (m/e):
612 (M+), 592, 555.
NMR (100 MHz, CDCl$_3$, ppm) δ:
0.86 (9H, s), 0.89 (9H, s), 2.7–3.1 (1H, br), 3.68 (3H, s), 3.6–4.1 (2H, m), 4.5–5.3 (3H, m), 5.47 (2H, m).

EXAMPLE 56

Synthesis of 7-fluoro-PGI$_2$ methyl ester 11,15-diacetate (No. 756) and 5-fluoro-Δ$^6$-PGI$_1$ methyl ester 11,15-diacetate (No. 308):

10.7 mg of 5-bromo-Δ$^6$-PGI$_1$ methyl ester 11,15-diacetate was dissolved in 1 ml of dry acetonitrile, and 30 mg of silver fluoride was added. The mixture was stirred at room temperature for 1 hour. Methylene chloride was added to the reaction mixture, and the mixture was filtered through a Celite-glass filter. The filtrate was washed with methylene chloride, and the methylene chloride was distilled off to give 15 mg of a crude product. The crude product was separated by silica gel thin-layer chromatography using 15% ethyl acetate/benzene as a developing solvent to give the captioned compounds Nos. 756 and 308.

Compound No. 756

Amount yielded:
3.5 mg (yield 37%)
Mass (m/e):
468 (M+), 448, 408, 388, 348, 328.
NMR (100 MHz, CDCl$_3$) δ:
2.01 (3H, s), 2.04 (3H, s), 3.66 (3H, s), 4.77 (1H, t, J=7 Hz), 4.75–5.30 (3H, m), 4.94 (1H, d, J=56 Hz), 5.5–5.65 (2H, m).

Compound No. 308

Amount yielded: 1.6 mg (yield 17%)
Mass (m/e):
468 (M+), 448, 408, 388, 348, 328.
NMR (100 MHz, CDCl$_3$) δ:
1.99 (3H, s), 2.04 (3H, s), 2.9–3.2 (1H, br), 3.67 (3H, s), 4.5–5.3 (5H, m), 5.45–5.55 (2H, m).

EXAMPLE 57

Synthesis of 7-fluoro-PGI$_2$ methyl ester 11,15-diacetate (No. 756) and 5-fluoro-Δ$^6$-PGI$_1$ methyl ester 11,15-diacetate (No. 308):

15 mg of 5-chloro-Δ$^6$-PGI$_1$ methyl ester 11,15-diacetate was dissolved in dry acetonitrile, and two drops of triethylamine were added. Then, 80 mg of silver fluoride was added, and the mixture was stirred at room temperature for 2 days. The reaction mixture was worked up in the same way as in Example 56, and separated by silica gel thin-layer chromatography using 15% ethyl acetate/benzene as a developing solvent to give 1.8 mg (yield 12%) of the captioned compound No. 756 and 0.9 mg (yield 6%) of the captioned compound No. 308.

EXAMPLE 58

Synthesis of 7-fluoro-PGI$_2$ methyl ester (No. 637):

0.6 ml of dry methanol containing 0.022 millimole of sodium methoxide cooled to $-40°$ C. was added to 2 mg of 7-fluoro-PGI$_2$ methyl ester 11,15-diacetate, and the mixture was left to stand at $-20°$ C. for 16 hours. 10 ml of a dilute aqueous solution of sodium bicarbonate was added to the reaction mixture, and the mixture was extracted with 10 ml of ethyl acetate twice. The extracts were combined, washed with 8 ml of water, and dried over magnesium sulfate-potassium carbonate. The solvent was distilled off under reduced pressure to give 1.2 mg (yield 73%) of the captioned compound No. 637.

Mass (20 eV, m/e):

384 (M+), 366, 364, 346, 333, 317, 263.

NMR (100 MHz, CDCl$_3$) $\delta$:

3.67 (3H, s), 3.8–4.2 (2H, m), 4.68 (1H, t, J=7 Hz), 4.7–5.0 (1H, br), 4.93 (1H, d, J=56 Hz), 5.5–5.7 (2H, m).

EXAMPLE 59

Synthesis of 5-fluoro-$\Delta^6$-PGI$_1$ methyl ester (No. 220):

Dry methanol containing 0.027 millimole of sodium methoxide was added to 3 mg of 5-fluoro-$\Delta^6$-PGI$_1$ methyl ester 11,15-diacetate, and the mixture was left to stand at $-20°$ C. for 14 hours. To the reaction mixture was added 10 ml of a dilute aqueous solution of sodium bicarbonate, and the mixture was extracted with 10 ml of ethyl acetate twice. The extracts were combined, washed with 8 ml of water and dried over magnesium sulfate-potassium carbonate. The solvent was distilled off under reduced pressure to give 2.1 mg (yield 85%) of the captioned compound No. 220.

Mass (20 eV, m/e):

384 (M+), 366, 364, 346, 333, 317, 263

NMR (100 MHz, CDCl$_3$) $\delta$:

2.85–3.2 (1H, br), 3.68 (3H, s), 3.65–4.2 (2H, m), 4.92 (1H, broad doublet, J=46 Hz), 4.8–5.2 (2H, m), 5.45–5.6 (2H, m).

EXAMPLE 60

Synthesis of 7-fluoro-PGI$_2$ methyl ester (No. 637):

One milliliter (0.02 millimole) of a 0.02M tetrahydrofuran solution of tetrabutyl ammonium fluoride/triethylamine (1:1 by mole) was added to 1 mg (0.0016 millimole) of 7-fluoro-PGI$_2$ methyl ester 11,15-bis-t-butyldimethylsilyl ether, and the reaction was carried out at room temperature for 2 hours. After the reaction, the solvent was distilled off, and ethyl acetate and a saturated aqueous solution of ammonium sulfate containing a small amount of triethylamine were added to perform extraction. The organic layer was washed with water and worked up in a customary manner to give 0.5 mg (yield 81%) of the captioned compound No. 637.

EXAMPLE 61

Synthesis of a sodium salt of 7-fluoro-PGI$_2$ (No. 688):

1.2 mg of 7-fluoro-PGI$_2$ methyl ester was dissolved in 0.5 ml of ethanol, and 0.15 ml of a 0.1N aqueous solution of sodium hydroxide was added. The mixture was left to stand at room temperature for 12 hours. The reaction was monitored by silica gel thin-layer chromatography (dichlormethane/acetone=7:3), and it was ascertained that the hydrolysis of the ester proceeded completely. Thus, a solution of the desired sodium salt of the compound No. 688 was obtained.

EXAMPLE 62

Synthesis of a sodium salt of 5-fluoro-$\Delta^6$-PGI$_1$ (No. 348):

2.1 mg of 5-fluoro-$\Delta^6$-PGI$_1$ methyl ester was dissolved in 0.5 ml of ethanol, and 0.27 ml of a 0.1N aqueous solution of sodium hydroxide was added. The mixture was left to stand at room temperature for 12 hours. The reaction was monitored by silica gel thin-layer chromatography (dichloromethane/acetone=7:3), and it was found that the hydrolysis of the ester proceeded completely. Thus, a solution of the sodium salt of the captioned compound No. 348 was obtained.

EXAMPLE 63

Synthesis of 7-fluoro-PGI$_2$ (No. 501):

10 mg of 7-fluoro-PGI$_2$ methyl ester obtained in Example 60 was dissolved in 0.5 ml of methanol, and 0.3 ml of a 0.1N aqueous solution of sodium hydroxide was added. The mixture was stirred overnight at room temperature, and concentrated. Water and ethyl acetate were added, and the mixture was transferred to a separating funnel. An aqueous solution of oxalic acid was added while shaking the separating funnel. The pH of the aqueous layer was adjusted to about 3. The organic layer was dried over anhydrous sodium sulfate, and the solvent was distilled off under reduced pressure to give a residue containing 8 mg of 7-fluoro-PGI$_2$. Diethyl ether was added to the residue, and a diethyl ether solution of diazomethane was added. The mixture was stirred at room temperature for 10 minutes. The solvent was distilled off, and the residue was purified by thin-layer chromatography to give 3 mg of 7-fluoro-PGI$_2$ methyl ester. This led to the determination that 7-fluoro-PGI$_2$ was formed.

EXAMPLE 64

Synthesis of 5-fluoro-$\Delta^6$-PGI$_1$ (100):

10 mg of the 5-fluoro-$\Delta^6$-PGI$_1$ methyl ester obtained in Example 59 was dissolved in 0.5 ml of methanol, and 0.3 ml of a 0.1N aqueous solution of sodium hydroxide was added. The mixture was stirred at room temperature for 6 hours, and worked up in the same way as in Example 63 to give a residue containing 8 mg of 5-fluoro-$\Delta^6$-PGI$_1$. When the residue was converted to a methyl ester in the same way as in Example 63, 3.2 mg of 5-fluoro-$\Delta^6$-PGI$_1$ methyl ester was obtained. This fact led to the determination that 5-fluoro-$\Delta^6$-PGI$_1$ was formed.

EXAMPLE 65

5-fluoro-17(R),20-dimethyl-$\Delta^6$-PGI$_1$ n-butyl ester 11,15-bis-t-butyldimethylsilyl ether (No. 321) and 7-fluoro-17(R),20-dimethyl PGI$_2$ n-butyl ester 11,15-bis-t-butyldimethylsilyl ether (No. 766):

15 mg of the 5-bromo-17(R),20-dimethyl-$\Delta^6$-PGI$_1$ n-butyl ester bis-t-butyldimethylsilyl ether synthesized in Example 9 was dissolved in 1 ml of acetonitrile, and 10 mg of potassium carbonate and then 20 mg of silver fluoride were added. The mixture was stirred at room temperature for 2 hours, and worked up in the same way as in Example 55. The resulting residue was separated by thin-layer chromatography using 10% ethyl acetate/n-hexane as a developing solvent to give the captioned compounds Nos. 321 and 766.

Compound No. 321

Amount yielded:

2.2 mg
NMR (CDCl$_3$) δ:
0.88 (3H, s), 3.7–4.2 (4H, m), 4.6–5.3 (3H, m), 5.4–5.6 (2H, m).

Compound No. 766

Amount yielded:
3.7 mg
NMR (CDCl$_3$) δ:
0.88 (18H, s), 3.7–4.2 (4H, m), 4.6–5.3 (3H, m), 5.5–5.65 (2H, m).

EXAMPLE 66

Synthesis of 5-fluoro-17(R),20-dimethyl-Δ$^6$-PGI$_1$ n-butyl ester (No. 259):

2.2 mg of the 5-fluoro-17(R),20-dimethyl-Δ$^6$-PGI$_1$ n-butyl ester 11,15-bis-t-butyldimethylsilyl ether obtained in Example 65 was treated with tetrabutyl ammonium fluoride and triethylamine in tetrahydrofuran in the same way as in Example 60 to desilylate it and give 1.2 mg of the captioned compound No. 259.

NMR (CDCl$_3$) δ:
3.7–4.2 (4H, m), 4.6–5.3 (3H, m), 5.4–5.6 (2H, m).

EXAMPLE 67

Synthesis of 7-fluoro-17(R),20-dimethyl PGI$_2$ n-butyl ester (No. 681):

3.7 mg of 7-fluoro-17(R),20-dimethyl PGI$_2$ n-butyl ester bis-t-butyldimethylsilyl ether obtained in Example 65 was desilylated in the same way as in Example 60 to give 3.0 mg of the captioned compound No. 181.

NMR (CDCl$_3$) δ:
3.7–4.2 (4H, m), 4.6–5.3 (3H, m), 5.5–5.65 (2H, m).

EXAMPLE 68

Synthesis of 5-fluoro-17(R),20-dimethyl-Δ$^6$-PGI$_1$ sodium salt (No. 324):

The 5-fluoro-17(R),20-dimethyl-Δ$^6$-PGI$_1$ n-butyl ester obtained in Example 66 was treated in the same way as in Example 62 to give a solution of the captioned compound No. 324.

EXAMPLE 69

Synthesis of 7-fluoro-17(R),20-dimethyl PGI$_2$ sodium salt (No. 698):

The 7-fluoro-17(R),20-dimethyl PGI$_2$ methyl ester obtained in Example 65 was treated in the same way as in Example 62 to give a solution of the captioned compound No. 698.

EXAMPLE 70

Synthesis of 5-fluoro-16,16-dimethyl-Δ$^6$-PGI$_1$ methyl ester 11,15-diacetate (No. 303) and 7-fluoro-16,16-dimethyl PGI$_2$ methyl ester 11,15-diacetate (No. 764):

7 mg of the 5-bromo-16,16-dimethyl-Δ$^6$-PGI$_1$ methyl ester 11,15-diacetate obtained in Example 10 was dissolved in 0.5 ml of acetonitrile, and 10 microliters of triethylamine was added. Then, 10 ml of silver fluoride was added, and the mixture was stirred at room temperature for 3 hours. The reaction mixture was worked up in the same way as in Example 55. The resulting residue was separated by thin-layer chromatography using 15% ethyl acetate/benzene as a developing solvent to give 2 mg of the captioned compound No. 303 and 3 mg of the captioned compound No. 764.

Compound No. 303

NMR (CDCl$_3$) δ:
1.99 (3H, s), 2.04 (3H, s), 2.9–3.2 (1H, br), 3.67 (3H, s), 4.5–5.3 (5H, m), 5.45–5.55 (2H, m).

Compound No. 764

NMR (CDCl$_3$) δ:
2.01 (3H, s), 2.03 (3H, s), 3.67 (3H, s), 4.75 (1H, t, J=7 Hz), 4.73–5.30 (4H, m), 5.5–5.65 (2H, m).

EXAMPLE 71

Synthesis of 5-fluoro-16,16-dimethyl-Δ$^6$-PGI$_1$ methyl ester (No. 273):

2 mg of the 5-fluoro-16,16-dimethyl-Δ$^6$-PGI$_1$ methyl ester 11,15-diacetate obtained in Example 70 was treated with sodium methoxide in methanol in the same way as in Example 59 to give 1.6 mg of the captioned compound No. 273.

NMR (100 MHz, CDCl$_3$) δ:
2.9–3.2 (1H, br), 3.67 (3H, s), 3.7–4.2 (2H, m), 4.5–5.3 (3H, m), 5.45–5.55 (2H, m).

EXAMPLE 72

Synthesis of 7-fluoro-16,16-dimethyl PGI$_2$ methyl ester (No. 635):

3 mg of the 7-fluoro-16,16-dimethyl PGI$_2$ methyl ester 11,15-diacetate obtained in Example 70 was treated with sodium methoxide in methanol in the same way as in Example 59 to deacetylate it and give 2.2 mg of the captioned compound No. 635.

NMR (100 MHz, CDCl$_3$) δ:
3.66 (3H, s), 3.7–4.2 (2H, m), 4.6–5.3 (3H, m), 5.5–5.65 (2H, m).

EXAMPLE 73

Synthesis of 5-fluoro-16,16-dimethyl-Δ$^6$-PGI$_1$ sodium salt (No. 346):

1.6 mg of the 5-fluoro-16,16-dimethyl-Δ$^6$-PGI$_1$ methyl ester obtained in Example 71 was treated with sodium hydroxide in ethanol-water in the same way as in Example 62 to give a solution of the captioned compound No. 346.

EXAMPLE 74

Synthesis of 7-fluoro-16,16-dimethyl PGI$_2$ sodium salt (No. 697):

2.2 mg of the 7-fluoro-16,16-dimethyl PGI$_2$ methyl ester obtained in Example 72 was treated with sodium hydroxide in ethanol-water in the same way as in Example 62 to give a solution of the captioned compound No. 697.

EXAMPLE 75

Synthesis of 5-fluoro-15-cyclohexyl-16,17,18,19,20-pentanor-Δ$^6$-PGI$_1$ n-decyl ester 11,15-diacetate (No. 304) and 7-fluoro-15-cyclohexyl-16,17,18,19,20-pentanor PGI$_2$ n-decyl ester 11,15-diacetate (No. 754):

25 mg of the 5-bromo-15-cyclohexyl-16,17,18,19,20-pentanor-Δ$^6$-PGI$_1$ n-decyl ester diacetate obtained in Example 11 was dissolved in 2 ml of acetonitrile, and 5 mg of sodium carbonate and then 20 mg of silver fluoride were added. The mixture was stirred at room temperature for 1 hour, and worked up in the same way as in Example 55. The residue was separated by thin-layer chromatography using 10% ethyl acetate/benzene as a developing solvent to give 5 mg of the captioned compound No. 304 and 8.6 mg of the captioned compound No. 754.

Compound No. 304

NMR (100 MHz, CDCl$_3$) δ:
1.99 (3H, s), 2.03 (3H, s), 2.9–3.2 (1H, br), 4.07 (2H, t, J=6 Hz), 4.5–5.3 (5H, m), 5.45–5.55 (2H, m).

Compound No. 754

NMR (100 MHz, CDCl$_3$) δ:
2.00 (3H, s), 2.04 (3H, s), 4.07 (2H, t, J=6 Hz), 4.6–5.3 (5H, m), 5.5–5.65 (2H, m).

EXAMPLE 76

Synthesis of 5-fluoro-15-cyclohexyl-16,17,18,19-20-pentanor-Δ$^6$-PGI$_1$ n-decyl ester (No. 275):

5 mg of the 5-fluoro-15-cyclohexyl-16,17,18,19-20-pentanor-Δ$^6$-PGI$_1$ n-decyl ester 11,15-diacetate obtained in Example 75 was treated with sodium methoxide in methanol in the same way as in Example 59 to give 4 mg of the captioned compound No. 275.

NMR (100 MHz, CDCl$_3$) δ:
2.9–3.2 (1H, br), 3.7–4.3 (4H, m), 4.5–5.3 (3H, m), 5.45–5.55 (2H, m).

EXAMPLE 77

Synthesis of 7-fluoro-15-cyclohexyl-16,17,18,19,20-pentanor-PGI$_2$ n-decyl ester (No. 679):

5 mg of the 7-fluoro-15-cyclohexyl-16,17,18,19,20-pentanor-PGI$_2$ n-decyl ester 11,15-diacetate was treated with sodium methoxide in methanol in the same way as in Example 59 to give 3.8 mg of the captioned compound No. 679.

NMR (100 MHz, CDCl$_3$) δ:
3.7–4.3 (4H, m), 4.6–5.3 (3H, m), 5.5–5.65 (2H, m).

EXAMPLE 78

Synthesis of 5-fluoro-15-cyclohexyl-16,17,18,19,20-pentanor-Δ$^6$-PGI$_1$ sodium salt (No. 340) and 7-fluoro-15-cyclohexyl-16,17,18,19,20-pentanor PGI$_2$ sodium salt (No. 695):

4 mg of the 5-fluoro-15-cyclohexyl-16,17,18,19,20-pentanor-Δ$^6$-PGI$_1$ n-decyl ester 11,15-diacetate was dissolved in 1 ml of ethanol, and 1 ml of a 0.01N aqueous solution of sodium hydroxide was added. The mixture was treated in the same way as in Example 62 to give a solution of the captioned compound No. 340.

Similarly, a solution of the captioned compound No. 695 was prepared from 4 mg of the 7-fluoro-15-cyclohexyl-16,17,18,19,20-pentanor PGI$_2$ n-decyl ester 11,15-diacetate obtained in Example 75.

EXAMPLE 79

Synthesis of 5-fluoro-17(S),20-dimethyl-Δ$^6$-PGI$_1$ methyl ester (No. 233) and 7-fluoro-17(S), 20-dimethyl-PGI$_2$ methyl ester (No. 655):

(1) 15 mg of the 5-bromo-Δ$^6$-PGI$_1$ methyl ester 11,15-bis-t-butyldiphenylsilyl ether obtained in Example 13 was dissolved in 1 ml of acetonitrile, and a few drops of triethylamine were added. Then, 20 mg of silver fluoride was added, and the mixture was stirred at room temperature for 1 hour. The reaction mixture was worked up in the same way as in Example 55 and separated by thin-layer chromatography chromatography using 5% ethyl acetate/n-hexane as a developing solvent to give 2 mg of 5-fluoro-17(S),20-dimethyl-Δ$^6$-PGI$_1$ methyl ester 11,15-bis-t-butyldimethylsilyl ether and 4.2 g of 7-fluoro-17(S),20-dimethyl PGI$_2$ methyl ester 11,15-bis-t-butyldiphenyl ether.

(2) Each of the compounds obtained in (1) above was treated with tetrabutyl ammonium fluoride-triethylamine in tetrahydrofuran in the same way as in Example 60 to desilylate it. Thus, 1.0 mg of the captioned compound No. 233 and 3.0 mg of the captioned compound No. 655 were obtained.

Compound No. 233

NMR (CDCl$_3$)δ:
2.9–3.3 (1H, br), 3.66 (3H, s), 3.7–4.2 (2H, m), 4.5–5.3 (3H, m), 5.45–5.55 (2H, m).

Compound No. 655

NMR (CDCl$_3$)δ:
3.66 (3H, s), 3.7–4.2 (2H, m), 4.6–5.3 (3H, m), 5.5–5.65 (2H, m).

EXAMPLE 80

Synthesis of 5-fluoro-17(S),20-dimethyl-Δ$^6$-PGI$_1$ sodium salt (No. 326):

1.0 mg of the 5-fluoro-17(S),20-dimethyl-Δ$^6$-PGI$_1$ methyl ester obtained in Example 79 was treated in the same way in Example 62 to give a solution of the captioned compound No. 326.

EXAMPLE 81

Synthesis of 7-fluoro-17(S),20-dimethyl-PGI$_2$ sodium salt (No. 691):

2.0 mg of the 7-fluoro-17(S),20-dimethyl PGI$_2$ methyl ester obtained in Example 79 was treated in the same way as in Example 62 to give a solution of the captioned compound No. 691.

EXAMPLE 82

Synthesis of 5-fluoro-13,14-dehydro-Δ$^6$-PGI$_1$ n-butyl ester (No. 247) and 7-fluoro-13,14-dehydro-PGI$_2$ n-butyl ester (No. 665):

(1) 12 mg of the 5-bromo-13,14-dehydro-Δ$^6$-PGI$_1$ n-butyl ester 11,15-diacetate obtained in Example 12 was dissolved in 0.8 ml of acetonitrile, and 5 mg of potassium carbonate and then 8 mg of silver fluoride were added. The mixture was stirred at room temperature for 5 hours. Methylene chloride was added, and the mixture was filtered through Celite. The solvent was distilled off, and the residue was separated by thin-layer chromatography to give 2 mg of 5-fluoro-13,14-dehydro-Δ$^6$-PGI$_1$ n-butyl ester 11,15-diacetate and 3 mg of 7-fluoro-13,14-dehydro-PGI$_2$ n-butyl ester 11,15-diacetate.

(2) The compounds obtained in (1) above were each treated with sodium methoxide in methanol in the same way as in Example 59 to deacetylate them to give 1.5 mg of the captioned compound No. 247 and 2.3 mg of the captioned compound No. 665.

Compound No. 247

NMR (CDCl$_3$)δ:
3.7–4.2 (4H, m), 4.6–5.3 (3H, m).

Compound No. 665

NMR (CDCl$_3$)δ: 3.7–4.2 (4H, m), 4.6–5.3 (3H, m).

EXAMPLE 83

Synthesis of 5-fluoro-13,14-dehydro-Δ$^6$-PGI$_1$ sodium salt (No. 328):

1.2 mg of the 5-fluoro-13,14-dehydro-Δ$^6$-PGI$_1$ n-butyl ester obtained in Example 82 was dissolved in 0.5 ml of methanol, and then 0.1 ml of a 0.05N aqueous solution of sodium hydroxide was added, the mixture was stirred at room temperature for 8 hours. The reaction was monitored by thin-layer chromatography to determine that the desired compound (No. 328) was formed.

EXAMPLE 84

Synthesis of 7-fluoro-13,14-dehydro-PGI$_2$ sodium salt (No. 693):

2.0 mg of 7-fluoro-13,14-dehydro-PGI$_2$ n-butyl ester obtained in Example 82 was dissolved in 0.5 ml of ethanol, and then 0.15 ml of a 0.05N aqueous solution of sodium hydroxide was added. The mixture was worked up in the same way as in Example 62 to give a solution of the captioned compound No. 693.

EXAMPLE 85

Synthesis of 7-fluoro-PGI$_2$ methyl ester 11,15-bis-t-butyl-dimethylsilyl ether (No. 758) and 5-fluoro-$\Delta^6$-PGI$_1$ methyl ester 11,15-bis-t-butyldimethylsilyl ether (No. 318):

18 mg of 7-bromo-PGI$_2$ methyl ester 11,15-bis-t-butyldimethylsilyl ether was reacted with 50 mg of silver fluoride in 2 ml of acetonitrile in the same way as in Example 55 to give 5.5 mg of the captioned compound No. 758 and 3.5 mg of the captioned compound No. 318.

EXAMPLE 86

Synthesis of 7-fluoro-$\Delta^6$-PGI$_1$ methyl ester (No. 221):

(1) 10 mg of 7-fluoro-PGI$_2$ methyl ester 11,15-bis-t-butyldimethylsilyl ether was dissolved in 0.5 ml of benzene, and 2 mg of pyridinium p-toluenesulfonate was added. The mixture was stirred overnight. Then, 200 mg of anhydrous magnesium sulfate was added, and the mixture was refluxed for 3 hours. The product was worked up in the same way as in Example 37 to give 4 mg of 7-fluoro-$\Delta^6$-PGI$_1$ methyl ester 11,15-bis-t-butyl-dimethylsilyl ether.

(2) The product obtained in (1) above was desilylated in the same way as in Example 60 to give 2.8 mg of the captioned compound No. 221.

NMR (CDCl$_3$)$\delta$:
2.9–3.2 (1H, br), 3.67 (3H, s), 3.7–4.2 (2H, m), 4.7–5.0 (1H, br), 5.5–5.7 (2H, m).

EXAMPLE 87

Synthesis of 7-fluoro-$\Delta^6$-PGI$_1$ sodium salt (No. 342):

2 mg of the 7-fluoro-$\Delta^6$-PGI$_1$ methyl ester obtained in Example 86 was treated in the same way as in Example 83 to give a solution of the captioned compound No. 342.

EXAMPLE 88

Synthesis of 7-fluoro-17(R),20-dimethyl-$\Delta^6$-PGI$_1$ methyl ester (No. 231):

10 mg of the 7-fluoro-17(R),20-dimethyl-PGI$_2$ methyl ester 11,15-bis-t-butyldimethylsilyl ether obtained in Example 65 was treated in the same way as in Example 37 to give 4.2 mg of a bis-t-butyldimethylsilyl ether of the captioned compound. The ether was desilylated in the same way as in Example 60 to give 3.0 mg of the captioned compound No. 231.

NMR (CDCl$_3$)$\delta$:
2.9–3.2 (1H, br), 3.67 (3H, s), 3.7–4.2 (2H, m), 4.7–5.0 (1H, br), 5.5–5.7 (2H, m).

EXAMPLE 89

Synthesis of 7-fluoro-17(R),20-dimethyl-$\Delta^6$-PGI$_1$ sodium salt (No. 344):

When 1.0 mg of the 7-fluoro-17(R),20-dimethyl-$\Delta^6$-PGI$_1$ methyl ester obtained in Example 88 was treated in the same way as in Example 83, a solution of the captioned compound No. 344 was obtained.

EXAMPLE 90

Synthesis of (5E)-7-chloro-5-fluoro-PGI$_2$ methyl ester 11,15-diacetate (No. 768) and (5Z)-7-chloro-5-fluoro-PGI$_2$ methyl ester 11,15-diacetate (No. 5Z-671):

10 microliters of triethylamine was added to 10 mg of 5-fluoro-$\Delta^6$-PGI$_1$ methyl ester 11,15-diacetate, and the mixture was dissolved in 1 ml of methylene chloride. The solution was cooled to $-40°$ C., and 15 microliters of t-butyl hypochlorite was added. The mixture was stirred at $-40°$ C. for 40 minutes and then at room temperature for 30 minutes. A saturated aqueous solution of sodium bicarbonate was added, and the mixture was extracted with diethyl ether twice. The extracts were combined, and washed with brine and dried over potassium carbonate-magnesium sulfate. The solvent was then distilled off. The residue was separated by thin-layer chromatography using 15% ethyl acetate/benzene as a developing solvent to give 2 mg of compound I and 4 mg of compound J.

Compound I (less polar)

Mass spectrum (m/e):
504, 502 (M+).
NMR (CDCl$_3$)$\delta$:
3.67 (3H, s), 4.6–5.3 (4H, m), 5.5–5.65 (2H, m).

Compound J (more polar)

Mass (m/e):
504, 502 (M+)
NMR (CDCl$_3$)$\delta$:
3.67 (3H, s), 4.6–5.3 (4H, m), 5.5–5.7 (2H, m).

EXAMPLE 91

Synthesis of (5E)-7-chloro-5-fluoro-PGI$_2$ sodium salt (No. 687) and (5Z)-7-chloro-5-fluoro-PGI$_2$ sodium salt (No. 5Z-687):

By hydrolyzing (5E)-7-chloro-5-fluoro-PGI$_2$ methyl ester 11,15-diacetate and (5Z)-7-chloro-5-fluoro-PGI$_2$ methyl ester 11,15-diacetate in the same way as in Example 83, solutions of the captioned compounds Nos. 687 and 5Z-687 were obtained respectively.

EXAMPLE 92

Synthesis of 7-bromo-5-fluorl-PGI$_2$ methyl ester 11,15-diacetate (No. 757):

5-Fluoro-$\Delta^6$-PGI$_1$ methyl ester 11,15-diacetate is dissolved in methylene chloride, and a small amount of triethylamine is added. The mixture is cooled to $-40°$ C., and t-butyl hypobromite is added. The mixture is stirred at $-40°$ C. to room temperature, and worked up in the same way as in Example 7 to give the captioned compound No. 757.

EXAMPLE 93

(1) Synthesis of 5,7-difluoro-PGI$_2$ methyl ester 11,15-diacetate (No. 743):

7-Bromo-5-fluoro-PGI$_2$ methyl ester 11,15-diacetate is fluorinated with silver fluoride in the same way as in Example 55 to give the captioned compound.

(2) Synthesis of 5,7-difluoro-PGI$_2$ methyl ester (No. 640):

5,7-Difluoro-PGI$_2$ methyl ester 11,15-diacetate is treated with sodium methoxide in methanol in the same way as in Example 58 to give the captioned compound.

(3) Synthesis of 5,7-difluoro-PGI$_2$ sodium salt (No. 705):

5,7-Difluoro-PGI$_2$ methyl ester is treated with sodium hydroxide in ethanol-water in the same way as in Example 61 to give a solution of the captioned compound.

EXAMPLE 94

Synthesis of 7-hydroxy-PGI$_2$ methyl ester 11,15-bis-t-butyl dimethylsilyl ether (No. 800):

(1) 0.5 ml of a benzene solution of 14 mg (0.10 millimole) of benzenesulfenyl chloride was added dropwise at 0° to 5° C. to 1 ml of a benzene solution of 56 mg (0.09 millimole) of PGI$_2$ methyl ester 11,15-bis-t-butyldimethyldimethylsilyl ether and 30 mg (0.30 millimole) of triethylamine. After the reaction, a saturated aqueous solution of sodium bicarbonate was added to the reaction mixture, and the mixture was extracted with hexane. The extract was dried over anhydrous magnesium sulfate-anhydrous potassium carbonate, and worked up in a customary manner to give 80 mg of a crude product. The crude product was purified by silica gel column chromatography using hexane (containing 0.1% of triethylamine) as an eluent to give 38 mg (yield 60%) of 5-phenylthio-$\Delta^6$-PGI$_1$ methyl ester 11,15-bis-t-butyl-dimethylsilyl ether.

Mass (20 eV, m/e):
702 (M+),
NMR (CDCl$_4$)$\delta$:
0.08 (12H, bs), 0.9 (21H, bs), 1.1–2.8 (18H), 3.60 (3H, s), 3.7 (1H, m), 4.1 (2H, m), 4.65 (1H, d, J=3 Hz), 4.75 (1H, m), 5.43 (2H, m), 7.1–7.5 (5H, m).

(2) 90 mg (0.128 millimole) of crude 5-phenylthio-$\Delta^6$-PGI$_1$ methyl ester 11,15-bis-t-butyldimethylsilyl ether was dissolved in 5 ml (0.05 mole) of sodium bicarbonate and 3 ml of methylene chloride, and with vigorous stirring, 24 mg (0.14 millimole) of m-chloroperbenzoic acid was added. The reaction was performed for 20 minutes. The organic layer was separated, and the aqueous layer was extracted with methylene chloride. The organic layers were combined, and washed with a saturated aqueous solution of ammonium sulfate. Then, one drop of triethylamine was added, and the organic layer was dried over anhydrous magnesium sulfate-potassium carbonate. The crude product was purified in a customary manner to give 118 mg (0.123 millimole) of 5-phenylsulfinyl-$\Delta^6$-PGI$_1$ methyl ester 11,15-bis-t-butyl-dimethylsilyl ether.

NMR (CCl$_4$, 60 MHz):
0.05 (12H), 0.9 (21H), 1.3 (12H), 1.6–2.8 (6H), 3–3.6 (2H), 3.6 (3H, s), 4.0 (1H, bs), 4.1–4.9 (2H, m), 5.45 (2H, m), 7.5 (5H, bs),
Mass (20 eV, m/e):
592 (M+ −126)

(3) 96 mg (0.133 millimole) of 5-phenylsulfinyl$\Delta^6$-PGI$_1$ methyl ester 11,15-bis-t-butyldimethylsilyl ether was dissolved in 1 ml of tetrahydrofuran, and 98 mg (0.30 millimole) of diethylamine was added. The mixture was left to stand at room temperature for 12 hours. The reaction mixture was poured into a saturated aqueous solution of ammonium sulfate containing a small amount of triethylamine, and extracted with ethyl acetate. The resulting crude product was purified by silica gel thin-layer chromatography (benzene/ethyl acetate=8:2; aqueous ammonia 2%) to give 32 mg (0.052 millimole; yield 34%) of the captioned compound No. 800.

NMR (CCl$_4$, $\delta$ppm):
3.60 (3H, s), 3.6–4.0 (2H), 4.30 (1H, t, J=7 Hz), 4.07 (1H, bs), 4.7 (1H, m), 5.45 (2H, m).
Mass (20 eV, m/e):
610 (M+)
Analysis:
C$_{33}$H$_{60}$O$_5$Si$_2$ (M-H$_2$O) Calculated: 592.3982, Found: 592.3981.

EXAMPLE 95

Synthesis of 7-hydroxy-PGI$_2$ methyl ester 11,15-diacetate (No. 812):

286 mg (0.49 millimole) of 5-phenylsulfinyl-$\Delta^6$-PGI$_1$ methyl ester 11,15-diacetate was dissolved in 7 ml of tetrahydrofuran, and then 0.88 ml (8.5 millimoles) of diethylamine was added. The mixture was stirred overnight at room temperature, and 15 ml of a saturated aqueous solution of sodium bicarbonate was added to the reaction mixture. The mixture was extracted with 20 ml of ethyl acetate twice. The organic layers were combined, extracted with 10 ml of water three times, and dried over magnesium sulfate-potassium carbonate. The solvent was distilled off to give 259 mg of a crude product. The crude product was separated and purified by Florisil column chromatography using 30% ethyl acetate/n-hexane (containing 0.1% triethylamine) as an eluent to give 82 mg (yield 35%) of the captioned compound No. 812.

NMR (CDCl$_3$, $\delta$ppm):
3.66 (3H, s), 4.28 (1H, s), 4.50 (1H, t, J=7 Hz), 4.7–5.4 (3H, broad), 5.4–5.7 (2H, m).
Mass (20 eV, m/e);
466 (M+)

EXAMPLE 96

Synthesis of 7-fluoro-PGI$_2$ methyl ester 11,15-diacetate (No. 756) and 5-fluoro-$\Delta^6$-PGI$_1$ methyl ester 11,15-diacetate (No. 308):

44 mg of 7-hydroxy-PGI$_2$ methyl ester 11,15-diacetate was dissolved in 4 ml of dry dichloromethane, and while the solution was cooled to −40° C., 76 microliters of diethylaminosulfur trifluoride was added. The reaction mixture was stirred at −20° C. for 1 hour, and left to stand at −20° C. for 14 hours. Then, 18 ml of a saturated aqueous solution of sodium bicarbonate was added to the reaction mixture, and the mixture was extracted with 30 ml of ethyl acetate twice. The extracts were combined, washed with 20 ml of water twice, and dried over magnesium sulfate-potassium carbonate. The solvent was distilled off under reduced pressure to give 45 mg of a crude product. The crude product was separated and purified by silica gel thin-layer chromatography to give two compounds.

Compound No. 756

Amount yielded:
8 mg (yield 18%)
Mass (20 eV, m/e):
468 (M+), 448, 408, 388, 348, 328.
NMR (100 MHz, CDCl$_3$, ppm) $\delta$:
2.01 (3H, s), 2.04 (3H, s), 3.66 (3H, s), 4.77 (1H, t, J=7 Hz), 4.75–5.30 (3H, m), 4.94 (1H, d, J=56 Hz), 5.5–5.65 (2H, m).

Compound No. 308
Amount yielded:
12 mg (yield 27%)
Mass (20 eV, m/e);
468 (M+), 448, 408, 388, 348, 328.
NMR (100 MHz, CDCl$_3$)δ:
1.99 (3H, s), 2.04 (3H, s), 2.9–3.2 (1H, br), 3.67 (3H, s), 4.5–5.3 (5H, m), 5.45–5.55 (2H, m).

EXAMPLE 97

Synthesis of 7-fluoro-PGI$_2$ methyl ester 11,15-bis-t-butyldimethylsilyl ether (No. 758):

14 mg of 7-hydroxy-PGI$_2$ methyl ester 11,15-bis-t-butyldimethylsilyl ether was dissolved in 0.6 ml of dry pyridine, and 10 microliters of methanesulfonyl chloride was added. The mixture was stirred at room temperature for 3 hours. 15 ml of diethyl ether and 12 ml of a saturated aqueous solution of sodium bicarbonate were added to the reaction mixture. The mixture was shaken in a separating funnel. The aqueous layer was again extracted with 15 ml of diethyl ether. The ethereal layer was washed with 12 ml of water three times, and dried over magnesium sulfate. The solvent was distilled off under reduced pressure to give 14 mg of a crude product containing 7-mesyloxy PGI$_2$ methyl ester 11,15-bis-t-butyldimethylsilyl ether. All of the resulting product was dissolved in 1 ml of dry acetonitrile, and 51 mg of silver fluoride was added. The mixture was stirred at room temperature for 1 hour, at 60° C. for 1.5 hours, and further at room temperature for 2 days, and thereafter filtered to remove insoluble materials. The solvent was then distilled off. The residue was separated and purified by silica gel thin-layer chromatography using n-hexane/ethyl acetate (=9:1) as a developing solvent to give 1.0 mg of the captioned compound No. 758.

Mass (20 eV, m/e):
612 (M+), 592, 555, 535, 521, 460
NMR (100 MHz, CDCl$_3$) δ:
0.86 (9H, s), 0.90 (9H, s), 3.66 (3H, s), 3.8–4.4 (2H, br), 4.6–5.0 (2H, m), 4.91 (1H, d, J=5.4 Hz), 5.45–5.6 (2H, m).

EXAMPLE 98

Synthesis of 5-chloro-Δ$^6$-PGI$_1$ methyl ester 11,15-bis-t-butyldimethylsilyl ether (No. 308):

(1) 10.7 mg of PGI$_2$ methyl ester 11,15-bis-t-butyldimethylsilyl ether was dissolved in 0.3 ml of methylene chloride, and after purging the solution with argon, 7.5 microliters of triethylamine was added. The mixture was cooled to −70° C. 50 microliters of a solution of 22.6 microliters of t-butyl hypochlorite in 0.48 ml of methylene chloride was added, and the mixture was stirred at −70° C. for 40 minutes. The reaction mixture was then worked up in the same way as in Example 1 to give a crude product. The crude product was purified by silica gel thin-layer chromatography using 10% ethyl acetate/hexane as a developing solvent to give 2.4 mg (yield 19%) of 5-chloro-Δ$^6$-PGI$_1$ methyl ester 11,15-bis-t-biutyldimethylsilyl ether.

Mass (m/e)
630, 628, 592, 573, 571, 535.
NMR (CDCl$_3$) δ:
0.86 (9H, s), 0.90 (9H, s), 2.85–3.2 (1H, m), 3.66 (3H, s), 3.7–4.2 (2H, m), 4.40 (1H, m), 4.7–5.0 (1H, m), 5.00 (1H, d, J=3 Hz), 5.50 (2H, m).

(2) 31 mg of PGI$_2$ methyl ester 11,15-bis-t-butyldimethylsilyl ether was dissolved in 0.8 ml of n-hexane, and 22 microliters of triethylamine was added. After purging the solution with argon, the solution was cooled to −70° C. 0.1 ml of a solution of 65 microliters of t-butyl hypochlorite in 1 ml of n-hexane was added, and the mixture was stirred at −70° C. for 25 minutes. Furthermore, 50 microliters of the above n-hexane solution was added, and the mixture was stirred at −70° C. for 30 minutes. The reaction mixture was worked up in the same way as in Example 1, and the resulting crude product was purified by Florisil column chromatography using 0.5% ethyl acetate/n-hexane (containing 0.1% triethylamine) as an eluent to give 17.3 mg (yield 53%) of 5-chloro-Δ$^6$-PGI$_1$ methyl ester 11,15-bis-t-butyldimethylsilyl ether.

EXAMPLE 99

Test for the chemical stability of (5E)-5-chloro-PGI$_2$ sodium salt (No. 686) and (5Z)-5-chloro-PGI$_2$ sodium salt (No. 5Z-686):

6.54 ml of 0.02M potassium dihydrogen phosphate and 29.0 ml of 0.01M disodium hydrogen phosphate were mixed, and the pH of the mixture was measured by a pH meter. It was found to be 7.4.

The solution of (5E)-5-chloro-PGI$_2$ sodium salt obtained in Example 35 and the solution of (5Z)-5-chloro-PGI$_2$ sodium salt obtained in Example 36 were each added to the above buffer mixture, and their UV spectra were periodically recorded at room temperature. From the absorption values at 210 nm, the half periods of these salts were determined. It was found that the (5E)-5-chloro-PGI$_2$ sodium salt showed a half period of about 22 days, and the (5Z)-5-chloro-PGI$_2$ sodium salt, showed a half period of more than 1 month.

EXAMPLE 100

Measurement of the hypotensive activity:

The actions of the prostacyclin derivatives of the invention on the blood pressure and heart rate of rats were examined by intravenous injection under anesthesia.

Male wister rats weighing about 250 g were used. Urethane (500 mg/kg) and α-chloralose (100 mg/kg) were intraperitoneally administered to the rats. The rats were anesthetized and fixed in place.

Each of the test compounds was dissolved in a small amount of ethanol and diluted with 0.05M Tris buffer saline (pH 9) to adjust the final ethanol concentration to not more than 5%. The solution was intravenously injected into the rats through a catheter inserted into the femoral vein.

The blood pressure of the rats was measured by a pressure transducer through a catheter inserted into the carotid artery of the rats. The heart rate was determined from the blood pressure pulse.

The action of the test compound on the blood pressure was expressed as the dosage (P-ED$_{20}$, μg/kg) of the test compound which caused a 20% lowering of the mean blood pressure before administration of the compound. The action of the test compound on the heart rate was expressed as the dosage (H-ED$_{10}$, μg/kg) of the test compound which caused a 10% increase of the heart rate from the heart rate before administration of the test compound.

The results are shown in Table 1.

TABLE 1

| | Compound | P-ED$_{20}$ (μg/kg i.v.) | H-ED$_{10}$ (μg/kg i.v.) |
|---|---|---|---|
| Invention | 688 | 0.7 | 1.9 |
| | 686 | 2.4 | >10 |
| Comparison | PGI$_2$ | 0.02 | 0.04 |

EXAMPLE 101

(1) in vitro inhibitory activity of platelet aggregation:

The in vitro platelet aggregation inhibiting activities of the compounds of the invention were examined by using rabbits. Blood was withdrawn from the ear vein of Japanese domestic white male rabbits weighing 2.5 to 3.5 kg. A mixture of a 3.8% trisodium citrate solution and the blood in a ratio of 1:9 was centrifuged at a speed of 1000 rpm for 10 minutes. The upper layer was separated as platelet-rich plasma (PRP). The lower layer was further centrifuged at a speed of 2800 rpm for 10 minutes. The upper layer was separated as platelet-poor plasma (PPP). The number of platelets was adjusted to $6 \times 10^5/\mu l$ to $7 \times 10^5/\mu l$ by diluting the PRP with PPP. 25 microliters of the test compounds prepared as shown below was added in an amount of 25 to 250 microliters of PRP after the adjustment, and the mixture was pre-incubated at 37° C. for 2 minutes, and then 10 μM (final) of ADP was added. By using an aggregometer, changes in transmission were recorded.

The drug was dissolved in ethanol to a concentration of 10 mg/ml. When its activity was measured, it was used after being diluted with phosphate buffer (pH 7.4). Furthermore, after dilution with the buffer, the drug was left to stand at 0° C. for 4 hours, and the activity of the drug was similarly measured.

The rate of inhibition of platelet aggregation was determined from the following equation.

Inhibition rate (%) = $(1 - T/T_o) \times 100$ $T_o$: the transmittance of the system containing the phosphate buffer, T: the transmittance of the system to which the test drug was added.

The minimum concentration of the drug which inhibited more than 50% of platelet aggregation was shown as an IC$_{50}$ value.

The results are shown in Table 2.

TABLE 2

| | Compound | IC$_{50}$ (μg/ml) 0 hr. | 4 hr |
|---|---|---|---|
| Invention | 637 | 0.34 | 0.38 |
| | 688 | 0.05 | 0.05 |
| | 636 | 0.62 | 0.51 |
| | 686 | 0.14 | 0.12 |
| Comparison | PGI$_2$ | 0.0047 | 0.56 |

It is seen from Table 2 that the prostacyclin derivatives of the invention do not decrease in platelet aggregation inhibiting activity even after the lapse of 4 hours, and this fact is evidence that they are highly stabilized compounds.

(2) From the results obtained in Examples 100 and 101, the ratio of the blood pressure lowering activity and the platelet aggregation inhibiting activity was calculated. The result is shown in Table 3 together with the ratio obtained with PGI$_2$.

TABLE 3

| | | P-ED$_{20}$/ platelet IC$_{50}$ | Ratio |
|---|---|---|---|
| Comparison | PGI$_2$ | 4.3 | 1 |
| Invention | No. 688 | 14.0 | 32 |
| | No. 686 | 17.1 | 4 |

As shown in Table 3, the compounds Nos. 686 and 688 of the invention have stronger activities of inhibiting platelet aggregation in comparison with their blood pressure lowering activities in contrast to PGI$_2$, and therefore have higher selectivity of pharmacological activity than PGI$_2$.

EXAMPLE 102

The prostocyclin derivatives of the invention were intraduodenally administered to conscious rats, and their action on the blood pressure was examined.

Male SD rats weighing about 200 g were used as experimental animals. These rats had been fasted for 16 hours before the start of the experiment. A catheter was inserted into the femoral artery of the rats under ether anesthesia, and then the rats were restrained within a Bollman cage. After more than 1 hour from awakening, each of the test compounds was intraduodenally administered.

The test compound was dissolved in a small amount of ethanol, and then diluted with 0.05M Tris buffer (pH 9) to adjust the final concentration of ethanol to not more than 5%. The mean blood pressure was measured by means of a pressure transducer through the catheter inserted into the femoral artery.

The results are shown in Table 4.

TABLE 4

| Compound | Dose mg/kg i.d. | N | Time (min) 0 | 5 | 10 | 15 | 30 | 60 | 120 |
|---|---|---|---|---|---|---|---|---|---|
| Control | — | 4 | 121 ± 3 | 123 ± 4 | 121 ± 3 | 118 ± 5 | 119 ± 3 | 118 ± 4 | 119 ± 4 |
| (688) | 1 | 4 | 102 ± 4 | 101 ± 4 | 97 ± 3 | 99 ± 4 | 104 ± 3 | 100 ± 4 | 100 ± 2 |
| | 3 | 4 | 104 ± 2 | 100 ± 3 | 100 ± 3 | 103 ± 2 | 102 ± 3 | 102 ± 2 | 100 ± 2 |
| Sodium salt of PGI$_2$ | 3 | 4 | 109 ± 1 | 84 ± 3 | 101 ± 4 | 110 ± 2 | 109 ± 1 | 107 ± 2 | 103 ± 2 |

EXAMPLE 103 extra vivo inhibitory activity of platelet aggregation:

The extra vivo platelet aggregation inhibitory activity of the prostacyclin derivatives of the invention were measured by using art. The test compound of the invention in ethanol was diluted with 0.05M Tris buffer (pH 9.0) and as a control, only the 0.05M Tris buffer solution was used. These solutions were each intraduodenally administered in a dose of 1 ml/kg to SD strain rats weighing about 200 g which had been fasted for 16 hours. Thirty minutes after the administration, blood was drawn off from the aorta using trisodium citrate so that the ratio of the blood to 3.8% trisodium citrate was 9:1. The blood was centrifuged at a speed of 800 rpm for 10 minutes. The upper layer was separated as platelet-rich plasma (PRP). The lower layer was further centrifuged at a speed of 2800 rpm for 10 minutes. The upper layer was separated as platelet poor plasma (PPP). 250 microliters of the resulting PRP was taken into an aggregometer cuvette, and incubated at 37° C. for 2 minutes. Then, 25 microliters of a 1.25 μM ADP disodium solution adjusted by dissolving with 0.1M tris-HCl buffer (pH 8.0) was added. The aggregation curve was recorded for 3 minutes. The maximum degree of aggregation of platelets within this time period was read, and the rate of inhibition of platelet aggregation was calculated from the following equation.

Rate of platelet aggregation inhibition
$(\%) = (1 - (T_D/T_C)) \times 100$ $T_C$: the transmittance of the control glroup (to which only the 0.05M Tris buffer solution was administered),
$T_D$: the transmittance of the drug administered group.

The results are shown in Table 5.

TABLE 5

| Compound | Dose mg/kg i.d. | N | inhibition (%) |
|---|---|---|---|
| (688) | 3 | 4 | 87.5 ± 5.8 |
| Sodium salt of PGI$_2$ | 3 | 4 | 56.5 ± 11.3 |

It is seen from Table 5 that the compound No. 688 of the present invention has stronger platelet aggregating activity than the sodium salt of PGI$_2$. On the other hand, Table 4 demonstrates that the sodium salt of PGI$_2$ has stronger blood pressure lowering activity than the compound No. 688 of the present invention (especially five minutes later).

The above fact substantiates that the compound of this invention has high platelet aggregation inhibiting activity, but low blood pressure lowering activity, showing selectivity in action.

EXAMPLE 104

Measurement of the activity of inhibiting metastasis of a malignant tumor:

Mice were used as experimental animals. Lewis lung carcinoma ($4 \times 10^5$ cells/100 μl) was transplanted into the foot pad of each mouse. For seven days from the 5th to the 11th day after the transplantation, the compound No. 686 of the invention was intraperitoneally administered to the mouse once a day. On the 12th day, the foot at the primary nest was cut off, and the weight of the cut foot (primary nest portion) was measured. On the 20th day after the transplantation, the number of nests which metastasized to the lungs was measured.

The results are shown in Table 6.

TABLE 6

| | Dose/day | Number of animals | Number of nests which metastasized to the lungs (measured on the 20th day) | Weight of the primary next portion measured on the 12th day (g) |
|---|---|---|---|---|
| Control | 0.5% saline water | 5 | 43.8 ± 16.5 | 2.89 ± 0.57 |
| Compound No. 686 | 10 μg/kg | 5 | 25.6 ± 12.0 | 2.17 ± 0.86 |

The results given in Table 6 demonstrate that the compound No. 686 of the invention inhibited metastasis of the primary nest to the lungs, and reduced the primary nest.

EXAMPLE 105

Preparation of enteric-coated tablets:
Enteric-coated tablets of the following recipe were prepared.

| Active ingredient | 1 mg |
|---|---|
| Lactose | 250 mg |
| Starch | 80 mg |
| Talc | 20 mg |
| Magnesium stearate | 5 mg |
| | 356 mg in total |

A mixture consisting of the active ingredient, lactose, starch, talc and magnesium stearate was tableted by means of a rotary tableting machine. A solution of hydroxypropyl methyl cellulose phthalate in ethanol was sprayed onto the resulting tablets in a coating pan to give the desired enteric-coated tablets.

Compound No. 688 was used as a typical example of the active ingredient.

EXAMPLE 106

Preparation of an injectable solution:
Compound No. 688 was used as the active ingredient. 600 μg of the compound was dissolved in 5 ml of ethanol, and the solution was sterilized by passing it through a bacteria-holding filter. 0.1 ml of the solution was filled in each of 1-ml ampoules, and the ampoules were sealed up. The contents of the ampoules are diluted, for example, with Tris-HCl buffer to 1 ml for injection.

EXAMPLE 107

Production of tablets:
Tablets were produced each of which had the following composition.

| Active component | 1 mg |
|---|---|
| Lactose | 300 mg |
| Potato starch | 80 mg |
| Polyvinyl pyrrolidone | 10 mg |
| Magnesium stearate | 5 mg |
| | 400 mg in total |

The active ingredient, lactose and potato starch were mixed, and the mixture was equally wetted with a 20% ethanol solution of polyvinyl pyrrolidone. The wet mixture was passed through a 20-mesh screen, and dried at 45° C. Then, the dried particles were again passed through a 20-mesh screen. The resulting granules were mixed with magnesium stearate, and compressed into tablets.

Compound (688) was used typically as the active ingredient.

EXAMPLE 108

Production of powder:
A powder was prepared in accordance with the following formulation.

| Active ingredient | 2 mg |
|---|---|
| Lactose | 100 mg |
| Corn starch | 100 mg |
| Hydroxypropyl cellulose | 10 mg |

| | |
|---|---|
| | 220 mg |

The active ingredient, lactose and corn starch were mixed, and an aqueous solution of hydroxypropyl cellulose was added. The mixture was dried to form a dust powder.

Compound 686 was used typically as the active ingredient.

EXAMPLE 109

Preparation of a nasal drop:

A nasal drop having the following recipe was prepared.

| | |
|---|---|
| Active ingredient | 0.5 mg |
| Physiological saline (containing sodium bisulfite and chlorobutanol) | 0.1 ml |

The active ingredient in the above-indicated amount (the amount for a single administration) was dissolved in physiological saline containing 0.15% of sodium bisulfite as an antioxidant and 0.5% of chlorobutanol as an antiseptic to prepare a nasal drop.

Compound No. 686 was used typically as the active ingredient.

What we claim is:

1. A halogenated prostacyclin selected from the group consisting of
halogenated $PGI_1$ of the formula

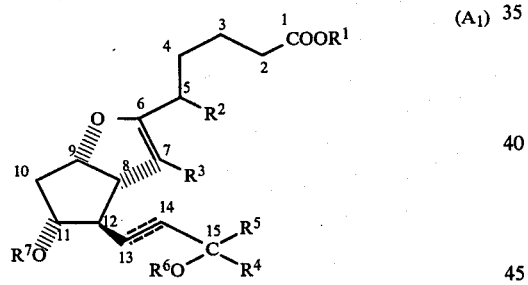

wherein
the symbol ≡≡≡≡≡ between the 13- and 14-positions represents a single, double or triple bond,
$R^1$ represents hydrogen, $C_1$-$C_{10}$ alkyl, substituted or unsubstituted phenyl, substituted or unsubstituted $C_5$-$C_8$ cycloalkyl, substituted or unsubstituted $C_5$-$C_8$ cycloalkenyl, substituted or unsubstituted phenyl ($C_1$-$C_2$) alkyl, or one equivalent of a cation whose salt is pharmaceutically acceptable,
$R^2$ and $R^3$ represent hydrogen or halogen selected from the group consisting of fluorine, chlorine, bromine and iodine, provided that $R^2$ and $R^3$ are not both hydrogen,
$R^4$ represents hydrogen, methyl, ethynyl, trimethylsilylethynyl or t-butyldimethylsilylethynyl,
$R^5$ represents unsubstituted $C_5$-$C_8$ alkyl, $C_1$-$C_5$ alkyl substituted by a substituent selected from the group consisting of phenyl, phenoxy, $C_1$-$C_6$ alkoxy and $C_5$-$C_6$ cycloalkyl, which substituent may be substituted, substituted or unsubstituted $C_5$-$C_8$ cycloalkyl, or substituted or unsubstituted $C_5$-$C_8$ cycloalkenyl, and $R^6$ and $R^7$ are identical or different and each represents hydrogen, $C_2$-$C_7$ carboacyl, tri-($C_1$-$C_7$) hydrocarbonsilyl or a group capable of forming an acetal linkage with the oxygen atom of a hydroxyl group,
said substituted groups having 1 to 3 substituents selected from the group consisting of (1) halogen, (2) hydroxyl, (3) $C_2$-$C_7$ carboacyloxy, (4) $C_1$-$C_4$ alkyl which is unsubstituted or substituted by halogen, (5) $C_1$-$C_4$ alkoxy which is unsubstituted or substituted by halogen, (6) nitrile, (7) carboxyl and (8) ($C_1$-$C_6$) alkoxycarbonyl,
provided that when $R^2$ is fluorine and $R^3$ is hydrogen $R^5$ is not unsubstituted $C_5$-$C_8$ alkyl, and
halogenated $PGI_2$ of the formula

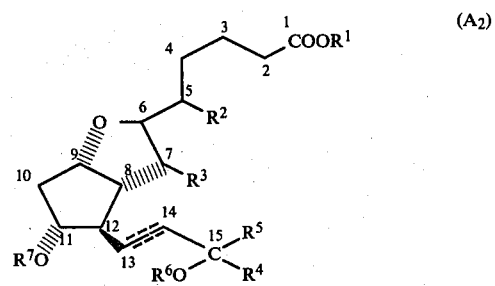

wherein
the symbol ≡≡≡≡≡ between the 13- and 14-positions, $R^1$, $R^2$, $R^3$, $R^4$, $R^5$, $R^6$ and $R^7$ are as defined above,
provided that when $R^2$ is hydrogen or fluorine, $R^3$ is not hydrogen, and when $R^2$ is hydrogen and $R^3$ is halogen other than iodine $R^5$ is not unsubstituted $C_5$-$C_8$ alkyl.

2. The halogenated prostacyclin of claim 1 which is selected from the halogenated $PGI_1$ of formula ($A_1$) in which $R^2$ and $R^3$ represent a hydrogen or fluorine atom.

3. The halogenated prostacyclin of claim 1 which is selected from the halogenated $PGI_2$ of formula ($A_2$) in which $R^2$ represents a hydrogen or fluorine atom and $R^3$ represents a fluorine atom.

4. The halogenated prostacyclin of claim 1 which is selected from the halogenated $PGI_1$ of formula ($A_1$) in which $R^2$ and $R^3$ represent a hydrogen, chlorine, bromine or iodine atom.

5. The halogenated prostacyclin of claim 1 which is selected from the halogenated $PGI_2$ of formula ($A_2$) in which $R^2$ and $R^3$ represent a hydrogen, chlorine, bromine or iodine atom.

6. The halogenated prostacyclin of any one of claims 2, 4, 5, 1 and 3 wherein $R^1$ represents a hydrogen atom, a $C_1$-$C_{10}$ alkyl group, or one equivalent of a cation whose salt is pharmaceutically acceptable.

7. The halogenated prostacyclin of any one of claims 2, 4, 5, 1 and 3 wherein $R^4$ represents a hydrogen atom or a methyl group.

8. The halogenated prostacyclin of any one of claims 2, 4, 5, 1 and 3 wherein $R^5$ represents an n-pentyl, n-hexyl, 2-methyl-1-hexyl, 2-methyl-2-hexyl, cyclopentyl or cyclohexyl group.

9. The halogenated prostacyclin of any one of claims 2, 4, 5, 1 and 3 wherein $R^6$ and $R^7$ are identical or different and each represents a hydrogen atom, a tri($C_1$-$C_4$)alkylsilyl group, a diphenyl($C_1$-$C_4$)alkylsilyl group, a 2-tetrahydropyranyl group, a 2-tetrahydrofuranyl group, a 1-ethoxyethyl group, a 2-ethoxy-2-propyl group, a (2-methoxyethoxy)methyl group, a 6,6-dimethyl-3-oxa-2-oxo-bicyclohex-4-yl group, an acetyl group or a benzoyl group.

10. The halogenated prostacyclin of any one of claims 5, 1 and 3 wherein in formula ($A_2$), the bond between the carbon atom at the 5-position of the double bond between the 5- and 6-positions and the carbon atom at the 4-position is cis to the bond between the carbon atom at the 6-position of the double bond and the oxygen atom.

11. The halogenated prostacyclin of any one of claims 2, 4, 5, 1 and 3 wherein the bond between the 13- and 14-positions is a trans-double bond or a triple bond.

12. The halogenated prostacyclin of claim 1 which is selected from the group consisting of
halogenated $PGI_1$ of the formula

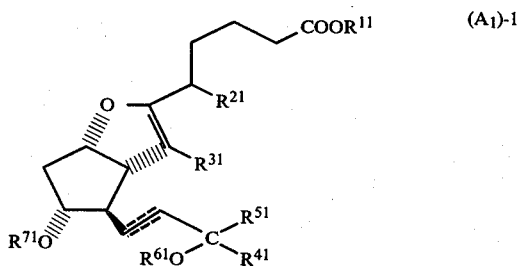

(A₁)-1 wherein
the symbol ======== between the 13- and 14-positions represents a single, double or triple bond,
$R^{11}$ represents hydrogen, $C_1-C_{10}$ alkyl, or one equivalent of a cation whose salt is pharmaceutically acceptable,
$R^{21}$ and $R^{31}$ represent hydrogen, fluorine or chlorine, provided that $R^{21}$ and $R^{31}$ are not both hydrogen,
$R^{41}$ represents hydrogen or methyl,
$R^{51}$ represents n-pentyl, n-hexyl, 2-methyl-1-hexyl, 2-methyl-2-hexyl, cyclopentyl or cyclohexyl, and
$R^{61}$ and $R^{71}$ represent hydrogen or acetyl,
provided that when $R^{21}$ is fluorine and $R^{31}$ is hydrogen $R^{51}$ is cyclohexyl, and
halogenated $PGI_2$ of the formula

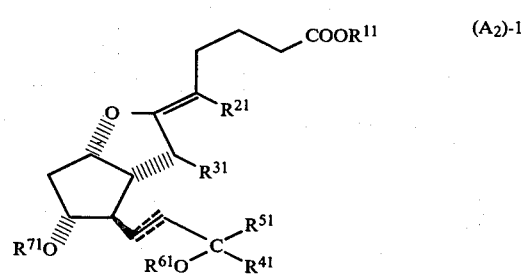

(A₂)-1 wherein
the symbol ======== between the 13- and 14-positions, $R^{11}$, $R^{21}$, $R^{31}$, $R^{41}$, $R^{51}$, $R^{61}$ and $R^{71}$ are as defined above,
provided that when $R^{21}$ is hydrogen or fluorine $R^{31}$ is not hydrogen, and when $R^{21}$ is hydrogen and $R^{31}$ is fluorine or chlorine $R^{51}$ is cyclohexyl.

13. The halogenated prostacyclin of claim 12 wherein in formula ($A_2$)-1, the bond between the carbon atom at the 5-position of the double bond between the 5- and 6-positions and the carbon atom at the 4-position is cis to the bond between the carbon atom at the 6-position of the double bond and the oxygen atom.

14. The halogenated prostacyclin of claim 12 wherein the bond between the 13- and 14-positions is a trans-double bond or a triple bond.

15. A pharmaceutical composition for controlling vascular actions, said composition comprising a pharmaceutically effective amount of a halogenated prostacyclin selected from the group consisting of the halogenated $PGI_1$ of formula ($A_1$)-1 in claim 12 and the halogenated $PGI_2$ of formula ($A_2$)-1 in claim 12 as an active ingredient together with a pharmaceutically acceptable carrier.

16. The pharmaceutical composition of claim 15 which is for vasodilation, blood pressure lowering or antithrombosis.

17. The pharmaceutical composition of claim 15 or 16 which is for controlling arteriosclerosis, angina pectoris, myocardial infarction, endotoxin shock, pulmonary hypertension, cerebral apoplexy, transient ischemic attack, thrombocytopenic purpura, deep vein thrombosis or peripheral vascular diseases.

18. The pharmaceutical composition of claim 15 which is for use in organ transplantation, vascular surgery or extracorporeal circulation.

19. A medicament in unit dosage form comprising the pharmaceutical composition of claim 15.

20. A method for controlling vascular actions of a warm-blooded animal, which comprises administering a pharmaceutically effective amount of the halogenated prostacyclin of claim 12, or the pharmaceutical composition of claim 15, or the medicament of claim 19 to said animal which requires such control.

21. The method of claim 20 wherein the warm-blooded animal is a human.

22. The method of claim 21 wherein the pharmaceutically effective amount is about 0.02 μg to about 2 mg/kg of body weight/day.

23. A hydroxyprostacyclin of the formula

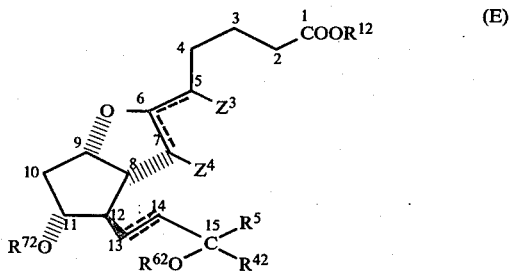

(E)

wherein
the symbol ======== between the 5-, 6- and 7-positions represents a double bond between the 5- and 6-positions or between the 6- and 7-positions,
the symbol between the 13- and 14-positions represents a single, double or triple bond,
$R^{12}$ represents $C_1-C_{10}$ alkyl, substituted or unsubstituted phenyl, substituted or unsubstituted $C_5-C_8$ cycloalkyl, substituted or unsubstituted $C_5-C_8$ cycloalkenyl, or substituted or unsubstituted phenyl ($C_1-C_2$) alkyl,
$R^{42}$ represents hydrogen, methyl, trimethylsilylethynyl or t-butyldimethylsilylethynyl,
$R^5$ represents unsubstituted $C_5-C_8$ alkyl, $C_1-C_5$ alkyl substituted by a substituent selected from the group consisting of phenyl, phenoxy, $C_1-C_6$ alkoxy and $C_5$–$C_6$ cycloalkyl, which substituent may be substituted, substituted or unsubstituted $C_5$–$C_8$ cycloalkyl, or substituted or unsubstituted $C_5$–$C_8$ cycloalkenyl, $R^{62}$ and $R^{72}$ are identical or different and each represents $C_2$–$C_7$ carboacyl, tri($C_1$–$C_7$)hydrocarbonsilyl or a group capable of forming an acetal linkage with the oxygen atom of a hydroxyl group, and $Z^3$ and $Z^4$ are different from each other and represent hydrogen or hydroxyl, said substituted groups having 1 to 3 substituents selected from the group consisting of (1) halogen; (2) hydroxyl, (3) $C_2$–$C_7$ carboacyloxy, (4) $C_1$–$C_4$ alkyl which is unsubstituted or substituted by halogen, (5) $C_1$–$C_4$ alkoxy which is unsubstituted or substituted by halogen, (6) nitrile, (7) carboxyl and (8) ($C_1$–$C_6$)alkoxycarbonyl, provided that when $Z^3$ is hydrogen, a double bond exists between the 5- and 6-positions; when $Z^4$ is hydrogen, a double bond exists between the 6- and 7-positions; and when $Z^3$ is hydrogen and a double bond exists between the 13- and 14-positions, $R^5$ is not unsubstituted $C_5$–$C_8$ alkyl.

* * * * *

UNITED STATES PATENT AND TRADEMARK OFFICE
CERTIFICATE OF CORRECTION

PATENT NO. : 4,472,428

DATED : September 18, 1984

INVENTOR(S) : Takeshi TORU, Kiyoshi BANNAI, Takeo OBA, Toshio TANAKA, Noriaki OKAMURA, Kenzo WATANABE, Seizi KUROZUMI, Akira OHTSU, and Tatsuyuki NARUCHI It is certified that error appears in the above-identified patent and that said Letters Patent is hereby corrected as shown below:

Column 66, in the formula at lines 16-28, change the single bond (—) between the 5 position and the 6 position to a double bond (=).

Column 68, line 54, change "=====" to -- ===== --;

line 57, insert -- ===== -- in the blank space after "symbol".

Signed and Sealed this

Twenty-ninth Day of October 1985

[SEAL]

Attest:

DONALD J. QUIGG

Attesting Officer

Commissioner of Patents and Trademarks—Designate